United States Patent
Bullington et al.

(10) Patent No.: US 12,097,027 B2
(45) Date of Patent: Sep. 24, 2024

(54) SYSTEMS AND METHODS FOR SAMPLE COLLECTION WITH REDUCED HEMOLYSIS

(71) Applicant: Magnolia Medical Technologies, Inc., Seattle, WA (US)

(72) Inventors: Gregory J. Bullington, Seattle, WA (US); Richard G. Patton, Seattle, WA (US); Shan E. Gaw, Seattle, WA (US); Jay M. Miazga, Langley, WA (US); Jed McCann, Seattle, WA (US); Paul Goldenbaum, San Antonio, TX (US)

(73) Assignee: Magnolia Medical Technologies, Inc., Seattle, WA (US)

( * ) Notice: Subject to any disclaimer, the term of this patent is extended or adjusted under 35 U.S.C. 154(b) by 527 days.

(21) Appl. No.: 15/818,173

(22) Filed: Nov. 20, 2017

(65) Prior Publication Data
US 2018/0140240 A1    May 24, 2018

Related U.S. Application Data

(60) Provisional application No. 62/423,993, filed on Nov. 18, 2016.

(51) Int. Cl.
*A61B 5/15* (2006.01)
*A61B 5/153* (2006.01)
(Continued)

(52) U.S. Cl.
CPC .... *A61B 5/150206* (2013.01); *A61B 5/15003* (2013.01); *A61B 5/150099* (2013.01);
(Continued)

(58) Field of Classification Search
CPC ........... A61B 5/15; A61B 5/153; A61B 5/154; A61B 5/155; A61B 5/162; A61B 5/178;
(Continued)

(56) References Cited

U.S. PATENT DOCUMENTS

| 2,638,897 A | 5/1953 | Poitras |
| 2,697,435 A | 12/1954 | Benjamin |

(Continued)

FOREIGN PATENT DOCUMENTS

| CN | 101626803 B | 8/2013 |
| DE | 102005020648 A1 | 11/2006 |

(Continued)

OTHER PUBLICATIONS

Ihan, Alojz et al. "An In Vitro Evaluation of the Red Cell Damage and Hemocompatibility of Different Central Venous Catheters." BioMed research international vol. 2020 8750150. Apr. 14, 2020 (Year: 2020).*

(Continued)

*Primary Examiner* — Yi-Shan Yang
*Assistant Examiner* — Kyle W. Kretzer
(74) *Attorney, Agent, or Firm* — Cooley LLP

(57) ABSTRACT

A collection system configured to maintain the integrity of a bodily fluid sample has a proximal end portion, a distal end portion, and an inner surface defining a fluid flow path therethrough. The distal end portion is configured to be placed in fluid communication with a patient. The proximal end portion is configured to be placed in fluid communication with a fluid reservoir. The fluid flow path defined by the inner surface is associated with at least one flow characteristic configured to limit a stress within the flow of the bodily fluid between the distal end portion and the proximal end portion.

4 Claims, 37 Drawing Sheets

(51) Int. Cl.
  *A61B 5/154*   (2006.01)
  *A61B 5/155*   (2006.01)
  *A61M 5/162*   (2006.01)
  *A61M 5/178*   (2006.01)
  *A61M 5/48*    (2006.01)
  *A61M 39/02*   (2006.01)
  *A61M 39/22*   (2006.01)
  *B01L 3/00*    (2006.01)
  *A61M 5/32*    (2006.01)
  *A61M 25/00*   (2006.01)
  *A61M 25/06*   (2006.01)

(52) U.S. Cl.
  CPC .. *A61B 5/150221* (2013.01); *A61B 5/150236* (2013.01); *A61B 5/150244* (2013.01); *A61B 5/150251* (2013.01); *A61B 5/150351* (2013.01); *A61B 5/150396* (2013.01); *A61B 5/150519* (2013.01); *A61B 5/150572* (2013.01); *A61B 5/150732* (2013.01); *A61B 5/15074* (2013.01); *A61B 5/150946* (2013.01); *A61B 5/153* (2013.01); *A61B 5/154* (2013.01); *A61B 5/155* (2013.01); *A61M 5/162* (2013.01); *A61M 5/178* (2013.01); *A61M 5/48* (2013.01); *A61M 39/0208* (2013.01); *A61M 39/22* (2013.01); *B01L 3/50825* (2013.01); *B01L 3/563* (2013.01); *A61B 5/150389* (2013.01); *A61M 5/3286* (2013.01); *A61M 25/005* (2013.01); *A61M 25/065* (2013.01); *B01L 2200/0689* (2013.01); *B01L 2300/042* (2013.01); *B01L 2300/044* (2013.01); *B01L 2300/069* (2013.01); *B01L 2300/0854* (2013.01); *B01L 2400/0457* (2013.01); *B01L 2400/0478* (2013.01); *B01L 2400/049* (2013.01); *B01L 2400/0616* (2013.01); *B01L 2400/084* (2013.01)

(58) Field of Classification Search
  CPC .......... A61B 5/150221; A61B 5/15003; A61B 5/150946; A61B 5/150389; A61B 5/150251; A61B 5/150099; A61B 5/150572; A61B 5/150732; A61B 5/150244; A61B 5/150206; A61B 5/150351; A61B 5/150396; A61B 5/150236; A61B 5/15074; A61B 5/150519; A61M 25/06; A61M 5/32; A61M 5/48; A61M 39/02; A61M 39/22; A61M 5/162; A61M 5/3286; A61M 39/0208; A61M 25/005; A61M 5/178; A61M 25/065; B01L 3/00; B01L 2300/069; B01L 2200/0689; B01L 2400/0616; B01L 3/563; B01L 2400/0457; B01L 3/50825; B01L 2400/049; B01L 2300/042; B01L 2300/044; B01L 2400/084; B01L 2400/0478; B01L 2300/0854
  See application file for complete search history.

(56) References Cited

U.S. PATENT DOCUMENTS

| | | |
|---|---|---|
| 2,952,258 A | 9/1960 | Chandler |
| 3,739,778 A | 6/1973 | Monestere, Jr. et al. |
| 3,960,139 A | 6/1976 | Bailey |
| 3,978,846 A | 9/1976 | Bailey |
| 3,996,923 A | 12/1976 | Guerra |
| 4,106,491 A | 8/1978 | Guerra |
| 4,106,497 A | 8/1978 | Percarpio |
| 4,140,108 A | 2/1979 | Nugent |
| 4,275,730 A | 6/1981 | Hussein |
| 4,317,456 A | 3/1982 | Percarpio |
| 4,340,067 A | 7/1982 | Rattenborg |
| 4,340,068 A | 7/1982 | Kaufman |
| 4,398,544 A | 8/1983 | Nugent et al. |
| 4,416,290 A | 11/1983 | Lutkowski |
| 4,676,256 A * | 6/1987 | Golden ............... A61B 5/15003 600/575 |
| 4,679,571 A | 7/1987 | Frankel et al. |
| 4,703,763 A | 11/1987 | McAlister et al. |
| 4,714,461 A | 12/1987 | Gabel |
| 4,772,273 A | 9/1988 | Alchas |
| 5,032,116 A | 7/1991 | Peterson et al. |
| 5,035,688 A | 7/1991 | Inui |
| 5,054,498 A | 10/1991 | Melet |
| 5,066,284 A | 11/1991 | Mersch et al. |
| 5,116,323 A | 5/1992 | Kreuzer et al. |
| 5,334,162 A | 8/1994 | Harris |
| 5,354,537 A | 10/1994 | Moreno |
| 5,372,143 A | 12/1994 | Bernes et al. |
| 5,429,610 A | 7/1995 | Vaillancourt |
| 5,439,022 A | 8/1995 | Summers et al. |
| 5,454,786 A | 10/1995 | Harris |
| 5,575,777 A | 11/1996 | Cover et al. |
| 5,685,846 A | 11/1997 | Michaels, Jr. |
| 5,824,001 A | 10/1998 | Erskine |
| 5,873,841 A | 2/1999 | Brannon |
| 5,911,705 A | 6/1999 | Howell |
| 5,947,932 A | 9/1999 | Desecki et al. |
| 6,013,037 A | 1/2000 | Brannon |
| 6,592,555 B1 | 7/2003 | Wen-Pi |
| 6,716,396 B1 | 4/2004 | Anderson et al. |
| 7,314,452 B2 | 1/2008 | Madonia |
| 7,615,033 B2 | 11/2009 | Leong |
| 7,744,573 B2 | 6/2010 | Gordon et al. |
| 7,766,879 B2 | 8/2010 | Tan et al. |
| 7,914,508 B2 | 3/2011 | Engstrom |
| 8,070,725 B2 | 12/2011 | Christensen |
| RE43,283 E | 3/2012 | Ishida et al. |
| 8,383,044 B2 | 2/2013 | Davis et al. |
| 8,412,300 B2 | 4/2013 | Sonderegger |
| 8,603,009 B2 | 12/2013 | Tan et al. |
| 8,747,779 B2 | 6/2014 | Sprague et al. |
| 8,795,198 B2 | 8/2014 | Tan et al. |
| 9,314,201 B2 | 4/2016 | Burkholz et al. |
| 9,320,459 B2 | 4/2016 | Chin et al. |
| 9,855,386 B2 | 1/2018 | Close et al. |
| 9,877,674 B2 | 1/2018 | Holmes et al. |
| 9,895,092 B2 | 2/2018 | Burkholz |
| 9,999,383 B2 | 6/2018 | Bullington et al. |
| 10,856,791 B2 | 12/2020 | McHale et al. |
| 11,318,459 B2 | 5/2022 | Shi et al. |
| 2001/0010247 A1 * | 8/2001 | Snow ............... A61M 25/0041 156/171 |
| 2001/0039058 A1 | 11/2001 | Iheme et al. |
| 2003/0023230 A1 | 1/2003 | Lewis et al. |
| 2005/0148993 A1 | 7/2005 | Mathias et al. |
| 2005/0200129 A1 * | 9/2005 | Bongiorno ............... F16L 23/02 285/364 |
| 2005/0273019 A1 | 12/2005 | Conway et al. |
| 2006/0018790 A1 | 1/2006 | Naka et al. |
| 2008/0185056 A1 | 8/2008 | Diodati et al. |
| 2008/0283473 A1 | 11/2008 | Holmes et al. |
| 2009/0173685 A1 | 7/2009 | Imai et al. |
| 2009/0227896 A1 | 9/2009 | Tan et al. |
| 2009/0305315 A1 * | 12/2009 | Gandola ............... B01L 3/563 435/13 |
| 2009/0308184 A1 * | 12/2009 | Blekher ............ A61B 5/150274 220/254.1 |
| 2010/0094171 A1 | 4/2010 | Conway et al. |
| 2010/0252118 A1 | 10/2010 | Fraden et al. |
| 2011/0009717 A1 | 1/2011 | Davis et al. |
| 2011/0046602 A1 | 2/2011 | Grimm et al. |
| 2011/0178427 A1 | 7/2011 | Tan et al. |
| 2012/0323142 A1 | 12/2012 | Allen et al. |
| 2013/0295602 A1 | 11/2013 | Fowler et al. |
| 2014/0276039 A1 | 9/2014 | Cowan et al. |
| 2014/0305196 A1 | 10/2014 | Ellis et al. |

(56) References Cited

U.S. PATENT DOCUMENTS

| | | | |
|---|---|---|---|
| 2014/0364815 A1* | 12/2014 | Paspa | A61M 25/065 604/272 |
| 2015/0032067 A1* | 1/2015 | Bullington | A61B 5/150633 604/274 |
| 2015/0073304 A1 | 3/2015 | Millerd | |
| 2016/0073937 A1 | 3/2016 | Burkholz et al. | |
| 2016/0367177 A1 | 12/2016 | Edelhauser et al. | |
| 2017/0336307 A1* | 11/2017 | Distel | G01N 1/2813 |
| 2018/0093077 A1 | 4/2018 | Harding et al. | |
| 2018/0242890 A1 | 8/2018 | Chickering, III et al. | |

FOREIGN PATENT DOCUMENTS

| | | | |
|---|---|---|---|
| EP | 0208053 B1 | 12/1991 | |
| EP | 0486059 B1 | 1/1997 | |
| JP | H0910302 A | 1/1997 | |
| JP | 2001276181 A | 10/2001 | |
| JP | 2006026327 A | 2/2006 | |
| JP | 5620541 B2 | 11/2014 | |
| WO | WO-9929232 A1 | 6/1999 | |
| WO | WO-2008157511 A1 | 12/2008 | |
| WO | WO-2009113999 A2 | 9/2009 | |
| WO | WO 2015/007853 | 1/2015 | |
| WO | WO 2017/019552 | 2/2017 | |
| WO | WO-2018094310 A1 | 5/2018 | |

OTHER PUBLICATIONS

Mahmud, Shohel, A. Sadrul Islam, and C. Feroz. "Flow and heat transfer characteristics inside a wavy tube." Heat and mass transfer 39.5 (2003): 387-393 (Mahmud) (Year: 2003).*

Bian, Yongning, et al. "Effects of dimensions on the fluid flow and mass transfer characteristics in wavy-walled tubes for steady flow." Heat and Mass Transfer 49 (2013): 723-731 (Yongning). (Year: 2013).*

Tatsuo Nishimura, Yoshiji Ohori, Yuji Kawamura, Flow Characteristics in a Channel With Symmetric Wavy Wall for Steady Flow, Journal of Chemical Engineering of Japan, 1984, vol. 17, Issue 5, pp. 466-471, Released on J-STAGE Apr. 19, 2006, Online ISSN 1881-1299, Print ISSN 0021-9592 (Year: 1984).*

International Search Report and Written Opinion for International Application No. PCT/US2017/062491, dated Feb. 14, 2018, 9 pages.

Extended European Search Report for EP Application No. 17872587.5, dated Apr. 6, 2020, 8 pages.

Neutron™ and MaxPlus™ Comparative Matrix Product Brochure, ICUmedical, (2012), http://www.icumed.com/media/155735/M1-1372%20Neutron%20vs%20MaxPlus%20Combat%20Rev.01_email.pdf, 1 page.

Bonini P. et al., "Errors in laboratory medicine," Clinical Chemistry, 48:691-698 (2002).

Extended European Search Report for EP Application No. 23156048.3, dated Aug. 7, 2023, 9 pages.

Grant M., "The effect of blood drawing techniques and equipment on the hemolysis of ED laboratory blood samples," Journal of Emergency Nursing, 29 (2):116-121 (2003).

Plebani M. et al., "Mistakes in a stat laboratory: types and frequency," Clinical Chemistry, 43(8):1348-1351 (1997).

Soderberg J. et al., "Haemolysis index—an estimate of pre-analytical quality in primary health care," Clinical Chemistry and Laboratory Medicine, 47(8):940-944 (2009).

* cited by examiner

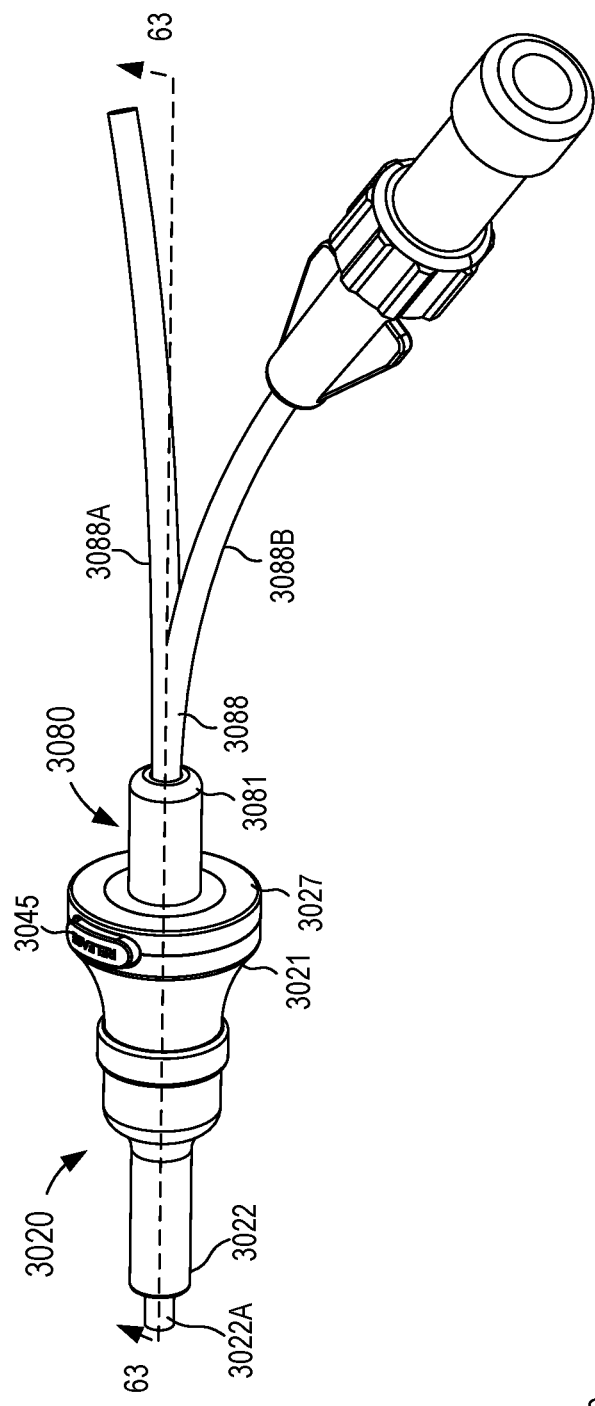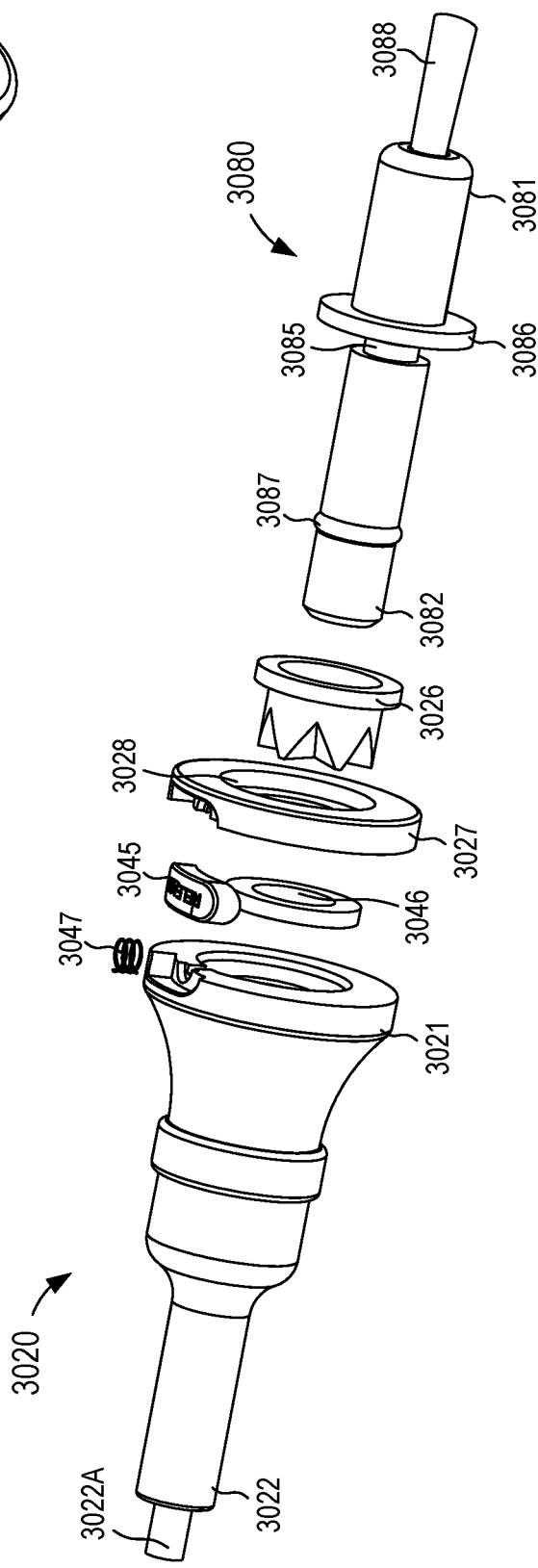
FIG. 61
FIG. 62

US 12,097,027 B2

SYSTEMS AND METHODS FOR SAMPLE COLLECTION WITH REDUCED HEMOLYSIS

CROSS-REFERENCE TO RELATED APPLICATIONS

This application claims priority to and the benefit of U.S. Provisional Patent Application Ser. No. 62/423,993 entitled, "Systems and Methods for Sample Collection with Reduced Hemolysis," filed Nov. 18, 2016, the disclosure of which is incorporated herein by reference in its entirety.

BACKGROUND

Embodiments described herein relate generally to the parenteral procurement of bodily-fluid samples, and more particularly to systems and methods for parenterally procuring bodily-fluid samples, such as blood, with reduced hemolysis.

Health care practitioners routinely draw bodily-fluids from a patient for various testing and/or donation purposes. In some instances, the process of obtaining the bodily-fluids, and in particular, blood, can result in a degradation and/or breakdown of portions and/or constituents contained in the bodily fluid. Specifically, hemolysis of red blood cells (i.e., a rupturing of the red blood cells and the release of cytoplasm) during blood draw is a known problem in the field of phlebotomy and/or medical testing. Hemolysis of blood is the most common pre-analytical source of error in clinical testing, accounting for nearly 60% of all rejected samples. Bonini P. et al., "Errors in laboratory medicine," *Clinical Chemistry,* 48, 691-698 (2002); and Plebani M. et al., "Mistakes in a stat laboratory: types and frequency," *Clinical Chemistry,* 43, 1348-1351 (1997). Moreover, hemolyzed sample rates from hospital emergency rooms can be as high as 30%. Grant M., "The effect of blood drawing techniques and equipment on the hemolysis of ED laboratory blood samples," *Journal of Emergency Nursing,* 29 (2), 116-121 (2003); and Soderberg J. et al., "Hemolysis index—an estimate of pre-analytical quality in primary health care," *Clinical Chemistry and Laboratory Medicine,* 47, 940-944 (2009). In some known blood draw systems, the arrangement and/or coupling of multiple devices to form a fluid flow path from a patient to, for example, a sample reservoir or container, shear stress exerted on or within the red blood cells, exposure time, and/or the like can lead to an increased likelihood of hemolysis within a sample volume.

Thus, a need exists for systems and methods for sample collection with reduced hemolysis.

SUMMARY

Systems and methods for parenterally procuring bodily-fluid samples, such as blood, with reduced hemolysis are described herein. In some embodiments, a collection system has a proximal end portion, a distal end portion, and an inner surface defining a fluid flow path therethrough. The distal end portion is configured to be placed in fluid communication with a patient. The proximal end portion is configured to be placed in fluid communication with a fluid reservoir. The fluid flow path defined by the inner surface is associated with at least one flow characteristic configured to limit a stress within the flow of the bodily fluid between the distal end portion and the proximal end portion.

BRIEF DESCRIPTION OF THE DRAWINGS

FIG. 61 is a perspective view of an adapter included in a bodily-fluid collection device according to another embodiment.

FIG. 62 is an exploded view of the adapter of FIG. 61.

DETAILED DESCRIPTION

Figure 1:
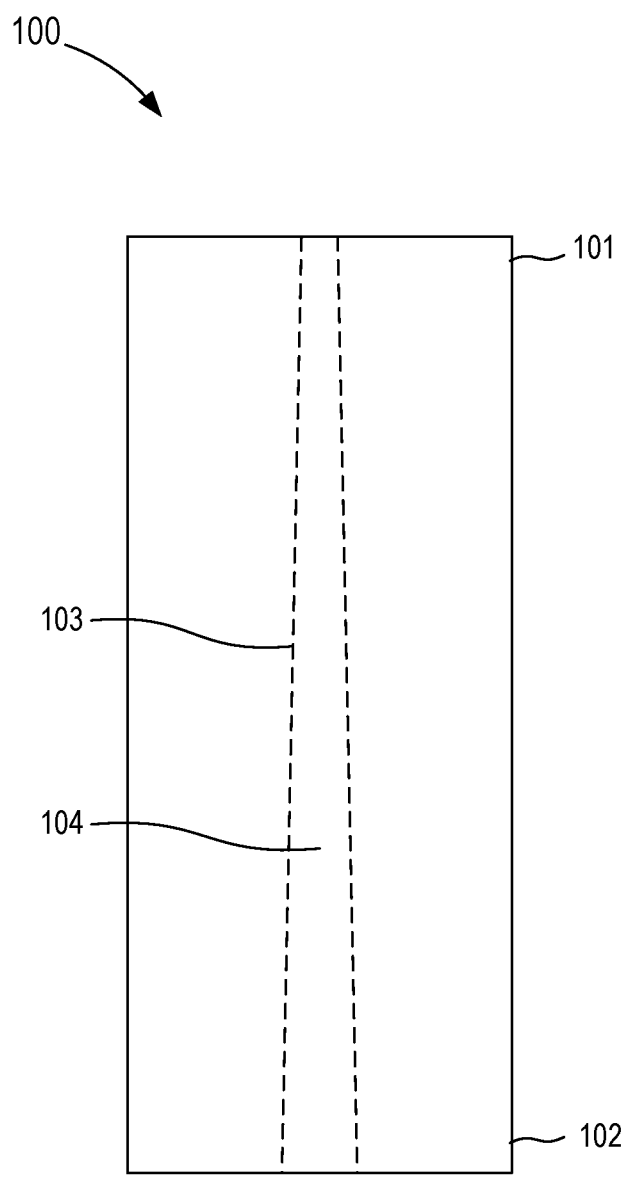
FIG. 1 is a schematic illustration of a bodily-fluid collection device according to an embodiment.

Systems and methods for parenterally procuring bodily-fluid samples, such as blood, with reduced hemolysis are described herein. In some embodiments, a device for procuring a blood sample with reduced damage from a patient to reduce distorted, adulterated, inaccurate, and/or false results (i.e., not indicative and/or representative of the actual in vivo conditions of the patients) in testing of the blood sample includes a collection member having a distal end portion and a proximal end portion. The distal end portion is configured to be placed in fluid communication with a patient. The proximal end portion is configured to be placed in fluid communication with a fluid reservoir. The collection member has an inner surface that defines a fluid flow path between the distal end portion and the proximal end portion. The inner surface is configured to influence a flow of blood flowing through the fluid flow path such that the blood flows with at least one flow characteristic configured to limit stress within the flow of the blood.

In some embodiments, a device for procuring a blood sample from a patient with reduced damage to reduce distorted, adulterated, inaccurate, and/or false results in testing of the blood sample includes a first adapter and a second adapter. The first adapter has a distal end portion and a proximal end portion. The distal end portion is configured to be placed in fluid communication with a patient. The first adapter has an inner surface extending between the distal end portion and the proximal end portion of the first adapter. The second adapter has a distal end portion and a proximal end portion. The distal end portion of the second adapter is configured to be coupled to the proximal end portion of the first adapter. The proximal end portion of the second adapter is configured to be placed in fluid communication with a fluid reservoir. The second adapter has an inner surface extending between the distal end portion and the proximal end portion of the second adapter. The inner surface of the first adapter and the inner surface of the second adapter collectively define a fluid flow path between the patient and the fluid reservoir when the second adapter is coupled to the first adapter. The coupling of the first adapter and the second adapter is such that bodily fluid flows within the fluid flow path with at least one flow characteristic configured to limit a stress within the flow of the bodily fluid.

In some embodiments, a device for procuring a blood sample from a patient with reduced damage to reduce distorted, adulterated, inaccurate, and/or false results in testing of the blood sample includes a first adapter, a second adapter, and a third adapter. The first adapter has a distal end portion and a proximal end portion. The distal end portion is configured to be placed in fluid communication with a patient. The first adapter defines a first lumen having a first diameter and extending between the proximal end portion and the distal end portion. The second adapter has a distal end portion and a proximal end portion. The proximal end portion of the second adapter is configured to be placed in fluid communication with a fluid reservoir. The second adapter defines a second lumen having a second diameter and extending between the proximal end portion and the distal end portion of the second adapter. The third adapter has a distal end portion configured to be coupled to the proximal end portion of the first adapter and a proximal end portion configured to be coupled to the distal end portion of the second adapter. The third adapter defines a third lumen extending between the proximal end portion and the distal end portion of the third adapter. The third lumen has a third diameter smaller than the first diameter and the second diameter. The first lumen, the second lumen, and the third lumen collectively define a fluid flow path between the patient and the fluid reservoir when the third adapter is coupled between the first adapter and the second adapter. The third diameter of the third lumen is operable to reduce a negative pressure within a portion of the fluid flow path defined by the first adapter.

In some embodiments, a collection system has a proximal end portion, a distal end portion, and an inner surface defining a fluid flow path therethrough. The distal end portion is configured to be placed in fluid communication with a patient. The proximal end portion is configured to be placed in fluid communication with a fluid reservoir. The fluid flow path defined by the inner surface is associated with at least one flow characteristic configured to limit a stress within the flow of the bodily fluid between the distal end portion and the proximal end portion.

As used in this specification and the appended claims, the singular forms "a," "an" and "the" include plural referents unless the context clearly dictates otherwise. Thus, for example, the term "a member" is intended to mean a single member or a combination of members, "a material" is intended to mean one or more materials, or a combination thereof.

As used herein, "bodily-fluid" can include any fluid obtained from a body of a patient, including, but not limited to, blood, cerebrospinal fluid, urine, bile, lymph, saliva, synovial fluid, serous fluid, pleural fluid, amniotic fluid, and the like, or any combination thereof. Moreover, while the embodiments and/or devices herein are specifically described as reducing, limiting, inhibiting, and/or substantially preventing hemolysis of blood withdrawn therethrough, any of the embodiments and/or devices can be used for controlling a flow of any suitable bodily-fluid (e.g., such as those listed above) when withdrawn from the body of a patient through that device.

As used herein, the term "set" can refer to multiple features or a singular feature with multiple parts. For example, when referring to set of walls, the set of walls can be considered as one wall with distinct portions, or the set of walls can be considered as multiple walls. Similarly stated, a monolithically constructed item can include a set of walls. Such a set of walls can include, for example, multiple portions that are discontinuous from each other. A set of walls can also be fabricated from multiple items that are produced separately and are later joined together (e.g., via a weld, an adhesive, or any suitable method).

As used herein, the terms "proximal" and "distal" refer to the direction closer to and away from, respectively, a user who would place the device into contact with a patient. Thus, for example, the end of a device first touching the body of the patient would be the distal end, while the opposite end of the device (e.g., the end of the device being manipulated by the user) would be the proximal end of the device.

As used herein, the terms "about," "approximately," and "substantially" when used in connection with a numerical value is intended to convey that the value so defined is nominally the value stated. Said another way, the terms about, approximately, and substantially when used in connection with a numerical value generally include the value stated plus or minus a given tolerance. For example, in some instances, a suitable tolerance can be plus or minus 10% of the value stated; thus, about 0.5 would include 0.45 and 0.55, about 10 would include 9 to 11, about 1000 would include 900 to 1100. In other instances, a suitable tolerance can be plus or minus an acceptable percentage of the last significant figure in the value stated. For example, a suitable tolerance can be plus or minus 10% of the last significant figure; thus, about 10.1 would include 10.09 and 10.11, approximately 25 would include 24.5 and 25.5. Such variance can result from manufacturing tolerances or other practical considerations (such as, for example, tolerances associated with a measuring instrument, acceptable human error, or the like).

As used herein, the term "laminar" refers to an organized and/or orderly fluid flow in parallel layers without lateral mixing, crosscurrents, eddy currents, and/or the like. More generally, the term "laminar" is intended to convey a flow of fluid that is smooth and/or free of turbulence. Moreover, the term "substantially" when used in connection with "laminar" is intended to convey that a fluid flow so defined is nominally a laminar fluid flow. As one example, a portion of a fluid transfer device defining a lumen that is described as facilitating and/or otherwise causing a "substantially laminar" fluid flow therethrough is intended to convey that, although laminar fluid flow is desirable, some non-laminar flow can occur. Such variances (e.g., turbulence or the like) can result from manufacturing tolerances, or other practical considerations. Thus, a fluid having a "substantially laminar" flow includes such non-laminar flow characteristics within an industry-accepted tolerance. For example, while it may be desirable that a bodily fluid transfer device transfer a laminar flow of blood therethrough a "substantially laminar flow" of blood can be 99% laminar, 95% laminar, 90% laminar, or any other acceptable tolerance thereof.

The embodiments described herein can be formed or constructed of one or more biocompatible materials. Examples of suitable biocompatible materials include metals, glasses, ceramics, or polymers. Examples of suitable metals include pharmaceutical grade stainless steel, gold, titanium, nickel, iron, platinum, tin, chromium, copper, and/or alloys thereof. A polymer material may be biodegradable or non-biodegradable. Examples of suitable biodegradable polymers include polylactides, polyglycolides, polylactide-co-glycolides (PLGA), polyanhydrides, polyorthoesters, polyetheresters, polycaprolactones, polyesteramides, poly(butyric acid), poly(valeric acid), polyurethanes, and/or blends and copolymers thereof. Examples of non-biodegradable polymers include nylons, polyesters, polycarbonates, polyacrylates, polymers of ethylene-vinyl acetates and other acyl substituted cellulose acetates, nondegradable polyurethanes, polystyrenes, polyvinyl chloride, polyvinyl fluoride, poly(vinyl imidazole), chlorosulphonate polyolefins, polyethylene oxide, and/or blends and copolymers thereof.

In some current phlebotomy procedures, blood is drawn from a patient using multiple components that are physically and fluidically coupled to define a fluid flow path between the patient and a collection device and/or fluid reservoir used to capture the bodily-fluid sample. In some such systems, however, the physical and/or fluidic interfaces formed between the components can result in turbulent regions and/or eddy currents within the flow of the blood, which in turn, can result in a stress within the flow that is sufficient to sheer, rupture, and/or otherwise damage the red blood cells. In addition, the process of drawing blood from a patient often involves exposing the blood to a negative pressure differential produced, for example, by placing an evacuated container (e.g., a Vacutainer™) in fluid communication with a portion of the body. In some instances, the pressure differential can increase an internal stress within a flow of blood to an extent that results in hemolysis of the red blood cells. In other instances, the pressure differential can be attributed to the physical exertion associated with a clinician actuating, for example, a syringe with a force sufficient to rupture the red blood cells during the collection process. A number of factors (for example, small veins, dehydration, veins with scar tissue, presence of sclerosis, and/or the like) can make vascular access a challenge. In such cases, excess negative pressure exerted during the collection process can result in hemolysis.

While such a negative pressure differential often facilitates withdraw of the blood, it also can produce a relatively high shear stresses within the red blood cells and/or a relatively high flow velocity of the blood through a flow path defined between the patient and the fluid reservoir (e.g., evacuated container). As a result, the red blood cells contained within the flow of blood can be damaged as the cells pass through the physical and/or fluidic interfaces formed between different components of a transfer device. In some instances, the relatively high velocity of the blood flow as the blood enters the containers can result in the blood impacting an inner surface of the container with a force sufficient to damage the red blood cells and/or other components of the blood. In addition, exposure time of a needle and/or catheter within the vein can result in hemolysis of the red blood cells.

Thus, to mitigate the risk of hemolysis of a sample volume of blood, various portions of a fluid flow path between the patient and the sample reservoir can be optimized. Such optimization can be done holistically (i.e., a system wide optimization) or done piecemeal (i.e., optimization of at least one potential source of hemolysis). By way of example, in some instances, any of the embodiments described herein, can be used independently to mitigate the risk of hemolysis at a specific point along a fluid flow path between a patient and a sample reservoir. That is to say, the embodiments described herein can be characterized by the potential source of hemolysis that the embodiments, so characterized, mitigate. For example, the embodiments described herein generally address six potential categories, portions, and/or sources of hemolysis along a fluid flow path between a patient and a fluid reservoir. Namely, the embodiments described herein can be used to mitigate the risk of hemolysis otherwise associated with (1) blood flow from, for example, a vein into a puncture member, needle, cannula, and/or the like; (2) blood flow through changing geometries and/or physical and fluidic interfaces; (3) blood flow rates and/or velocity within the fluid flow path; (4) blood flow from an adapter, puncture member, needle, cannula, and/or the like into a fluid reservoir; (5) blood flow exposure to a negative pressure differential within a fluid reservoir; and (6) blood flow through a multi-lumen adapter and/or the like.

FIG. 1 is a schematic illustration of a portion of a bodily-fluid collection device 100, according to an embodiment. Generally, the bodily-fluid collection device 100 (also referred to herein as "fluid collection device," "collection device," or "device") can be used to percutaneously withdraw bodily fluid from a patient. In some instances, the device 100 can be used to withdraw a volume of blood from a patient that is to be used as a biological sample for testing and/or assays associated with medical diagnosis and/or treatment. In other instances, the device 100 can be used to withdraw a volume of blood for collection purposes such as, for example, blood donation or the like. More particularly, the device 100 is configured to limit, inhibit, and/or substantially prevent hemolysis of at least a portion of the blood drawn therethrough, as described in further detail herein.

The device 100 has a proximal end portion 101 and a distal end portion 102 and defines a lumen 104 therethrough. More specifically, the device 100 includes an inner surface 103 that defines the lumen 104. The device 100 can be any suitable device or group of devices (e.g., a system including multiple devices). In some embodiments, for example, the device 100 can be a needle, a cannula, a trocar, a catheter, and/or the like. In such embodiments, the distal end portion 102 of the device 100 can include a sharpened, angled, or beveled edge configured to puncture the cutaneous layer of the body to place the lumen 104 in fluid communication with, for example, a vascular structure and/or the like. The proximal end portion 101 of the device 100 can be physically and/or fluidically coupled to any other suitable device such as, for example, a collection reservoir (not shown in FIG. 1). As such, the lumen 104 defined by the device 100 defines fluid pathway through which blood can flow from the patient to an intermediary collection device and/or directly to the collection reservoir.

As described above, in some embodiments, the device 100 is configured to reduce, limit, inhibit, and/or substantially prevent hemolysis of blood withdrawn from the body and through the device. For example, in embodiments in which the device 100 is a needle, cannula, catheter, and/or the like, the distal end portion 102 of the device 100 can include rounded edges and/or a substantially smooth contour. As such, the constituents of the blood (e.g., the red blood cells or "erythrocytes") can flow relatively smoothly into the lumen 104 (e.g., in response to a negative pressure differential produced, for example, by a syringe and/or an evacuated container coupled thereto) substantially without being damaged.

Moreover, in some embodiments, the shape, size, and/or contour of the inner surface 103 can selectively control the flow of blood through the device 100. By way of example, in some embodiments, the inner surface 103 can form a substantially smooth contour, which can facilitate a laminar flow of the blood therethrough. In addition, the inner surface 103 can have a contour that can selectively control an amount of negative pressure within a region of the lumen 104. For example, in some embodiments, the inner surface 103 can have a diameter that is varied along the length of the device 100. That is to say, a first portion of the inner surface 103 can have a diameter that is different from a diameter of a second portion of the inner surface 103 and thus, can reduce, constrict, limit, and/or otherwise control a flow of blood therethrough. In some such embodiments, the first portion of the inner surface 103 can be disposed between the second portion of the inner surface 103 and a third portion of the inner surface 103 having a diameter greater than or equal to the diameter of the second portion of the inner surface 103. In such embodiments, a region of the lumen 104 having a relatively larger diameter can be associated with a larger pressure than a region of the lumen 104 having a relatively smaller diameter, while conversely, a velocity associated with the region of the lumen 104 having the relatively larger diameter is less than a velocity associated with the region of the lumen having the relatively smaller diameter based on the simplified Bernoulli's Equation mathematically represented by equation 1 below:

$$P_1 + \frac{1}{2}\rho V_1^2 = P_2 + \frac{1}{2}\rho V_2^2 \qquad \text{Equation 1}$$

wherein P is pressure within the lumen, p is density of the fluid, and V is velocity of the fluid.

While described above as being a needle, catheter, cannula, trocar, and/or the like, in other embodiments, the device 100 can be any suitable component included in a fluid transfer system. For example, the device 100 can be an adapter, a locking mechanism, a cannula, a coupling mechanism, a port, an inlet, and outlet, and/or the like. By way of example, in some embodiments, the device 100 can be an adapter configured to be physically and fluidically coupled to at least one other device such as, for example, a needle. Thus, the adapter (i.e., the device 100) can have an inner surface with a contour that can control a flow of bodily-fluid therethrough. Moreover, an interface between the device 100 and the needle (and/or any other suitable device) can be arranged to reduce turbulence of a flow of bodily-fluid therebetween, as described in further detail herein.

In some embodiments, the device 100 can be coupled to a fluid reservoir or container (e.g., at the proximal end portion 101). As such, the contour of the inner surface 103 of the device 100 can control a flow of bodily-fluid therethrough (as described above), while the orientation of the device 100 relative to the fluid reservoir or container can control and/or direct the flow of bodily-fluid through the proximal end portion 101 toward an inner surface of the fluid reservoir to, for example, reduce a force associated with a portion of the flow of bodily-fluid impacting the inner surface. In some embodiments, the device 100 can be an insert or the like at least partially disposed within the fluid reservoir or container.

Although not shown in FIG. 1, in some embodiments, the device 100 can be used with (e.g., physically and fluidically coupled to) a device or mechanism configured to modulate a negative pressure within a fluid reservoir or container. For example, in some embodiments, the device 100 can be coupled to a syringe or the like configured to transition between a first configuration and a second configuration to produce a negative pressure within an inner volume. As such, a rate at which the syringe can be transitioned from the first configuration (e.g., associated with a plunger in a distal position) to the second configuration (e.g., associated with the plunger in a proximal position) can be constrained (e.g., limited, inhibited, slowed, governed, controlled, etc.), thereby reducing a negative pressure exerted through the lumen 104 of the device, as described in further detail herein.

While the device 100 is described above as including a surface, mechanism, portion, etc. configured to reduce hemolysis of a volume of blood in a mechanical manner (e.g., reducing pressure and/or turbulence within a flow path via a contour, restrictor, or the like; reducing forces associated with a portion of the volume of blood impacting a surface of a fluid reservoir via a coupling mechanism, interface, etc.; reducing damage to constituents in the volume of blood by limiting or eliminating sharp edges, corners, etc.; and/or the like), in other embodiments, the device can be configured to chemically modify one or more characteristics associated with the volume of blood. For example, in some embodiments, the inner surface 103 of the device 100 can be coated with a chemical configured to limit lysis of erythrocytes (red blood cells) by strengthening or weakening a cell wall of the erythrocytes. More specifically, in some embodiments, the device 100 can be configured to introduce a chemical into a flow of blood that can, for example, increase a rigidity of the cell wall of erythrocytes (e.g., decrease flexibility), which in turn, can reduce a likelihood of lysis of the erythrocytes (e.g., hemolysis of the blood) as the blood flows through the device 100. In other embodiments, the device 100 can be configured to introduce a chemical into a flow of blood that can, for example, decrease a rigidity of the cell wall of erythrocytes (e.g., increase flexibility), which in turn, can reduce a likelihood of lysis of the erythrocytes as the blood flows through the device 100.

While described above as coating the inner surface 103 with the chemical configured to modify a characteristic of the cell wall of the erythrocytes, in other embodiments, the device 100 can include any suitable device, mechanism, and/or method for introducing such a chemical to the volume of blood flowing therethrough. For example, the device 100 can include a chamber containing such a chemical, a baffle impregnated with such a chemical, a dispensing or dispersing device (e.g., sprayer or the like) configured to dispense a volume of such a chemical, impregnation of the chemical directly into the material used to produce the device 100 and/or any other suitable means for introducing such a chemical.

Figure 2:
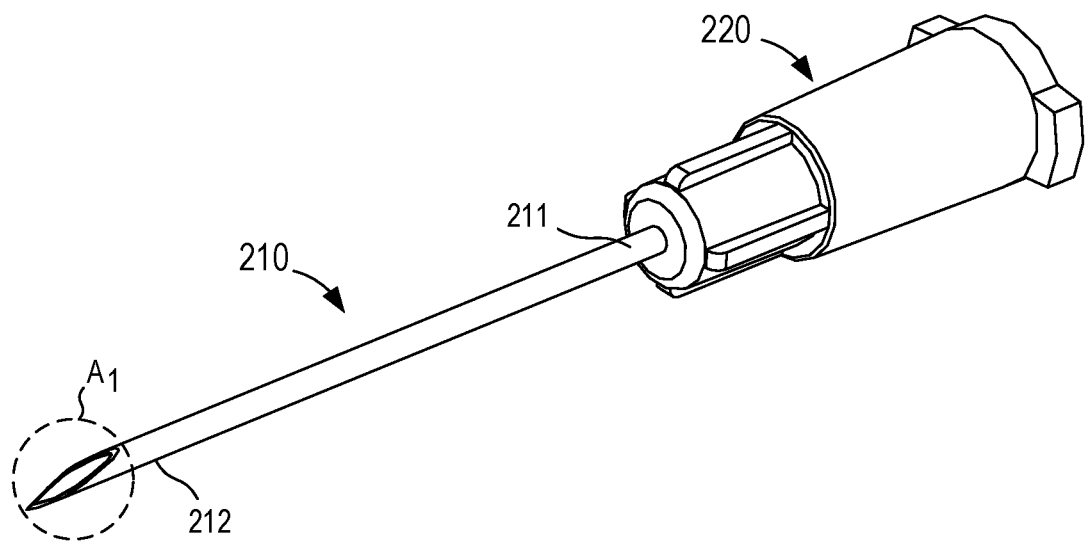
FIG. 2 is a perspective view of a needle included in a bodily-fluid collection device according to an embodiment.
Figure 3:
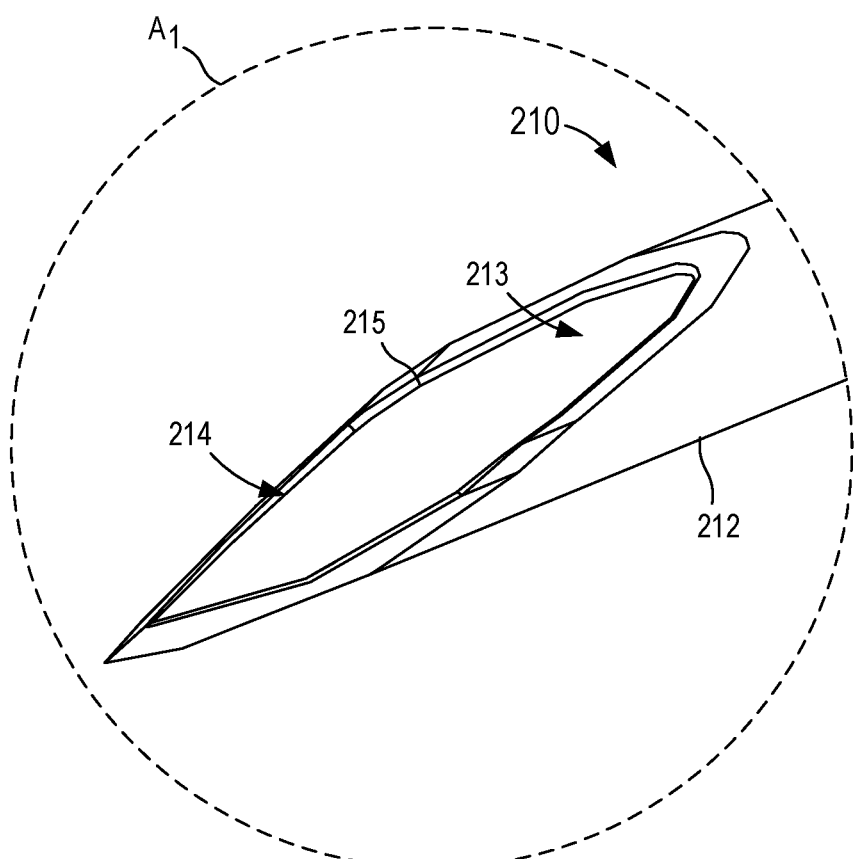
FIG. 3 is an enlarged view of a portion of the needle of FIG. 2, identified by the region $A_1$.

FIGS. 2-7 illustrate embodiments configured to mitigate the risk of hemolysis as a volume of blood flows from the patient (e.g., a vein of a patient) and into a lumen-defining device such as a needle or the like. Specifically, FIGS. 2 and 3 illustrate a puncture member 210 coupled to an adapter 220 according to an embodiment. The puncture member 210 has a proximal end portion 211 and a distal end portion 212 and defines a lumen 213 therebetween. The proximal end portion 211 of the puncture member 210 is physically and fluidically coupled to a distal end portion 222 of the adapter 220, as described above with reference to FIG. 1. More specifically, the proximal end portion 211 of the puncture member 210 is coupled to the adapter 220 such that an interface therebetween forms a substantially smooth and/or continuous surface. Said another way, the interface between the puncture member 210 and the adapter 220 can be such that a transition between the lumen 213 of the puncture member 210 and a lumen (not shown in FIGS. 2-6) defined by the adapter is substantially smooth and/or continuous (i.e., does not introduce a discontinuity such as a change in alignment and/or diameter), as described in further detail herein.

The distal end portion 212 of the puncture member 210 is configured to be inserted through the cutaneous layer of the patient to transfer fluid to and/or from the patient. For example, the distal end portion 212 can be inserted into a vein of a patient and the adapter 220 can be coupled to a fluid reservoir and/or intermediary collection device configured to receive a volume of blood from the patient via the lumen 213. More specifically, as shown in FIGS. 2 and 3, the distal end portion 212 of the puncture member 210 is sharpened, angled, and/or beveled, which facilitates the insertion of the puncture member 210 into the body. The lumen 213 of the puncture member 210 extends through the distal end portion 212, thereby defining an opening 214 that places the lumen 213 in fluid communication with, for example, a vascular structure (e.g., a vein) within which the distal end portion 212 is disposed. Furthermore, as shown in FIG. 3, a distal edge 215 of the puncture member 210 defining the opening 214 is substantially rounded, smoothed, contoured, blunted, and/or the like. In other words, the distal edge 215 defining the opening 214 forms a substantially round corner. Thus, blood drawn through the opening 214 and into the lumen 213 can flow past the distal edge 214 with reduced damage to, for example, the constituents of the blood (e.g., the erythrocytes) that would otherwise result from contact with a sharper, more abrupt, substantially orthogonal, and/or otherwise non-rounded distal edge 215.

Figure 4:
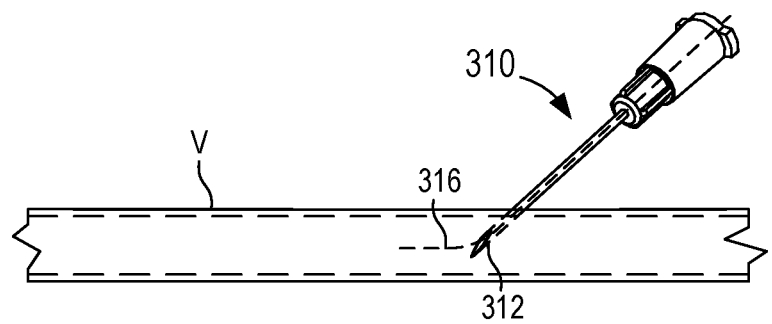
FIGS. 4-6 are illustrations of a needle used to deliver a cannula to a portion of the body according to an embodiment.
Figure 5:
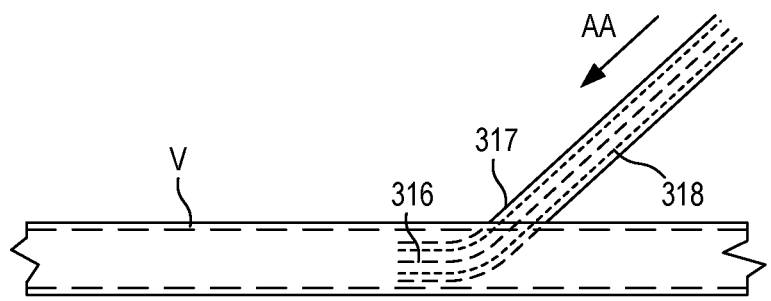
Figure 6:
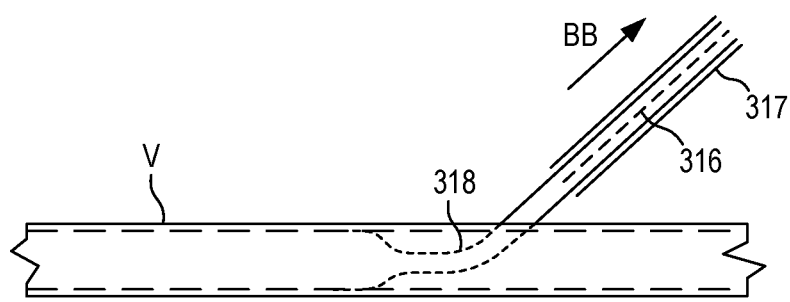

In some instances, a puncture member can be used to deliver and/or place a portion of a catheter in a desired lumen within the body of a patient. For example, as shown in FIGS. 4-6, a puncture member 310 can be used to place a stented catheter and/or the like within a vein V. The puncture member 310 can be substantially similar to the puncture members 210 and/or 310 described above and thus, the puncture member is not described in further detail herein. As shown in FIG. 4, a user (e.g., a phlebotomist, nurse, technician, physician, doctor, etc.) can manipulate a portion of the puncture member 310 (e.g., either directly or indirectly) to place at least a distal end portion 312 of the puncture member 310 within a lumen defined by the vein V. Once disposed in the vein V, a guidewire 316 can be advanced through the lumen defined by the puncture member 310, as shown in FIG. 4. With the guidewire 316 positioned within the vein V, the user can advance an introducer catheter 317 and, for example, a stented catheter 318 along the guide wire 316 to dispose a distal end portion of at least the introducer catheter 317 within the lumen of the vein V, as indicated by the arrow AA in FIG. 5. In some instances, the stented catheter 318 can be inserted into the vein V concurrently with the introducer catheter 317. In other instances, the stented catheter 318 can be advanced within the introducer catheter 317 after the distal end portion of the introducer catheter 317 is disposed in the vein 317.

With the distal end portion of the stented catheter 318 disposed in the vein V, the guidewire 316 and the introducer catheter 317 can be moved in the proximal direction (i.e., withdrawn from the vein V), as indicated by the arrow BB in FIG. 6. In some embodiments, as the introducer catheter 317 is withdrawn from the vein V, the distal end portion of the stented catheter 318 can transition from a first configuration to a second configuration. For example, the stented catheter 318 can be in a collapsed configuration (e.g., the first configuration) when disposed in the introducer catheter 317 (FIG. 5) such that a diameter of the stented catheter 318 is substantially uniform. When the introducer catheter 318 is withdrawn from the vein (FIG. 6), the distal end portion of the stented catheter 318 can expand and/or otherwise reconfigure such that a diameter of the distal end portion of the stented catheter 318 is greater than a diameter of a portion of the stented catheter 318 still disposed in the introducer catheter 317.

In some embodiments, the distal end portion of the stented catheter 318 can expand to an extent that places an outer surface of the stented catheter 318 in close proximity to or directly in temporary contact with an inner surface of the vein V defining the lumen. As such, blood can be withdrawn from the vein V into a fluid reservoir (not shown in FIGS. 4-6) via a lumen defined by the stented catheter 318. Moreover, with the distal end portion of the stented catheter 318 in close proximity to or directly in contact with the inner surface of the vein, the stented catheter 318 can inhibit, limit, and/or substantially prevent a collapse of at least a portion of the vein V (e.g., in response to a negative pressure differential between the vein V and the fluid reservoir (not shown). In some embodiments, the arrangement of at least the distal end portion of the stented catheter 318, when in the second configuration, can allow a flow of blood to enter the stented catheter 318 substantially without damaging the constituents of the blood, as described above with reference to FIGS. 2 and 3. While the puncture member 310 is described above as being retracted once the stented catheter 318 is placed in a desired position with the vein, in other embodiments, the puncture member 310 need not be retracted. As such, the stented catheter 318 can be, for example, a sleeve or the like disposed about the distal end portion 312 of the puncture member 310 to control a flow of blood entering the lumen of the puncture member 310. Moreover, as described above with reference to the puncture member 210, a surface of the puncture member 310 and/or the stented catheter 318 defining a distal opening can be substantially rounded, smoothed, contoured, blunted, and/or the like. In other words, a distal edge of the puncture member 310 and/or stented catheter 318 defining the distal opening forms a substantially round corner. Thus, blood drawn through the opening can flow past the distal edge with reduced damage to the erythrocytes that would otherwise result from contact with a sharper, more abrupt, substantially orthogonal, and/or otherwise non-rounded distal edge 215.

Figure 7:
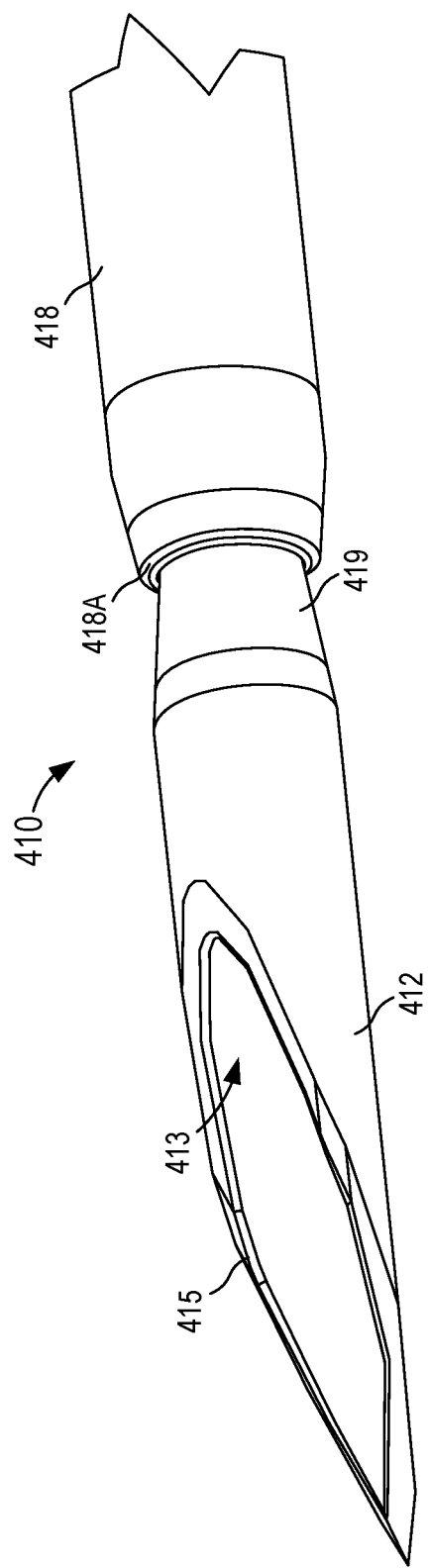
FIG. 7 is a perspective view of a portion of a needle included in a bodily-fluid collection device according to another embodiment.

While described above as placing a stented catheter, in other embodiments, a puncture member can be used to place any suitable catheter and/or cannula. For example, FIG. 7 illustrates a puncture member 410 and a catheter 418 according to another embodiment. The puncture member 410 can be used, for example, to place at least a portion of the catheter 418 within a lumen defined by the body (e.g., a vein). As shown in FIG. 7, a distal end portion 412 of the puncture member 410 can include a substantially rounded distal edge 415, as described above with reference to the puncture member 210. In this manner, a flow of blood can flow past the distal edge 415 to enter a lumen 413 defined by the puncture member 410. Similarly, the catheter 418 can include a distal edge 418A that is substantially rounded. As shown in FIG. 7, the distal end portion 412 of the puncture member 410 extends beyond the distal edge 418A of the catheter 418. In some embodiments, the distal end portion 412 of the puncture member 410 can form and/or can define a recessed portion 419 or the like that corresponds with a position at or near the distal edge 418A of the catheter 418. In this manner, when the puncture member 410 is inserted into, for example, a vein of a patient, an opening in the vein defined by the puncturing can be a diameter that is substantially the same as an outer diameter of the catheter 418. As such, the catheter 418 can be positioned within the vein without rupturing and/or otherwise dilating the opening in the vein. In some instances, once the catheter 418 is disposed in the lumen defined by the vein, the puncture member 410 can be retracted through the catheter 418 while at least a distal end portion of the catheter 418 remains within the vein. In such instances, the substantially rounded distal edge 418A can reduce and/or can substantially prevent hemolysis of a volume of blood flowing to the catheter 418, as described above with reference to the puncture member 310 in FIGS. 2 and 3.

Figure 8:
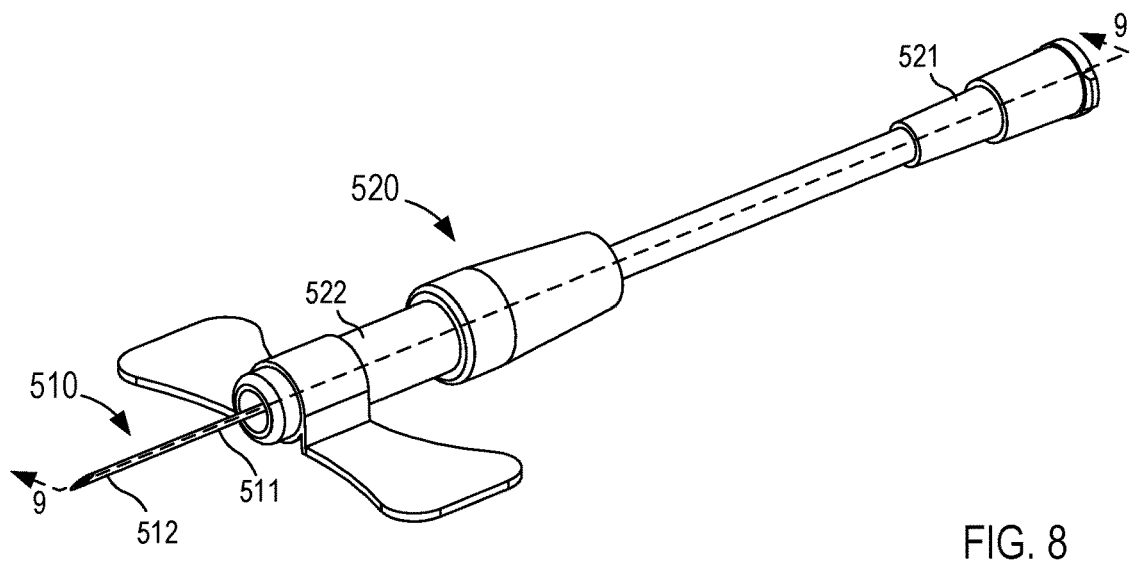
FIG. 8 is a perspective view of a portion of a bodily-fluid collection device according to an embodiment.
Figure 9:
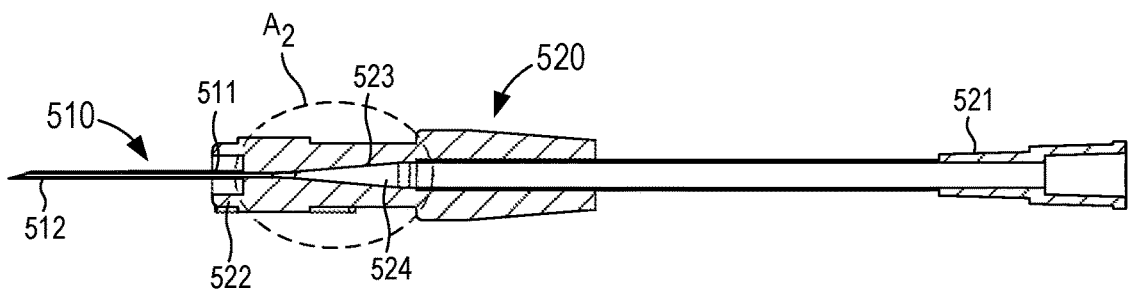
FIG. 9 is a cross-sectional view of the bodily-fluid collection device of FIG. 8, taken along the line 9-9.
Figure 10:
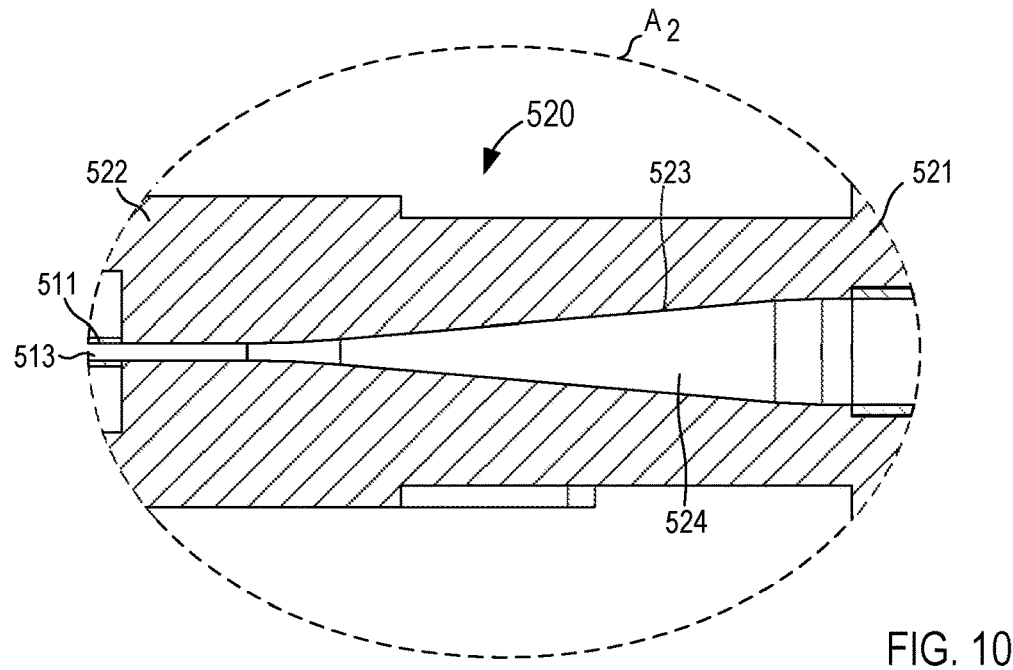
FIG. 10 is an enlarged view of a portion of the bodily-fluid collection device of FIG. 9, identified by the region $A_2$.

While the puncture members 210, 310, and 410 are particularly shown and described above, in other embodiments, any suitable puncture member can be coupled to any compatible adapter, which in turn, can place the puncture member in fluid communication with a fluid collection device. For example, FIGS. 8-17 illustrate embodiments configured to mitigate the risk of hemolysis as a volume of blood flows through changing geometries and/or physical and fluidic interfaces of one or more adapters. Specifically, FIGS. 8-10 illustrate a puncture member 510 coupled to an adapter 520, according to another embodiment. In some embodiments, the puncture member 510 and the adapter 520 can be and/or can form, for example, a butterfly needle or the like. More specifically, the puncture member 510 has a proximal end portion 511 and a distal end portion 512 and defines a lumen 513 therethrough. The proximal end portion 511 is coupled to the adapter 520, as described in further detail herein. The distal end portion 512 of the puncture member 510 can be any suitable configuration. For example, the distal end portion 512 of the catheter 510 can be substantially similar to or the same as the distal end portion 212 of the catheter 210 described above with reference to FIGS. 2 and 3. That is to say, the arrangement of the distal end portion 512 of the catheter 510 can limit and/or substantially prevent damage (e.g., hemolysis) to blood as blood flow past the distal end portion 512 and into the lumen 513.

The adapter 520 has a proximal end portion 521, a distal end portion 522, and an inner surface 523. As described above, the adapter 520 can have an overall shape substantially similar to known butterfly needles. While shown in FIG. 8 as being substantially cylindrical with varying diameters, the adapter 520 can be any suitable shape, size, or configuration such as square, rectangular, polygonal, and/or any other non-cylindrical shape. In this manner, the overall shape of the adapter 520 can facilitate the handling of the transfer device 520 by including similar geometric features as known butterfly needles. The distal end portion 522 of the adapter 520 is physically and fluidically coupled to the proximal end portion 511 of the puncture member 510, as described in further detail herein. The proximal end portion 521 of the adapter 520 can be any suitable configuration. In some embodiments, the proximal end portion 521 can be a port and/or a portion of a locking mechanism. For example, in this embodiment, the proximal end portion 521 of the adapter 520 is a locking mechanism configured as a male portion of a Luer Lok®. Moreover, in this embodiment, such a locking mechanism is disposed at a proximal end portion of a cannula configured to extend between the proximal end portion 521 and the distal end portion 522 of the adapter 520. In other embodiments, the adapter 520 is monolithically formed without a cannula between the proximal end portion 521 and the distal end portion 522. Although the proximal end portion 521 is described as including a locking mechanism, in other embodiments, the proximal end portion 521 can be any suitable configuration configured to interface with any suitable device such that blood flows in a substantially laminar, smooth, and/or non-turbulent flow between the adapter 520 and the device.

As shown in FIGS. 9 and 10, the inner surface 523 of the adapter 520 defines a lumen 524 extending through the proximal end portion 521 and the distal end portion 522. In some embodiments, the arrangement of the inner surface 523 can reduce, inhibit, and/or substantially prevent, for example, hemolysis of a volume of blood flowing within the lumen 524. More specifically, as shown in FIG. 10, the distal end portion 522 of the adapter 520 is coupled to the proximal end portion 511 of the puncture member 510 such that the lumen 513 of the puncture member 510 is substantially aligned with and substantially the same diameter as the lumen 524 of the adapter 520. That is to say, the proximal end portion 511 of the puncture member 510 is coupled to the distal end portion 522 of the adapter 520 such that a substantially smooth and/or continuous transition is defined between the lumen 513 of the puncture member 510 and the lumen 524 of the adapter 520. Similarly, in embodiments including the cannula extending between the end portions, a distal end portion of the cannula can be coupled to the distal end portion 522 of the adapter 520 in such a manner as to define a substantially smooth transition therebetween.

In addition, the inner surface 523 of the adapter 520 defines a tapered portion that extends between the puncture member 510 and the cannula. Expanding further, a first portion of the inner surface 523 (e.g., a more proximal portion) defines a first diameter that is substantially the same as an inner diameter defined by the cannula, while a second portion of the inner surface (e.g., a more distal portion) defines a second diameter, smaller than the first diameter, that is substantially the same as an inner diameter defined by the lumen 513 of the puncture member 510. As shown in FIG. 10, the tapered portion can form a substantially smooth transition between, for example, the first diameter and the second diameter. In some instances, such a smooth transition, for example, from the first diameter to the second diameter can facilitate, produce, encourage, and/or force a substantially laminar flow (e.g., consistent, uniform, non-turbulent, uninterrupted, smooth, etc.) of a volume of bodily-fluid (e.g., blood) through the lumen 524. Moreover, the smooth or substantially uniform transitions between the puncture member 510 and the adapter 520 and/or the smooth or substantially uniform transitions between the various components of the adapter 520 can reduce eddy currents (i.e., circulating currents often resulting from a discontinuity) or the like within the flow of blood. Thus, when the distal end portion 512 of the puncture member 510 is disposed in a vein or the like and the proximal end portion 521 (e.g., a locking mechanism) is physically and fluidically coupled to a fluid reservoir, a volume of blood can flow within the lumens 513 and 524 from the patient to the fluid reservoir with reduced damage to the constituents of the blood (e.g., hemolysis of the erythrocytes) that might otherwise occur as a result of misaligned interfaces and/or discontinuities; abrupt changes in diameter; turbulence and/or eddy currents within a flow of blood therethrough; and/or the like.

Figure 11:
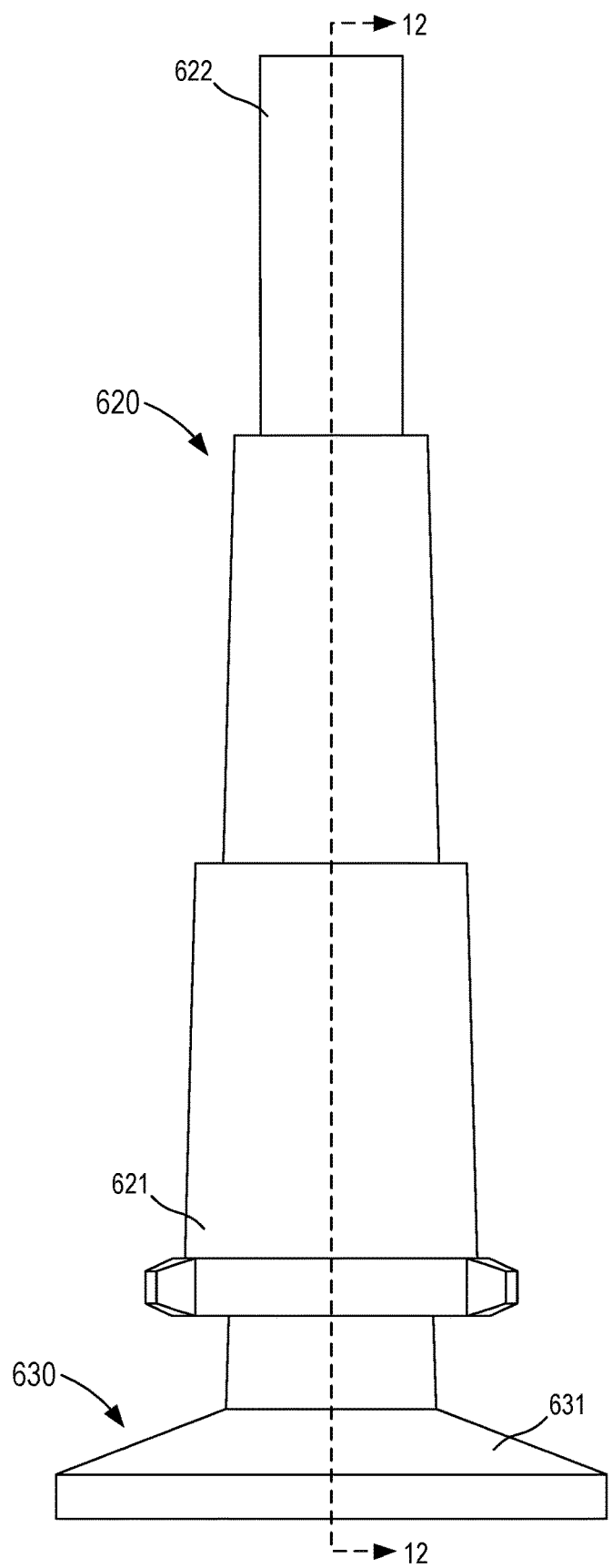
FIG. 11 is a front view of a portion of a bodily-fluid collection device according to an embodiment.
Figure 12:
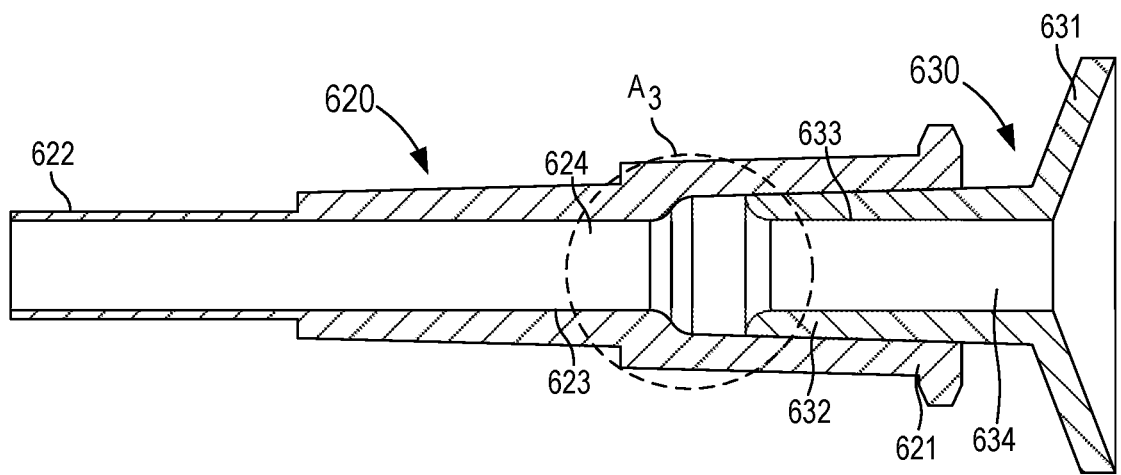
FIG. 12 is a cross-sectional view of the portion of the bodily-fluid collection device of FIG. 11, taken along the line 12-12.
Figure 13:
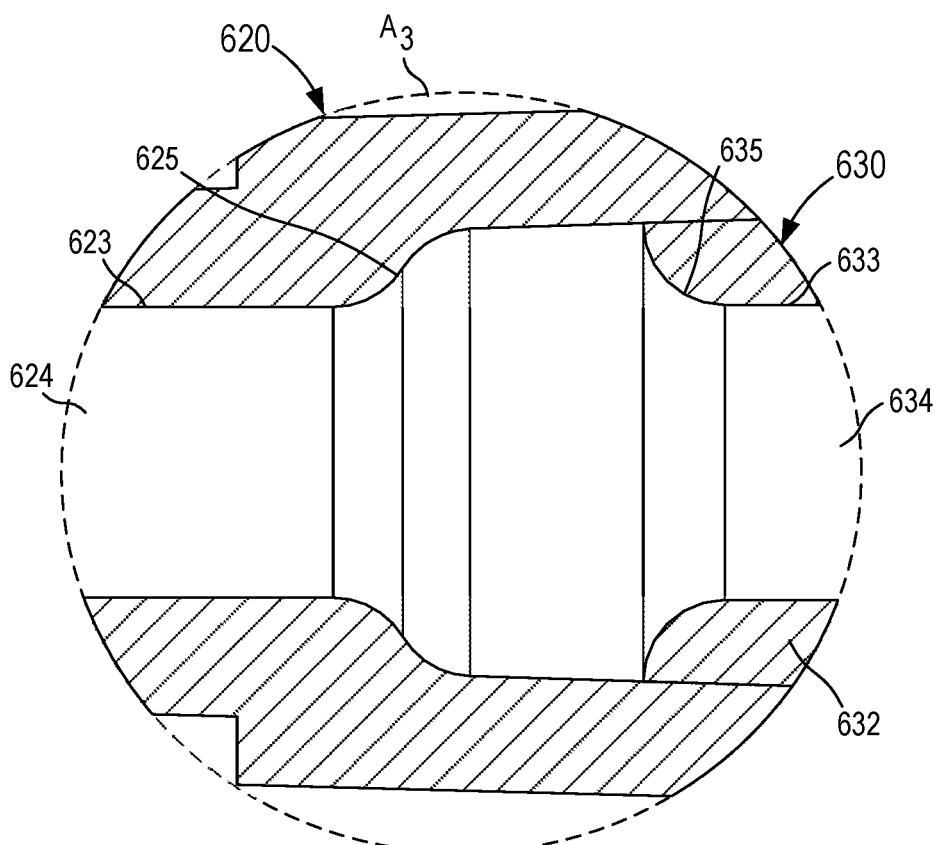
FIG. 13 is an enlarged view of a portion of the bodily-fluid collection device of FIG. 12, identified by the region $A_3$.

While the adapter 520 is particularly shown and described above with reference to FIGS. 8-10, in other embodiments, an adapter can be any suitable configuration and can be arranged within a system of components to form a physical and/or fluidic interface therebetween. For example, FIGS. 11-13 illustrate a first adapter 620 coupled to a second adapter 630 according to an embodiment. The first adapter 620 has a proximal end portion 621, a distal end portion 622 and an inner surface 623. The inner surface 623 of the first adapter 620 defines a lumen 624 extending through its proximal end portion 621 and its distal end portion 622.

As shown in FIGS. 12 and 13, the inner surface 623 of the first adapter 620 includes and/or otherwise forms a shoulder 625. More specifically, the shoulder 625 formed by the inner surface 623 is associated with a change in diameter of the inner surface 623. As shown in FIG. 13, the shoulder 625 forms a substantially annular discontinuity that has substantially rounded corners or edges. In this manner, the transition from a diameter of the inner surface 623 proximal to the shoulder 625 to a diameter of the inner surface distal to the shoulder 625 can be relatively smooth rather than forming a relatively sharp, abrupt, and/or orthogonal corner (e.g., shoulder). As such, the arrangement of the shoulder 625 can limit, inhibit, and/or substantially prevent hemolysis of blood as the blood flows within the lumen 624 past the shoulder 625.

The second adapter 630 has a proximal end portion 631, a distal end portion 632, and an inner surface 633. The inner surface 633 of the second adapter 630 defines a lumen 624 extending through its proximal end portion 631 and its distal end portion 632. As shown in FIGS. 11-13, a portion of the second adapter 630 can be inserted into a portion of the lumen 624 defined by the first adapter 620 to couple the second adapter 630 to the first adapter 620. In some embodiments, the first adapter 620 and the second adapter 630 can form a friction fit and/or the like, which in turn, can define a substantially fluid tight seal therebetween. Thus, the second adapter 630 can be inserted into the first adapter 620 to couple the second adapter 630 thereto.

Similarly, the distal end portion 632 of the second adapter 630 is configured to reduce, limit, and/or substantially prevent hemolysis of blood as the blood flow therethrough. Specifically, as shown in FIG. 13, a distal most surface of the second adapter 630 and the inner surface 633 of the second adapter 630 form a rounded corner 635 and/or smooth transition therebetween. The rounded corner 635 formed by the second adapter 630 defines a relatively smooth transition from an outer diameter of the second adapter 630 (e.g., at the distal end) to an inner diameter of the second adapter 630 (e.g., at the distal end) rather than forming a relatively sharp, abrupt, and/or orthogonal corner. In some embodiments, a radius of curvature associated with the rounded corner 635 of the second adapter 630 can be substantially similar to a radius of curvature associated with the shoulder 625 of the first adapter 620. Thus, when the second adapter 630 is disposed within the first adapter 620, a volume of bodily fluid (e.g., blood) can flow through the lumen 624 of the first adapter 620 and the lumen 634 of the second adapter 630 to be disposed within a fluid reservoir or the like. Moreover, the arrangement of the shoulder 625 of the first adapter 620 and the rounded corner 635 of the second adapter 630 can, for example, reduce, limit, and/or substantially prevent hemolysis of blood flowing therethrough that might otherwise result from contact substantially abrupt, sharp, and/or orthogonal corners or the like. In addition, the arrangement of the shoulder 625 of the first adapter 620 and the rounded corner 635 of the second adapter 630 can facilitate, produce, encourage, and/or otherwise result in a substantially laminar flow through the lumens 624 and 634, respectively (e.g., with little turbulence, eddy currents, etc.).

Figure 14:
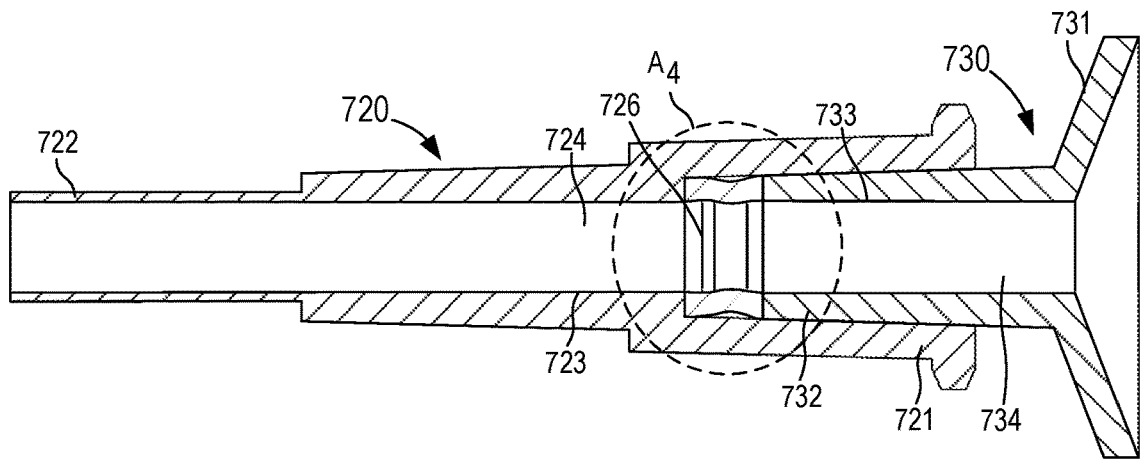
FIG. 14 is a cross-sectional view of a portion of a bodily-fluid collection device according to another embodiment.
Figure 15:
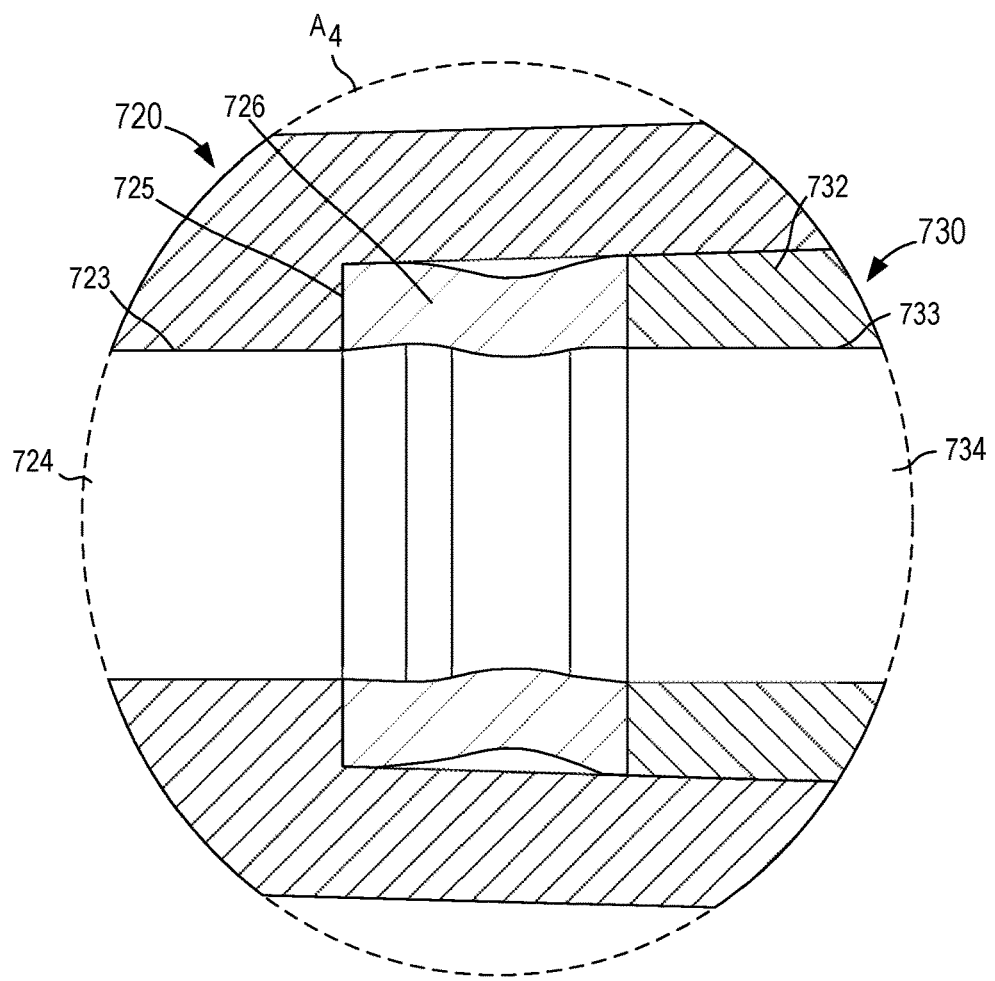
FIG. 15 is an enlarged view of a portion of the bodily-fluid collection device of FIG. 14, identified by the region $A_4$.

Although the first adapter 620 and the second adapter 630 are shown in FIGS. 11-13 as each forming substantially rounded corners and/or shoulders, in other embodiments, a first adapter and a second adapter can be coupled together to form an interface therebetween having any suitable arrangement and/or configuration. For example, FIGS. 14 and 15 illustrate a first adapter 720 coupled to a second adapter 730 according to another embodiment. The first adapter 720 has a proximal end portion 721, a distal end portion 722 and an inner surface 723. The inner surface 723 of the first adapter 720 defines a lumen 724 extending through its proximal end portion 721 and its distal end portion 722. Furthermore, the inner surface 723 includes and/or otherwise forms a shoulder 725. In this embodiment, the shoulder 725 is associated with a change in diameter of the inner surface 723. As shown in FIG. 15, the shoulder 725 forms a substantially annular discontinuity with a substantially orthogonal corner. Said another way, the shoulder 725 has a substantially non-rounded corner (e.g., has no radius of curvature or a nominal radius of curvature) that defines an edge or the like.

The second adapter 730 has a proximal end portion 731, a distal end portion 732, and an inner surface 733. The inner surface 733 of the second adapter 730 defines a lumen 724 extending through its proximal end portion 731 and its distal end portion 732. As shown in FIGS. 14 and 15, a portion of the second adapter 730 can be inserted into a portion of the lumen 724 defined by the first adapter 720 to couple the second adapter 730 to the first adapter 720. As shown in FIG. 14, the distal most surface of the second adapter 730 and the inner surface 733 of the second adapter 730 form a substantially orthogonal corner 735 (e.g., a substantially non-rounded corner, as described above). In some embodiments, the first adapter 720 and the second adapter 730 can be substantially similar to known adapters (e.g., each adapter forms relatively abrupt and/or substantially orthogonal corners and/or edges).

While such corners, discontinuities, and/or edges are described above as a potential source of blood hemolyzation, in this embodiment, a gasket 726 is disposed between and in contact with the shoulder 725 of the first adapter 720 and the distal surface of the second adapter 730, as shown in FIG. 15. The gasket 726 can be, for example, an elastomeric gasket and/or the like that is in contact with the distal surface of the second adapter 730 and the shoulder 725 of the first adapter 720 to define a substantially fluid tight seal therebetween. Moreover, the gasket 726 defines an opening and/or lumen therethrough that can have a size and/or diameter substantially similar to the size and/or diameter of the lumens 724 and 734. Thus, the arrangement of the gasket 726 can reduce a magnitude of the discontinuities formed by the shoulder 725 of the first adapter 720 and the distal end of the second adapter 730. As a result, the gasket 726 disposed between the shoulder 725 of the first adapter 720 and the distal surface of the second adapter 730 can, for example, reduce, limit, and/or substantially prevent hemolysis of blood flowing therethrough that might otherwise result from relatively large changes and/or discontinuities in the diameters of the inner surfaces 723 and 733, respectively. In addition, the gasket 726 can facilitate, produce, encourage, and/or otherwise result in a substantially laminar flow of fluid through the lumens 724 and 734, respectively (i.e., with little to no turbulence, eddy currents, etc.).

In some embodiments, the gasket 726 can be configured to restrict, limit, reduce, and/or otherwise control a flow of blood and/or a pressure exerted therethrough. For example, while the gasket 726 is described above as having substantially the same size and/or diameter as the lumens 724 and 734, in other embodiments, the gasket 726 can have a size and/or diameter that is greater than or less than the diameter of the lumens 724 and 734. Specifically, in some embodiments, the size and/or diameter of the gasket 726 can be less than the diameter of the lumens 724 and 734 and, as such, the gasket 726 can restrict, constrict, reduce, limit, and/or otherwise control a flow of blood therethrough. In some embodiments, such a reduction and/or restriction of the blood flowing through the gasket 726 can reduce a likelihood of hemolysis of the blood resulting from, for example, a flow rate and/or a large pressure differential between a volume having a relatively high pressure disposed on a first side of the gasket 726 and a volume having a relatively low pressure disposed on a second side of the gasket 726.

Figure 16:
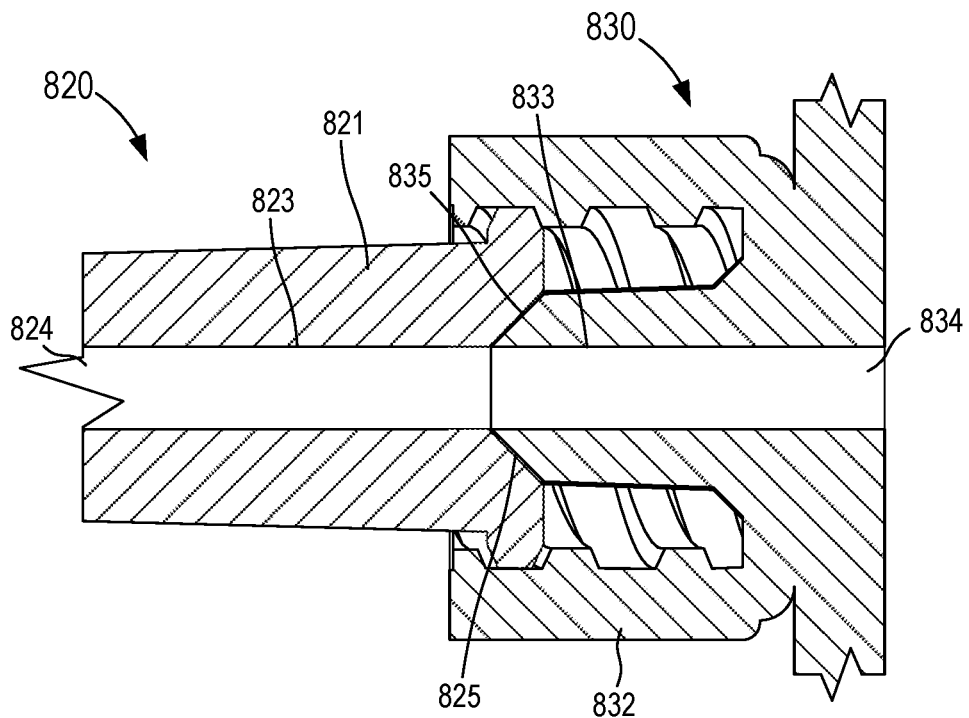
FIG. 16 is a cross-sectional view of a portion of a bodily-fluid collection device according to another embodiment.

FIG. 16 illustrates a portion of a first adapter 820 coupled to a portion of a second adapter 830 according to another embodiment. The first adapter 820 has a proximal end portion 821 configured to be coupled to a distal end portion 832 of the second adapter 830, as described in further detail herein. Although only the proximal end portion 821 of the first adapter 820 is shown in FIG. 16, the first adapter 820 can be similar in size and/or shape as the first adapters 620 and/or 720, unless otherwise expressed. The first adapter 820 includes an inner surface 823 that defines a lumen 824 extending through at least its proximal end portion 821. As shown in FIG. 16, the inner surface 823 of the first adapter 820 includes and/or otherwise forms a shoulder 825. The shoulder 825 formed by the inner surface 823 is associated with a change in diameter of the inner surface 823. More specifically, the shoulder 825 is associated with and/or forms a tapered or chamfered portion of the inner surface 823, as described in further detail herein.

Although only the distal end portion 832 of the second adapter 830 is shown in FIG. 16, the second adapter 830 can be any suitable shape, size, or configuration. For example, the distal end portion 832 of the second adapter 830 can form and/or can include a locking mechanism or the like while a proximal end portion (not shown in FIG. 16) can be coupled to and/or can form any suitable portion of a fluid collection device such as, for example, a fluid reservoir, a conduit, a flow control mechanism, and/or the like. In this embodiment, the distal end portion 832 of the second adapter 830 includes and/or forms a locking mechanism configured to form a threaded coupling with, for example, the proximal end portion 821 of the first adapter 820. In other embodiments, the distal end portion 832 of the second adapter 830 can be any suitable configuration.

As shown in FIG. 16, the second adapter 830 includes an inner surface 833 that defines a lumen 834 extending through at least its distal end portion 832. Moreover, the distal end portion 832 of the second adapter 830 includes and/or forms a distal surface 835 that is substantially tapered or chamfered. In some embodiments, the distal surface 835 of the second adapter 830 can have a size, shape, angle, etc. that substantially corresponds with the shoulder 825 defined by the first adapter 820. Thus, when the first adapter 820 is coupled to the second adapter 830 (e.g., via a threaded coupling or the like), the distal surface 835 of the second adapter 830 can be brought into contact with the shoulder 825 of the first adapter 820. Moreover, the arrangement of the first adapter 820 and the second adapter 830 is such that when the distal surface 835 of the second adapter 830 is placed in contact with the shoulder 825 of the first adapter 820, the inner surfaces 833 and 823, respectively, are brought into alignment, as shown in FIG. 16. In this manner, the inner surfaces 823 and 833 can form a substantially continuous surface having, for example, a substantially constant diameter. Thus, by reducing and/or substantially eliminating a discontinuity otherwise associated with the physical and fluidic coupling of the first adapter 820 and the second adapter 830, blood can flow within the lumens 824 and 834 of the adapters 820 and 830, respectively, with little or substantially no hemolysis of the blood flowing therethrough.

Although the inner surfaces 823 and 833 of the first adapter 820 and the second adapter 830, respectively, are described above as having a substantially constant diameter, in other embodiments, a diameter of each inner surface 823 and 833 can be varied. Such arrangement, however, is such that the inner surfaces 823 and 833 form a substantially smooth transition between, for example, a smaller diameter and a larger diameter. Thus, the substantially smooth transition in the diameters of the inner surfaces 823 and 833 can still facilitate a substantially laminar flow therethrough, which in some instances, can limit and/or substantially prevent hemolysis of blood flowing from the first adapter 820 and through the second adapter 830.

Figure 17:
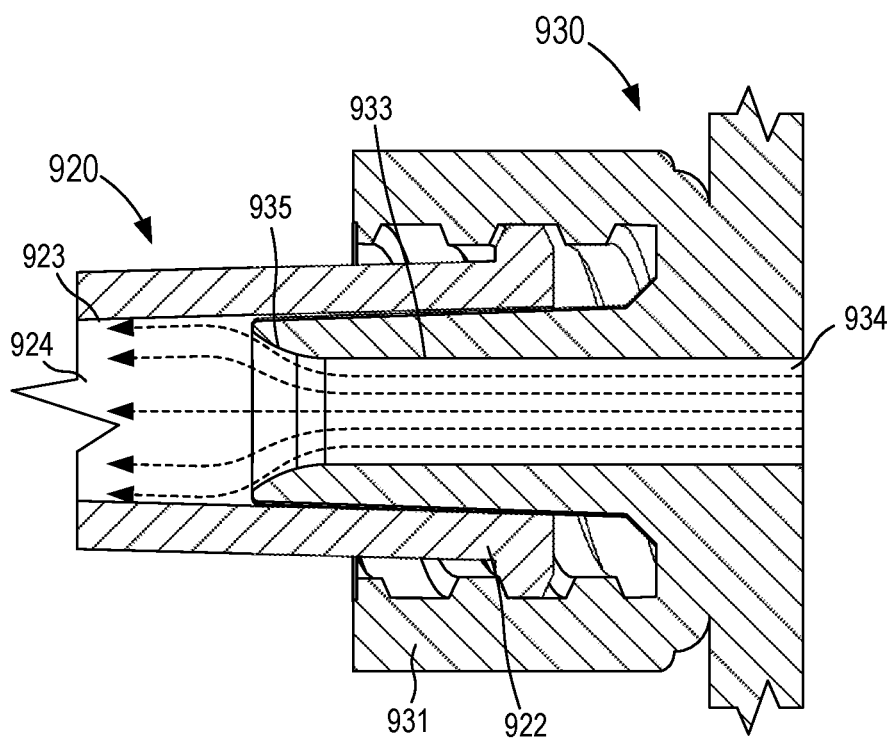
FIG. 17 is a cross-sectional view of a portion of a bodily-fluid collection device according to another embodiment.

While the flow of bodily fluid (i.e., blood) is described above as first flowing through the first adapter 820 and then flowing through the second adapter 930, in other embodiments, the flow through a set of adapters can be reversed. For example, FIG. 17 illustrates a first adapter 920 and a second adapter 930 according to another embodiment. The first adapter 920 has a distal end portion 922 configured to be coupled to a proximal end portion 931 of the second adapter 930, as described in further detail herein. Although only the distal end portion 922 of the first adapter 920 is shown in FIG. 17, the first adapter 920 can be similar in size and/or shape as the first adapters 620 and/or 720, unless otherwise expressed. The first adapter 920 includes an inner surface 923 that defines a lumen 924 extending through at least its distal end portion 922. As shown in FIG. 17, a portion of the second adapter 930 is inserted into the lumen 924, as described in further detail herein.

Although only the proximal end portion 931 of the second adapter 930 is shown in FIG. 17, the second adapter 930 can be any suitable shape, size, or configuration. For example, the proximal end portion 931 of the second adapter 930 can form and/or can include a locking mechanism or the like while a proximal end portion (not shown in FIG. 17) can be coupled to and/or can form any suitable portion of a fluid collection device such as, for example, a puncture member, a needle, a conduit, a flow control mechanism, and/or the like. In this embodiment, the proximal end portion 931 of the second adapter 930 includes and/or forms a locking mechanism configured to form a threaded coupling with, for example, the distal end portion 922 of the first adapter 920. In other embodiments, the proximal end portion 931 of the second adapter 930 can be any suitable configuration.

As shown in FIG. 17, the second adapter 930 includes an inner surface 933 that defines a lumen 934 extending through at least its proximal end portion 931. Moreover, a region of the proximal end portion 931 of the second adapter 930 is disposed within the lumen 924 of the first adapter 920. For example, the inner surface 923 of the first adapter 920 has a diameter that corresponds to an outer diameter associated with the region of the proximal end portion 931 of the second adapter 930. Thus, as shown in FIG. 17, the diameter defined by the inner surface 923 of the first adapter 920 is greater than a diameter defined by the inner surface 933 of the second adapter 930, as described in further detail herein.

The proximal end portion 931 of the second adapter 930 includes and/or forms a proximal surface 935 with a substantially rounded corner and/or smooth transition. For example, the proximal surface 935 formed by the second adapter 930 defines a relatively smooth transition from an inner diameter of the second adapter 930 (e.g., defined by the inner surface 933) to an outer diameter of the second adapter 930 (e.g., at the distal end) rather than forming a relatively sharp, abrupt, and/or orthogonal corner. When a portion of the second adapter 930 is disposed within the lumen 923 of the first adapter 920, a volume of bodily fluid (e.g., blood) can flow through the lumen 934 of the second adapter 930 and into the lumen 924 of the first adapter 920. Thus, the arrangement of the proximal surface 935 of the second adapter 930 can, for example, facilitate, produce, encourage, and/or otherwise result in a substantially laminar flow of a volume of bodily-fluid (i.e., blood) as the volume flows from the lumen 934 of the second adapter 930 into the lumen 924 of the first adapter 920. Specifically, the proximal surface 935 of the second adapter 930 allows for a gradual transition from the diameter associated with the lumen 934 of the second adapter 930 (i.e., the smaller diameter) to the diameter associated with the lumen 924 of the first adapter 920 (i.e., the larger diameter). Such a smooth transition can, for example, reduce eddy currents and/or other forms of turbulence that can otherwise result from a substantially abrupt change in diameter or the like. Thus, the arrangement of the first adapter 920 and the second adapter 930 can allow a volume of blood to expand as the flow of blood exits the lumen 934 of the second adapter 930, which in some instances, can reduce, limit, and/or substantially prevent hemolysis of blood flowing therethrough.

Figure 18:
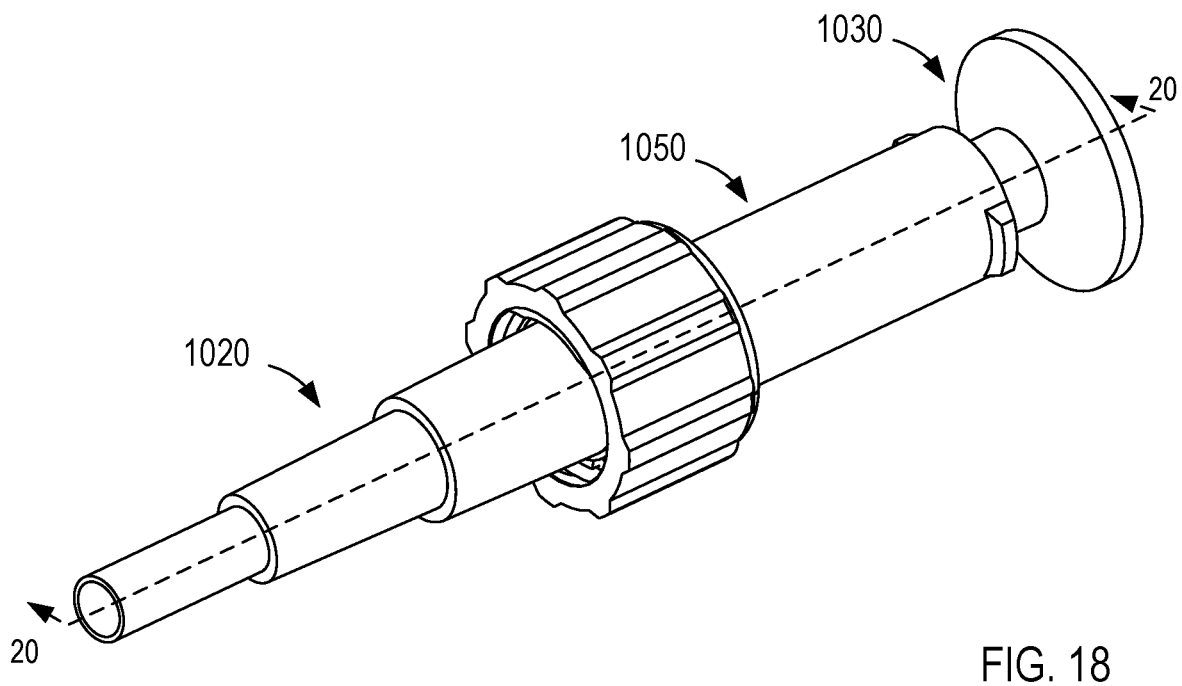
FIG. 18 is a perspective view of a portion of a bodily-fluid collection device according to an embodiment.
Figure 19:
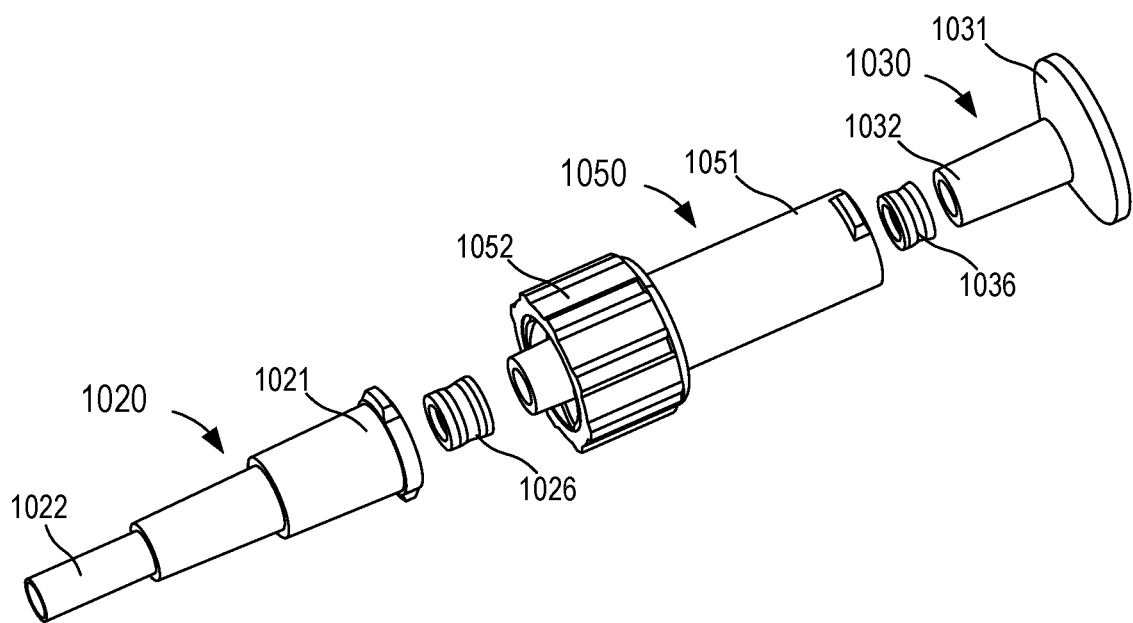
FIG. 19 is an exploded view of the portion of the bodily-fluid collection device of FIG. 18.
Figure 20:
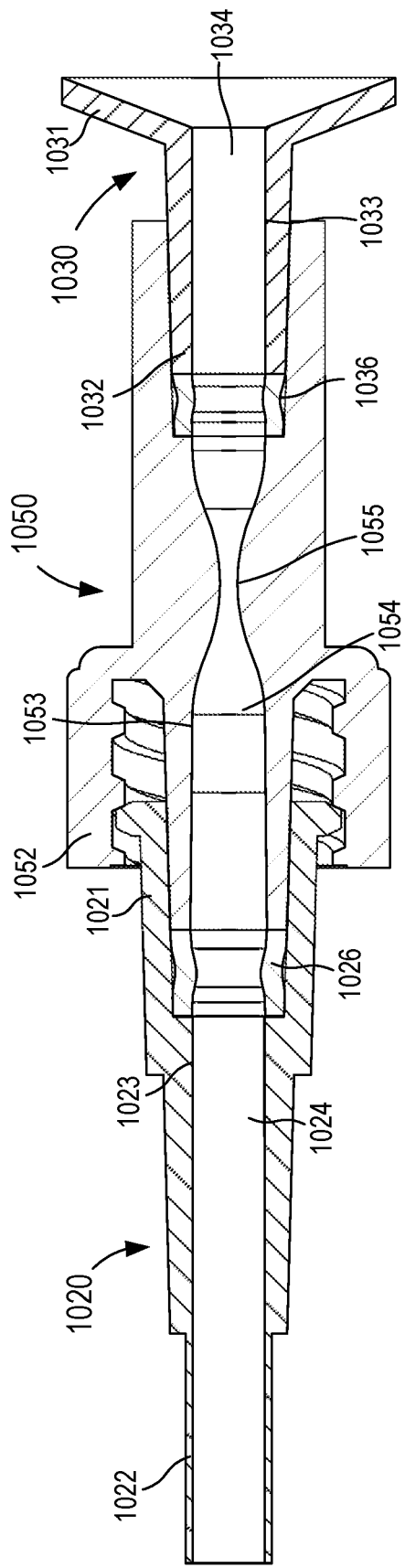
FIG. 20 is a cross-sectional view of the portion of the bodily-fluid collection device of FIG. 18, taken along the line 20-20.
Figure 21:
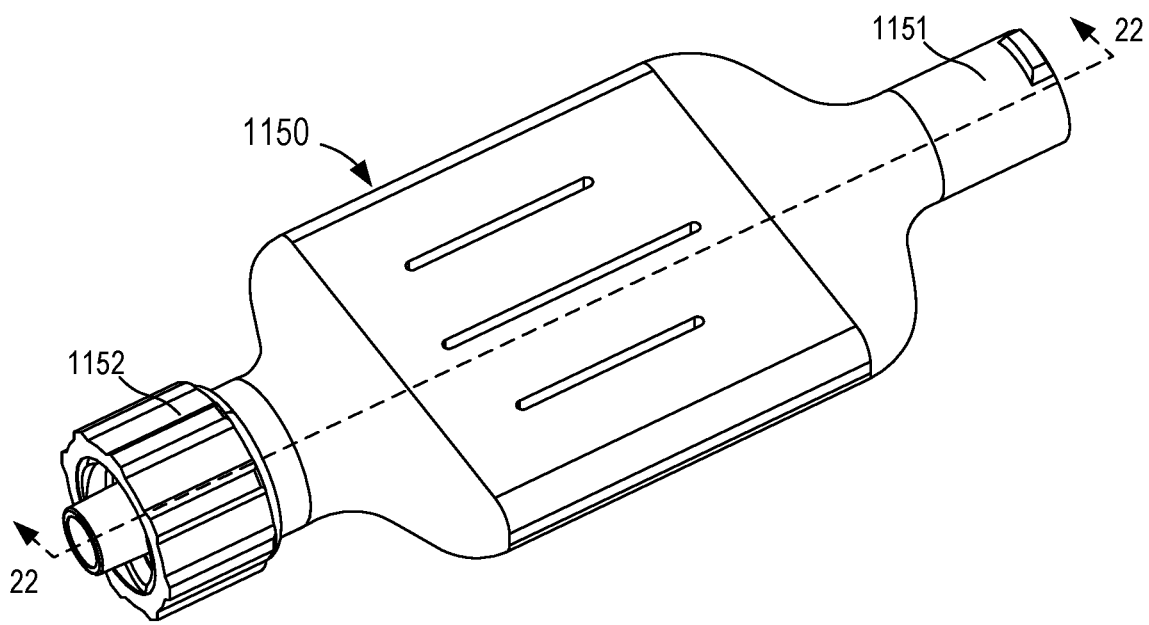
FIG. 21 is a perspective view of a restrictor included in a bodily-fluid collection device according to an embodiment.

While the first adapters 620, 720, 820, and 920 are shown and described above as receiving and/or otherwise being directly coupled to the second adapters 630, 730, 830, and 930, respectively, in other embodiments, a first adapter can be indirectly coupled to a second adapter via an intervening structure. In such embodiments, the intervening structure can define a lumen that can place the first adapter in fluid communication with the second adapter. Moreover, the intervening structure can limit, modulate, and/or control a flow rate of a volume of fluid (i.e., blood) therethrough. For example, FIGS. 18-26 illustrate embodiments configured to mitigate the risk of hemolysis otherwise associated with a relatively high flow rate and/or velocity along a fluid flow path that exceeds known shear force and exposure time limits that can rupture red blood cells. Specifically, FIGS. 18-20 illustrate a first adapter 1020 indirectly coupled to a second adapter 1030 via a restrictor 1050, according to an embodiment. The first adapter 1020 includes a proximal end portion 1021, a distal end portion 1022, and an inner surface 1023. The inner surface 1023 defines a lumen 1024 extending through the proximal end portion 1021 and the distal end portion 1022 (see e.g., FIG. 20). In some embodiments, the first adapter 1020 can be substantially similar to and/or the same as the first adapter 720 described above with reference to FIGS. 14 and 15. Thus, aspects of the first adapter 1020 are not described in further detail herein.

The second adapter 1030 has a proximal end portion 1031, a distal end portion 1032, and an inner surface 1033. The inner surface 1033 of the second adapter 1030 defines a lumen 1024 extending through its proximal end portion 1031 and its distal end portion 1032 (see e.g., FIG. 20). In some embodiments, the second adapter 1030 can be substantially similar to and/or the same as the second adapter 730 described above with reference to FIGS. 14 and 15. Thus, aspects of the second adapter 1030 are not described in further detail herein.

The restrictor 1050 has a proximal end portion 1051, a distal end portion 1052, and an inner surface 1053. The inner surface 1053 of the restrictor 1050 defines a lumen 1054 extending through its proximal end portion 1051 and its distal end portion 1052 (see e.g., FIG. 20). In this embodiment, the restrictor 1050 is coupled between the first adapter 1020 and the second adapter 1030 to define a fluid pathway therebetween (e.g., via the lumen 1054). More specifically, the restrictor 1050 can include any suitable interface, locking mechanism, surface, etc. at or near the proximal end portion 1051 and the distal end portion 1052 configured to couple the restrictor 1050 to the first adapter 1020 or the second adapter 1030. As shown in FIGS. 18-20, the restrictor 1050 includes a locking mechanism or the like at its distal end portion 1052 that is configured to couple the distal end portion 1052 of the restrictor 1050 to the proximal end portion 1021 of the first adapter 1020. For example, in some embodiments, the distal end portion 1052 of the restrictor 1050 can include a threaded female Luer Lok® configured to form a threaded coupling with a corresponding threaded male Luer Lok® of the first adapter 1020, as shown in FIG. 20.

As shown in FIGS. 19 and 20, the proximal end portion 1051 of the restrictor 1050 receives the second adapter 1030. For example, as described above with reference to the first adapter 620 and the second adapter 630 in FIGS. 11-13, a portion of the second adapter 1030 is inserted through the proximal end portion 1051 of the restrictor 1050 to be disposed in the lumen 1054. In some embodiments, the restrictor 1050 and the second adapter 1030 can form a friction fit and/or the like, which in turn, can define a substantially fluid tight seal therebetween. In other embodiments, the proximal end portion 1051 of the restrictor 1050 and the distal end portion 1032 of the second adapter 1030 can include any suitable coupling and/or locking mechanism configured to couple the second adapter 1030 to the restrictor 1050 (e.g., as described above with reference to the coupling between the first adapter 1020 and the restrictor 1050).

As shown in FIGS. 19 and 20, the restrictor 1050 or the first adapter 1020 includes a gasket 1026 configured to minimize a discontinuity between the lumen 1024 of the first adapter 1020 and the lumen 1054 of the restrictor 1050 when coupled. Similarly, the second adapter 1030 or the restrictor 1050 includes a gasket 1036. The gaskets 1026 and 1036 can be substantially similar in form and function to the gasket 726 shown and described above with reference to FIGS. 14 and 15. Thus, the gaskets 1026 and 1036 are disposed within the lumen 1024 of the first adapter 1020 and the lumen 1054 of the restrictor 1050, respectively. The arrangement of the gaskets 1026 and 1036 can reduce a magnitude of the discontinuities formed between the inner surfaces 1023, 1033, and 1053 of the first adapter 1020, the second adapter 1030, and the restrictor 1050, respectively, which in turn, can reduce, limit, and/or substantially prevent hemolysis of blood flowing therethrough, as described in detail above. In some embodiments, the gaskets 1026 and 1036 can be configured to restrict and/or reduce a pressure and/or a flow rate associated with the first adapter 1020, the second adapter 1030, and/or the restrictor 1050, as described above with reference to the gasket 726. In some instances, restricting and/or reducing the pressure and/or flow rate associated with the first adapter 1020, the second adapter 1030, and/or the restrictor 1050 (e.g., via the gaskets 1026 and 1036) can, for example, limit shear forces and/or exposure time experienced by red blood cells as the red blood cells flow through the first adapter 1020, the second adapter 1030, and the restrictor 1050, and/or the interfaces therebetween.

The inner surface 1053 of the restrictor 1050 is configured to control a flow of fluid through the lumen 1053. For example, as shown in FIG. 20, the inner surface 1053 of the restrictor 1050 includes a choke portion 1055 or the like. In some embodiments, the choke portion 1055 corresponds to a portion of the inner surface 1053 having a reduced diameter relative to the other portions of the inner surface 1053. More specifically, the choke portion 1055 forms a relatively smooth transition (e.g., a gradual change) from a region of the inner diameter 1053 associated with a first diameter to a region (i.e., the choke portion 1055) associated with a second diameter, smaller than the first diameter. Thus, the choke portion 1055 restricts, controls, and/or reduces a flow of fluid therethrough.

Expanding further, the reduction in the diameter of the inner surface 1053 at or along the choke portion 1055 selectively controls a pressure within the lumen 1054. For example, in some embodiments, the second adapter 1030 can be fluidically coupled (e.g., either directly or indirectly) to an evacuated container or the like, resulting in a negative pressure within the lumens 1034, 1054, and 1024. Thus, the reduced diameter associated with the choke portion 1055 results in a reduced pressure differential between the lumen 1024 of the first adapter 1020 (i.e., at a time directly before the exposure to the negative pressure) and a portion of the lumen 1054 of the restrictor 1050 that is distal to the choke portion 1055. As such, when the first adapter 1020 is in fluid communication with, for example, a vascular structure (e.g., via a needle, catheter, cannula, etc.), a magnitude of the negative pressure exerted on or in the vascular structure is reduced, thereby limiting, reducing, and/or substantially preventing hemolysis of blood as it flows into the lumen 1024 defined by the first adapter 1020. Moreover, the smooth transition in the diameter of the inner surface 1053 from the first diameter to the second diameter (associated with the choke portion 1055), facilitates, encourages, and/or otherwise results in a substantially laminar flow through the lumen 1054 of the restrictor 1050.

While the restrictor 1050 is particularly shown and described above with reference to FIGS. 18-20, in other embodiments, a restrictor, configured to control a flow of fluid therethrough, can be any suitable configuration. For example, FIGS. 21-24 illustrate a restrictor 1150 according to another embodiment. The restrictor 1150 has a proximal end portion 1151, a distal end portion 1152, and an inner surface 1153. The inner surface 1153 of the restrictor 1150 defines a inner volume 1154 extending through its proximal end portion 1151 and its distal end portion 1152 (see e.g., FIG. 22). Although not shown in FIGS. 21-24, the restrictor 1150 can be disposed between two components of a fluid transfer device to define a fluid flow path therethrough. For example, in some embodiments, the proximal end portion 1151 can be coupled to an adapter such as, for example, the second adapter 1030, described above with reference to FIGS. 18-20. Similarly, the distal end portion 1152 can be coupled to an adapter such as, for example, the first adapter 1020, described above. As such, the proximal end portion 1151 and the distal end portion 1152 can be substantially similar to or the same as the proximal end portion 1051 and the distal end portion 1052, respectively, of the restrictor 1050 and thus, are not described in further detail herein.

Figure 22:
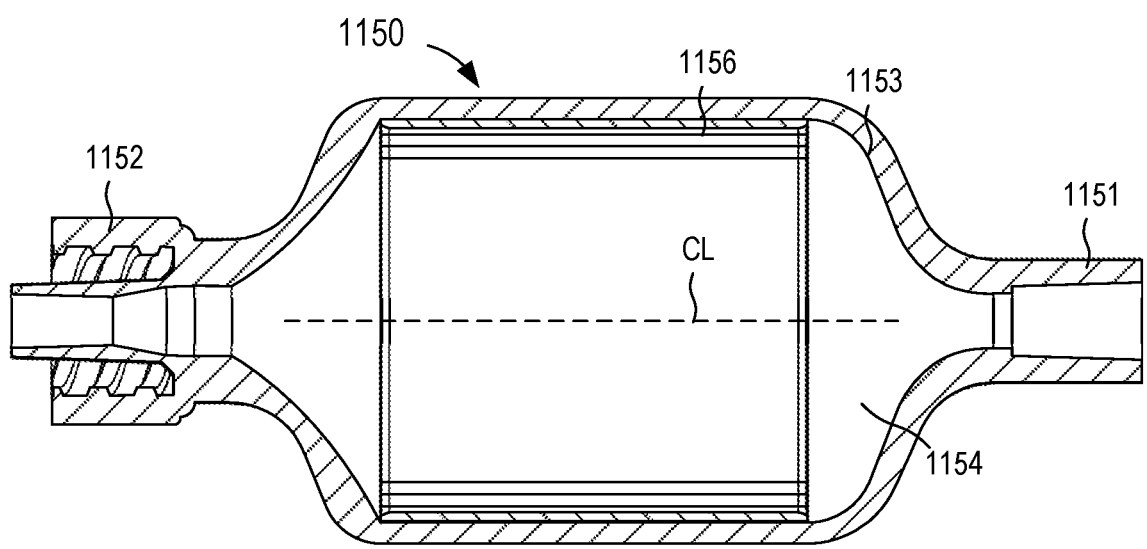
FIG. 22 is a cross-sectional view of the restrictor of FIG. 21, taken along the line 22-22.
Figure 23:
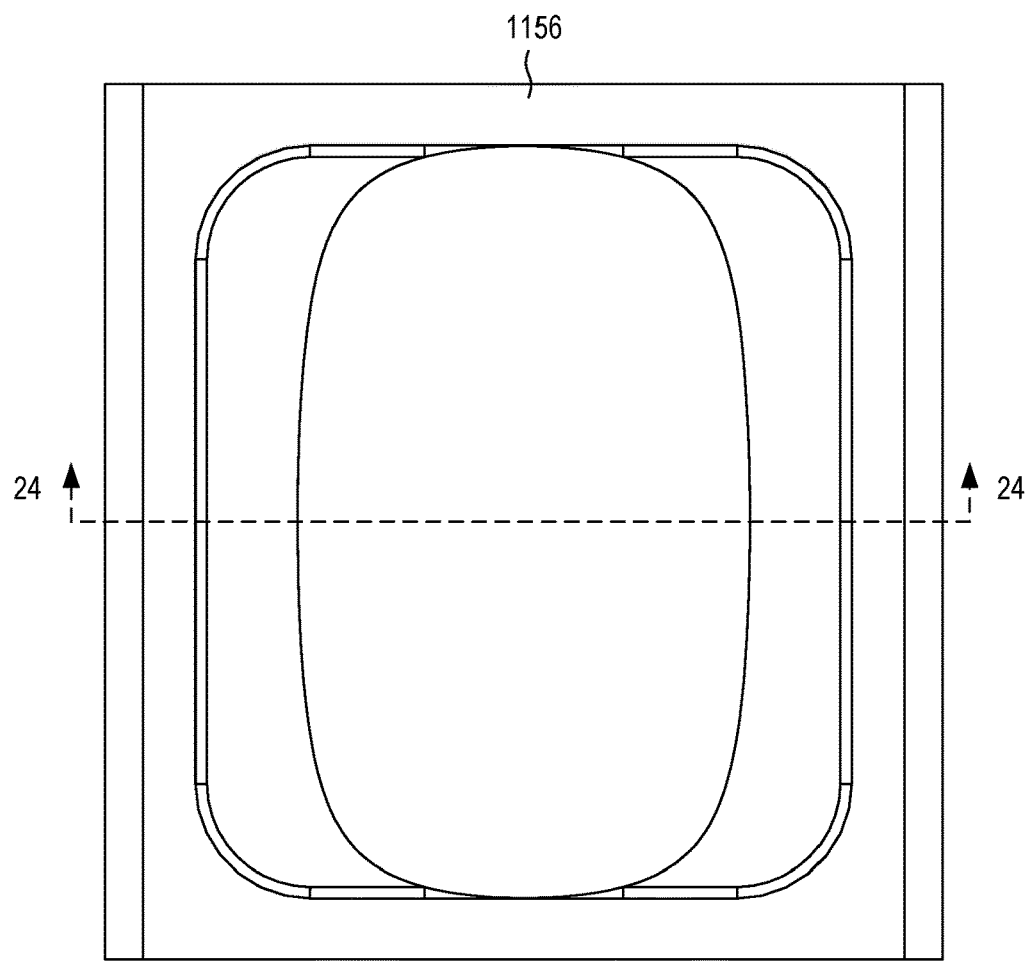
FIG. 23 is a top view of a baffle included in the restrictor of FIG. 21.
Figure 24:
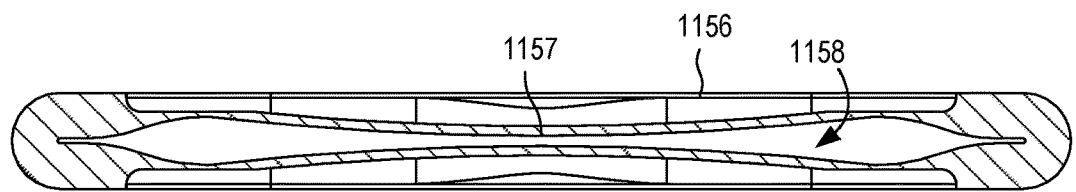
FIG. 24 is a cross-sectional view of the baffle of FIG. 23, taken along the line 24-24.

As shown in FIGS. 22-24, the restrictor 1150 includes a baffle 1156 disposed in the inner volume 1154. The baffle 1156 can be any suitable shape, size, or configuration. For example, in this embodiment, the baffle 1156 is substantially rectangular (see e.g., FIG. 20) with a size that substantially corresponds to the inner volume 1154 of the restrictor 1150, as described in further detail herein. The baffle 1156 includes an inner surface 1157 that defines an inner volume 1158. As shown in FIG. 24, the inner surface 1157 of the baffle 1156 defines a gradual bow toward the center of the baffle 1156. More specifically, the arrangement of the inner surface 1157 is such that a distance between opposite sides of the baffle 1156 gradually varies as the inner surface 1157 extends outward from a longitudinal centerline CL (shown in FIG. 22) of the baffle 1156. For example, in this embodiment, a distance between opposite portions of the inner surface 1157 gradually increases from a first distance, at a first position associated with a perimeter of the inner surface 1157, to second distance, at a second position disposed between the perimeter of the inner surface 1157 and the longitudinal centerline CL, and then gradually decreases from the second distance to a third distance, at a position associated with and/or near the longitudinal center CL. In this manner, the baffle 1156 can selectively control a flow of fluid through the inner volume 1158, as described in further detail herein.

Referring back to FIG. 22, in this embodiment, an outer surface of the baffle 1156 is in contact with the inner surface 1153 of the restrictor 1150 when disposed in the inner volume 1154. In some embodiments, the outer surface of the baffle 1156 and the inner surface 1153 of the restrictor 1150 define a friction fit or the like that forms a substantially fluid tight seal. As such, the arrangement of the baffle 1156 and the inner surface 1153 of the restrictor 1150 can limit, inhibit, and/or substantially prevent a flow of fluid between the outer surface of the baffle 1156 and the inner surface 1153 of the restrictor 1150. More specifically, the inner volume 1158 of the baffle 1156 defines a fluid flow path that places a first portion of the inner volume 1154, which is distal to the baffle 1156, in fluid communication with a second portion of the inner volume 1154, which is proximal to the baffle 1156. In this manner, the arrangement of the inner surface 1157 of the baffle 1156 can restrict, inhibit, guide, limit, choke, and/or otherwise control a flow of fluid through the restrictor 1150. Moreover, the smooth or gradual change in distance between opposite portions of the inner surface 1157 of the baffle (as described above) facilitates, encourages, and/or otherwise results in a substantially laminar flow through the inner volume 1154 of the restrictor 1150.

Although not shown in FIGS. 21-24, in some embodiments, the inner volume 1158 of the baffle 1156 can include a medium disposed therein. For example, in some embodiments, the baffle 1156 can include a substantially porous material or the like that can slow and/or filter a flow of fluid (e.g., blood) therethrough. In other embodiments, the user can manipulate the restrictor 1150 to modify and/or control a flow of fluid through the restrictor 1150. For example, in some instances, the user can exert a force on a portion of the restrictor 1150 sufficient to deform that portion. As such, a portion of the force can correspondingly deform the baffle 1156, which in turn, can change a contour of the inner surface 1157. Thus, the user can exert a force on the restrictor 1150 to, for example, increase, decrease, or otherwise control a flow of fluid through the baffle 1156. By way of example, a user can exert a force of the restrictor 1150 to reduce a distance between opposite portions of the inner surface 1157, which in turn, can reduce a negative pressure differential produced by an evacuated container being placed in fluid communication with the restrictor 1150.

Figure 25:
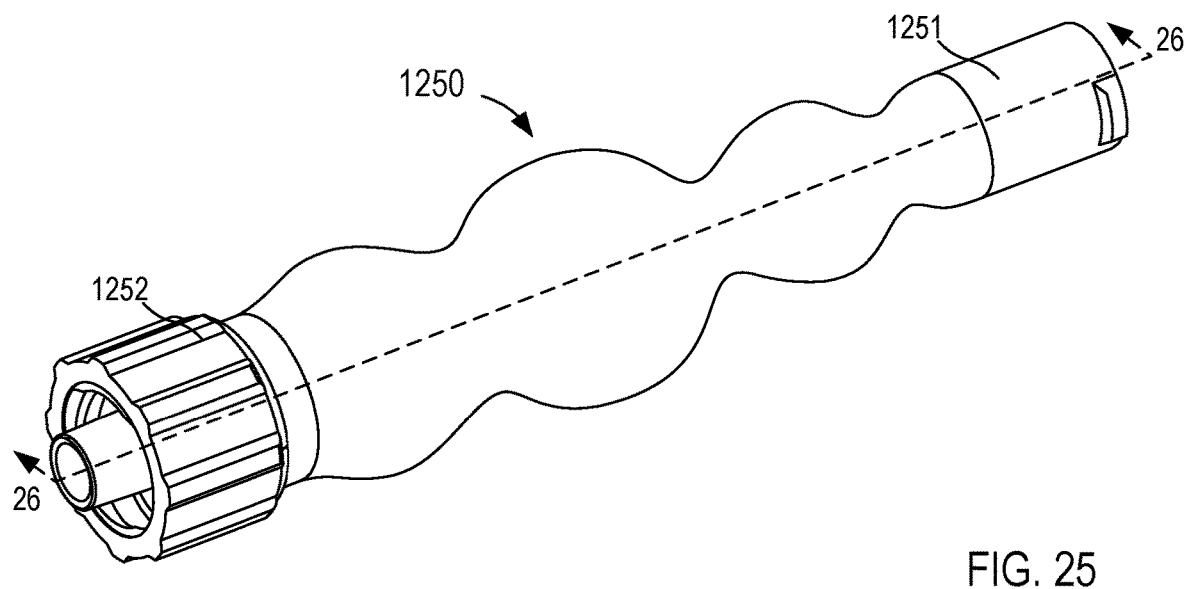
FIG. 25 is a perspective view of a restrictor included in a bodily-fluid collection device according to an embodiment.
Figure 26:
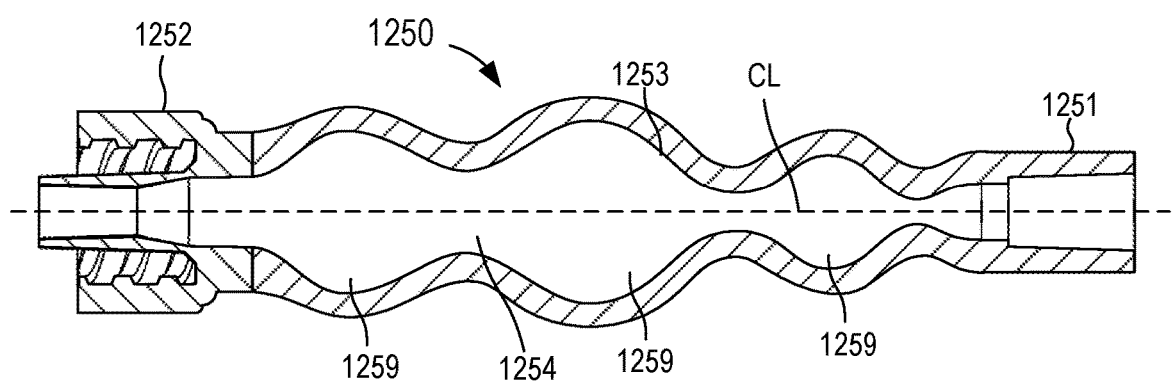
FIG. 26 is a cross-sectional view of the restrictor of FIG. 25, taken along the line 26-26.

FIGS. 25 and 26 illustrate a restrictor 1250 according to another embodiment. The restrictor 1250 has a proximal end portion 1251, a distal end portion 1252, and an inner surface 1253. The inner surface 1253 of the restrictor 1250 defines a inner volume 1254 extending through its proximal end portion 1251 and its distal end portion 1252 (see e.g., FIG. 26). As described above, the restrictor 1250 can be physically and fluidically coupled between, for example, a pair of components of a fluid transfer device to restrict and/or otherwise control a flow of fluid therebetween. For example, although not shown in FIGS. 25-26, the proximal end portion 1251 can be coupled to an adapter such as, for example, the second adapter 1030, described above with reference to FIGS. 18-20. Similarly, the distal end portion 1252 can be coupled to an adapter such as, for example, the first adapter 1020, as described above. In this manner, the proximal end portion 1251 and the distal end portion 1252 can be substantially similar to or the same as the proximal end portion 1051 and the distal end portion 1052, respectively, of the restrictor 1050 and thus, are not described in further detail herein.

The restrictor 1250 includes and/or defines a set of chambers 1259, as shown in FIG. 26. More specifically, the restrictor 1250 includes a set of walls that can form, for example, a set of semi-spherical portions, which in turn, result in the inner surface 1253 defining the set of chambers 1259. Thus, the chambers 1259 are, for example, a set of semi-spherical portions of the inner volume 1254. As shown in FIG. 26, the chambers 1259 are serially arranged along a longitudinal centerline CL of the restrictor 1250. In some embodiments, the size and/or shape of each chamber 1259 can vary. For example, as shown in FIG. 26, the chamber 1259 disposed at or near the proximal end portion 1251 of the restrictor 1250 is smaller than the adjacent chamber 1259. In other embodiments, the size and/or shape of each chamber 1259 can be substantially uniform. With the inner surface 1253 defining the semi-spherical chambers 1259, a diameter of the inner volume 1254 (e.g., associated with a cross-sectional shape of the inner surface 1253) is varied along a length of the longitudinal centerline CL. For example, a diameter of the inner volume 1254 gradually increases or decreases in an alternating manner between a relatively smaller diameter, associated with a position along the longitudinal centerline substantially between adjacent chambers 1259 and a relatively larger diameter, associated with a position along the longitudinal centerline substantially in the center of a given chamber 1259.

In some embodiments, the arrangement of the chambers 1259 selectively controls a pressure within the inner volume 1254. For example, in some embodiments, the proximal end portion 1251 of the restrictor 1250 can be fluidically coupled (e.g., either directly or indirectly) to an evacuated container or the like, resulting in a negative pressure within the inner volume 1254. Thus, the alternating increase and decrease corresponding to each chamber 1259 results in a changing pressure differential along the longitudinal centerline CL. In some embodiments, such an alternating arrangement can, for example, act as a peristaltic pump or the like. Thus, the restrictor 1250 can draw a fluid through the inner volume 1254 via a pressure differential that is at least partially controlled by the arrangement of the inner surface 1253. That is to say, while an evacuated container is the source of a negative pressure, the arrangement of the chambers 1259 at least partially controls a pressure differential between the proximal end portion 1251 and the distal end portion 1252. In this manner, hemolysis of blood can be reduced and/or substantially prevented, which might otherwise occur in response to a shear force produced by a relatively rapid and/or relatively large pressure drop associated with placing an evacuated container in fluid communication with a vascular structure. Moreover, the smooth and/or gradual transitions in the diameter of the inner surface 1253 associated with the chambers 1259, facilitates, encourages, and/or otherwise results in a substantially laminar flow through the inner volume 1254 of the restrictor 1250.

Figure 27:
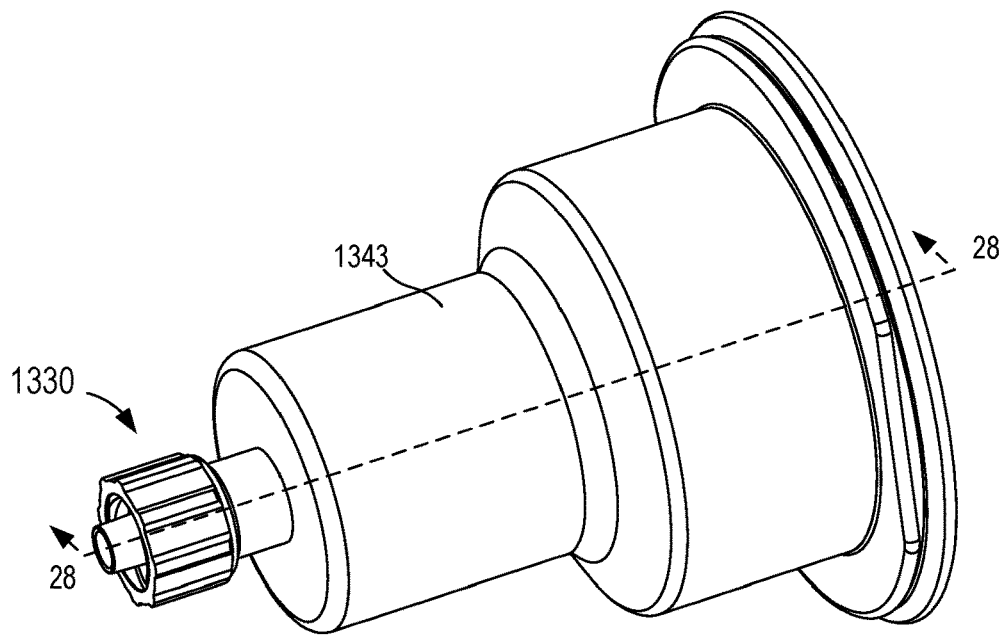
FIG. 27 is a perspective view of an adapter included in a bodily-fluid collection device according to an embodiment.
Figure 28:
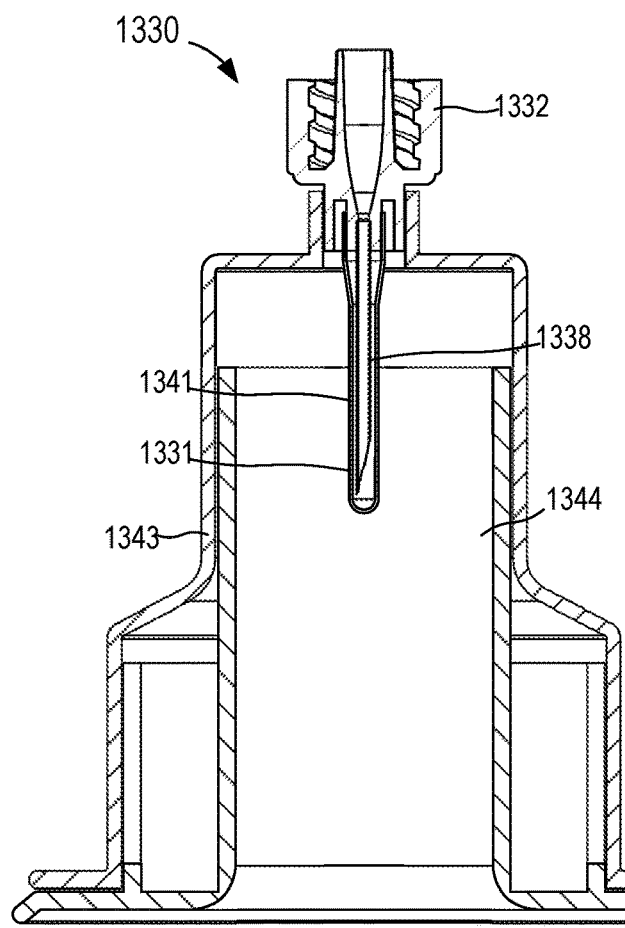
FIG. 28 is a cross-sectional view of the adapter of FIG. 27, taken along the line 28-28.

Although not shown, any of the restrictors 1050, 1150, and/or 1250 can be fluidically coupled (either directly or indirectly) to and/or monolithically formed with an adapter configured to engage a fluid reservoir such as an evacuated container. In some embodiments, such adapters can include an inner surface configured to reduce discontinuities or the like within a portion of a fluid flow path and/or otherwise configured to facilitate a substantially laminar fluid flow therethrough, as described in detail above. Moreover, the adapters can engage any suitable fluid reservoir or container. For example, FIGS. 27-44 illustrate embodiments (i.e., adapters and fluid reservoirs) configured to mitigate the risk of hemolysis as blood flow from an adapter, a puncture member, a needle, a cannula, and/or the like into a fluid reservoir. Specifically, FIGS. 27-33 illustrate an adapter 1330 configured to engage a fluid reservoir 1360 (FIGS. 29-33) according to an embodiment. The adapter 1330 has a proximal end portion 1331, a distal end portion 1332, and an inner surface 1333. The inner surface 1333 defines a lumen 1334 extending through the proximal end portion 1331 and the distal end portion 1332 (see e.g., FIG. 27). As shown in FIGS. 27 and 28, in some embodiments, the adapter 1330 can include and/or can be coupled to a shroud 1343. In such embodiments, the shroud 1343 can define an inner volume 1344 within which a portion of a fluid reservoir can be disposed. In other embodiments, the adapter 1330 need not include and/or need not be coupled to the shroud 1343.

Figure 30:
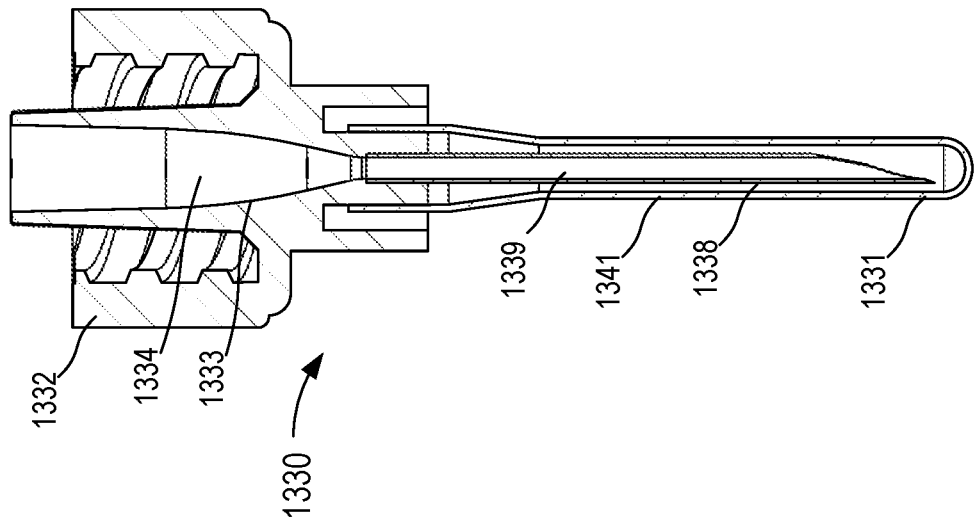
FIG. 30 is a cross-sectional view of the portion of the adapter illustrated in FIG. 29, taken along the line 30-30.
Figure 29:
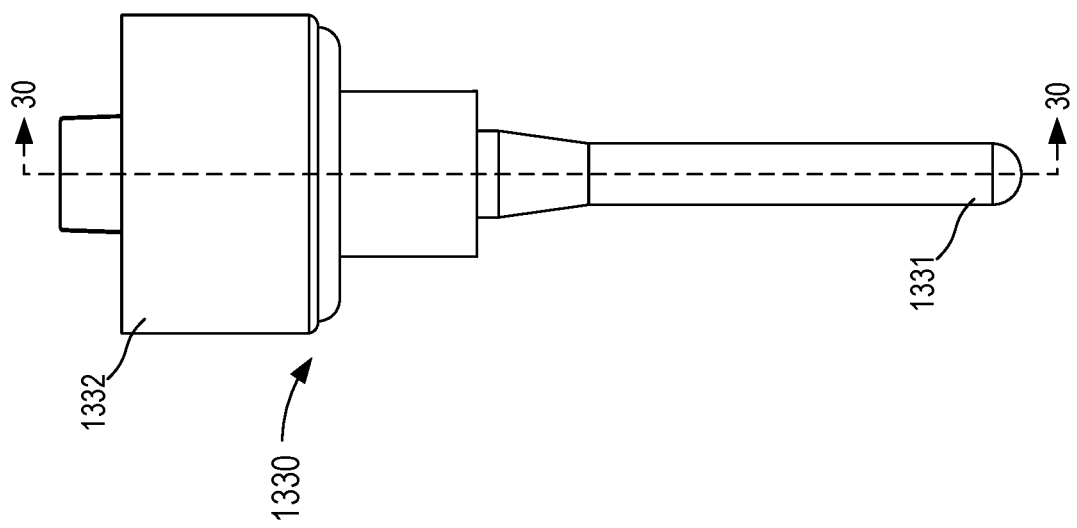
FIG. 29 is a front view of a portion of the adapter of FIG. 27.

The adapter 1330 can be any suitable shape, size, or configuration. For example, as shown in FIGS. 29 and 30, the distal end portion 1332 of the adapter 1330 includes and/or is coupled to a lock mechanism or the like. In this embodiment, the distal end portion 1332 includes and/or forms a female portion of a Luer Lok® or the like. Thus, the distal end portion 1332 of the adapter 1330 can be coupled to a corresponding male portion of a Luer Lok® or the like, as described above with reference to the distal end portion 1052 of the restrictor 1050 shown in FIG. 20. The proximal end portion of the adapter 1330 includes and/or is coupled to a puncture member 1338 defining a lumen 1339 in fluid communication with the lumen 1334 of the adapter 1330. The puncture member 1338 can be any suitable configuration. For example, in some embodiments, the puncture member 1338 is a needle. As shown in FIG. 30, the puncture member 1325 is disposed within a sheath 1341. More specifically, the sheath 1341 is at least temporarily disposed about the puncture member 1338 and is configured to limit and/or substantially prevent an accidental contact with the puncture member 1338. Furthermore, the sheath 1341 can maintain the puncture member 1338 in a substantially sterile environment prior to use and can selectively control a flow of bodily fluid through the puncture member 1338, as described in further detail herein.

As shown in FIG. 30, a diameter of the inner surface 1333 at or near the distal end portion 1332 is larger than a diameter of the puncture member 1338. In this manner, the inner surface 1333 forms and/or defines a smooth transition from a larger diameter at or near the distal end portion 1332 to a smaller diameter at or near the puncture member 1338. In some instances, such a smooth transition from the larger diameter to the smaller diameter can facilitate, produce, encourage, and/or force a substantially laminar flow of a volume of bodily fluid (e.g., blood) through the lumen 1334. Moreover, the smooth transition can reduce eddy currents or the like within the flow of blood that can otherwise result from a relatively abrupt change in diameter or the like. Thus, a volume of blood can flow within the lumens 1334 and 1339 with reduced damage to the constituents of the blood (e.g., hemolysis of the erythrocytes) that might otherwise occur as a result of misaligned interfaces and/or discontinuities; abrupt changes in diameter; turbulence and/or eddy currents within a flow of blood therethrough; and/or the like.

Figure 33:
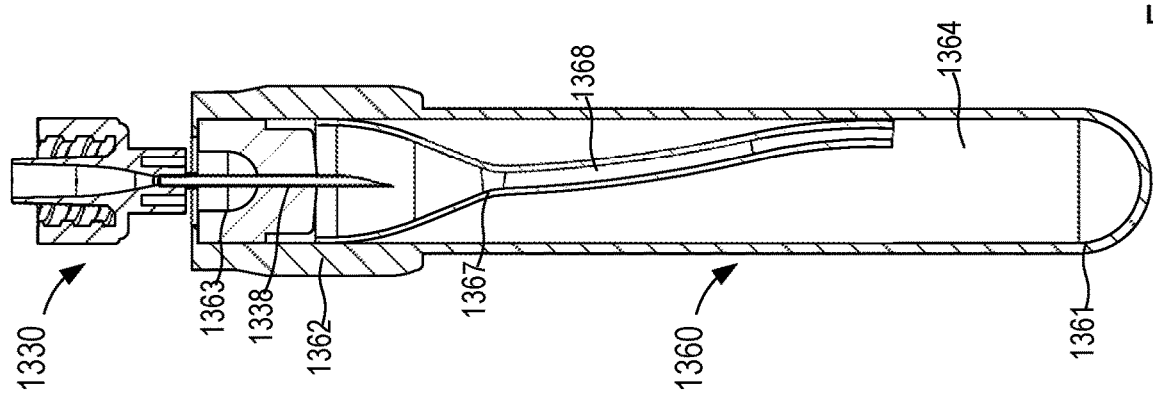
FIG. 33 is a cross-sectional view of the portion of the adapter and the fluid reservoir illustrated in FIG. 31, taken along the line 33-33.
Figure 32:
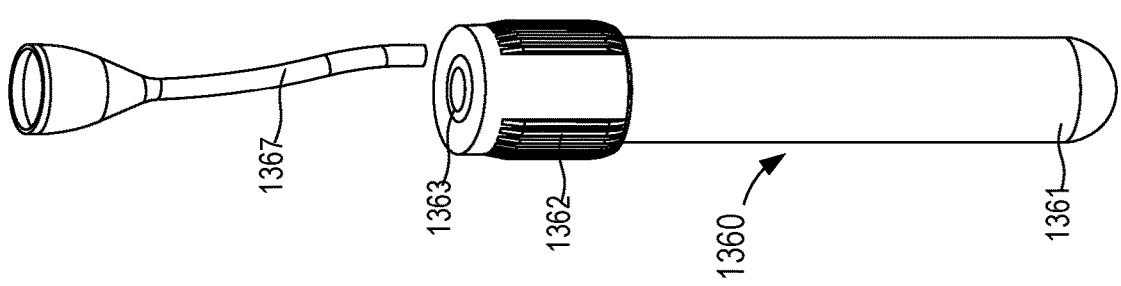
FIG. 32 is an exploded view of the fluid reservoir of FIG. 31.
Figure 31:
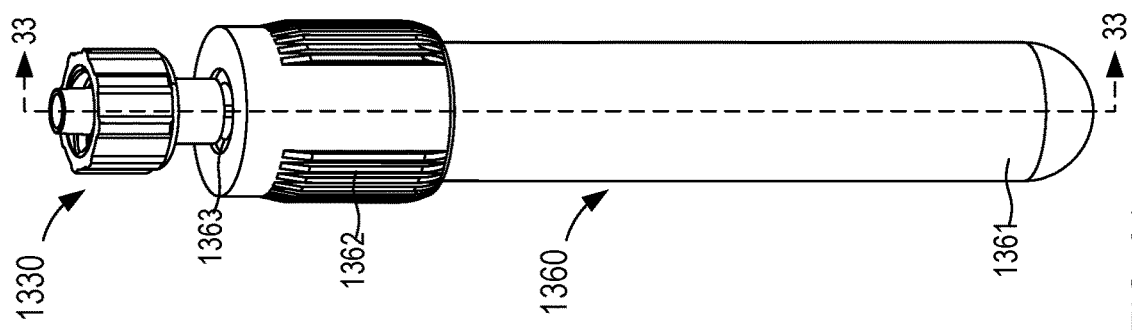
FIG. 31 is a perspective view of the portion of the adapter illustrated in FIG. 29 coupled to a fluid reservoir according to an embodiment.

As described above, the adapter 1330 is configured to couple to and/or otherwise engage a fluid reservoir 1360. The fluid reservoir 1360 can be any suitable shape, size, or configuration. For example, in this embodiment, the fluid reservoir 1360 is an evacuated container such as a Vacutainer™, a BacT/ALERT® SN, a BacT/ALERT® FA, and/or any other type of container, vial, bottle, reservoir, etc. As shown in FIGS. 31-33, the fluid reservoir 1360 includes a proximal end portion 1361 and a distal end portion 1362, and defines an inner volume 1364. The distal end portion 1362 includes a port 1363 through which the puncture member 1338 can be inserted to place the inner volume 1364 of the fluid reservoir 1360 in fluid communication with the lumen 1334 of the adapter 1330. For example, in some embodiments, the port 1363 can be a self-healing septum or the like. Thus, the port 1363 can be substantially in a sealed configuration prior to insertion of, for example, the puncture member 1338 and subsequently, can transition from an open configuration to the sealed configuration when, for example, the puncture member 1338 is removed from the port 1363.

In some embodiments, a fluid reservoir can include a flow control member or the like disposed in its inner volume. For example, as shown in FIGS. 32 and 33, the fluid reservoir 1360 includes a flow control member 1367 disposed within the inner volume 1364. In this embodiment, the flow control member 1367 can be, for example, an insert or funnel that defines a channel 1368 configured to receive a flow of fluid from the lumen 1339 of the puncture member 1338. More specifically, as shown in FIG. 33, a first end of the flow control member 1367 can be disposed adjacent to and/or can be coupled to the port 1363 and a second end, opposite the first end, can extend toward an inner surface of the fluid reservoir 1360. In this manner, the second end of the flow control member 1367 can be adjacent to the inner surface of the fluid reservoir 1360 such that an axis associated with a portion of the channel 1368 at or near the second end is substantially parallel to and/or otherwise directed toward the inner surface of the fluid reservoir 1360.

In use, the adapter 1330 and/or the fluid reservoir 1360 can be manipulated to insert the puncture member 1338 through the port 1363 of the fluid reservoir 1360. As such, the sheath 1341 disposed about the puncture member 1338 can deform to allow the puncture member 1338 to be inserted through the port 1363. With the fluid reservoir 1360 being an evacuated container, the insertion of the puncture member 1338 is such that a negative pressure within the fluid reservoir 1360 is exerted through the lumen 1334 of the adapter 1330 (e.g., via the lumen 1339 of the puncture member 1338). Thus, when the distal end portion 1332 is fluidically coupled (either directly or indirectly) to a device or member in fluid communication with the body of a patient, the negative pressure draws a volume of bodily fluid (e.g., blood) from the patient and into the fluid reservoir 1360. More specifically, the distal end portion 1332 of the adapter 1330 can be coupled (either directly or indirectly) to any suitable adapter, restrictor, and/or needle described herein to receive a flow of, for example, blood from the patient with reduced or substantially no hemolyzation of the blood. Furthermore, by disposing the flow control member 1367 in the inner volume 1364, a flow of blood can be directed within the channel 1338 toward the inner surface, which in turn, can decrease a force otherwise associated with an impact of the volume of blood contacting the inner surface. Thus, hemolysis of the blood associated with such a contact is reduced or substantially prevented.

While the adapter 1330 is shown in FIGS. 31-33 as not including and/or not be coupled to the shroud 1343, in other embodiments, the adapter 1330 can be coupled to the shroud 1343 when engaging the fluid reservoir 1360. Furthermore, while the flow control member 1367 is particularly shown in FIG. 33, in some embodiments, a second end of a flow control member can extend within the inner volume 1364 to a position adjacent to and/or substantially abutting a bottom or proximal surface (i.e., a surface opposite the port 1363). In other embodiments, a flow control member can extend in a spiral or helical manner from the port 1363. As such, a second end of the flow control member can be substantially tangential to the inner surface of the fluid reservoir and thus, fluid exiting a channel defined by the flow control member can flow along a circumference of the inner surface (e.g., tangent to the inner surface).

Figure 34:
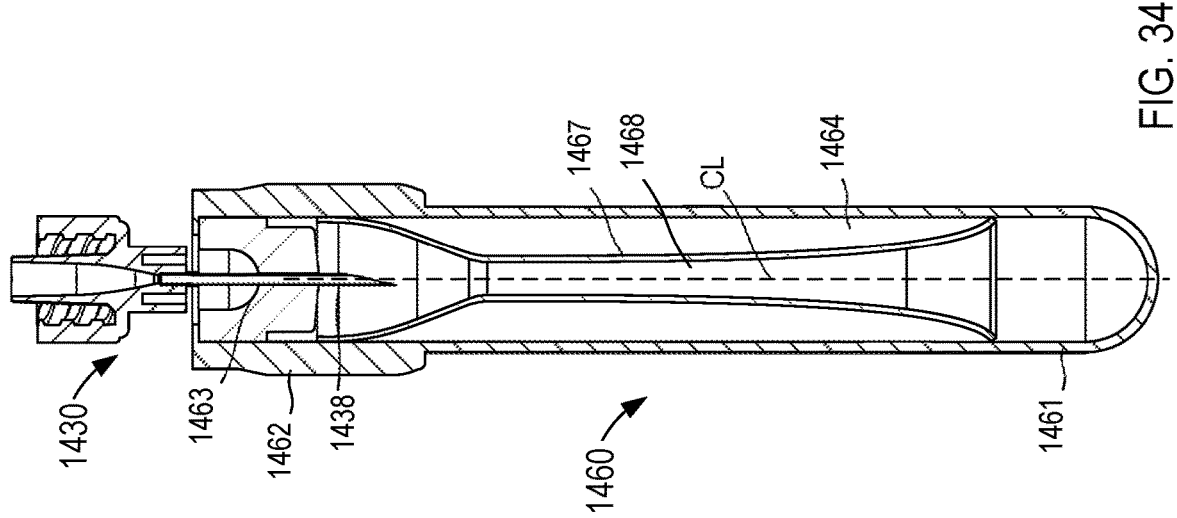
FIG. 34 is a cross-sectional view of an adapter coupled to a fluid reservoir according to another embodiment.

In other embodiments, a fluid reservoir can include any suitable flow control member. For example, FIG. 34 illustrates a fluid reservoir 1460 according to another embodiment. The fluid reservoir 1460 includes a proximal end portion 1461 and a distal end portion 1462, and defines an inner volume 1464. The distal end portion 1462 includes a port 1463 configured to receive, for example, a puncture member 1438 of an adapter 1430, as described in detail above with reference to FIGS. 31-33. The inner volume 1464 of the fluid reservoir 1460 includes and/or houses a flow control member 1467 operable to control a flow of fluid from, for example, the adapter 1430 into the inner volume 1464, as described in further detail herein. The fluid reservoir 1460 can be any suitable shape, size, or configuration. For example, in this embodiment, the fluid reservoir 1460 is an evacuated container such as a Vacutainer™, a BacT/ALERT® SN, a BacT/ALERT® FA, and/or any other type of container, vial, bottle, reservoir, etc. In some embodiments, the fluid reservoir 1460 can be substantially similar to or the same as the fluid reservoir 1360 described above with reference to FIGS. 31-33. Thus, such similar aspects of the fluid reservoir 1460 are not described in further detail herein.

The fluid reservoir 1460 can differ from the fluid reservoir 1360, however, in the arrangement of the flow control member 1467. More specifically, while the flow control member 1367 is shown in FIG. 33 as tapering to a substantially uniform diameter as the flow control member 1367 extends away from the port 1363, in this embodiment, the flow control member 1467 has a varying diameter as the flow control member 1467 extends away from the port 1463. In this manner, a channel 1468 defined by the flow control member 1467 has a cross-sectional area and/or diameter that is dependent on, for example, a position along a longitudinal centerline CL defined by the flow control member 1467. For example, the channel 1468 can have a first diameter at a first end portion nearest to the port 1463, a second diameter at an end portion opposite the first end portion, and a third diameter at a portion disposed therebetween. As shown in FIG. 34, the end portions of the flow control member 1467 can be flared or the like such that the first diameter and the second diameter are each greater than the third diameter. Said another way, the diameter of the channel 1468 can taper along the longitudinal centerline CL from a larger diameter associated with the end portions of the flow control member 1467 to a smaller diameter at or near a center portion of the flow control member 1467.

With the fluid reservoir 1460 being an evacuated container or the like, a pressure (i.e., a negative pressure) within the channel 1468 is dependent on a position along the longitudinal centerline CL. That is to say, the pressure within the channel 1468 is dependent on the diameter of the channel 1468, in which a larger diameter is associated with a larger pressure. In a similar manner, the velocity of a flow of bodily fluid (e.g., blood) within the channel 1468 is also dependent on the diameter of the channel 1468, however, such dependency is inverse to that associated with the pressure (i.e., a larger diameter is associated with less velocity). Thus, as blood (or other bodily fluid) flows through the channel 1468, the increase in diameter at the end portion of the flow control member 1467 opposite the port 1463 results in a decrease in velocity associated with the flow of bodily-fluid therethrough. As such, a force otherwise associated with a volume of blood contacting an inner surface of the fluid reservoir 1460 is reduced, which in turn, can reduce and/or substantially prevent hemolysis of the volume of blood. Moreover, the diameter of the channel 1468 can be such that a pressure within the channel 1468 is maintained below a threshold that can otherwise result in hemolysis of blood flowing therethrough.

Figure 35:
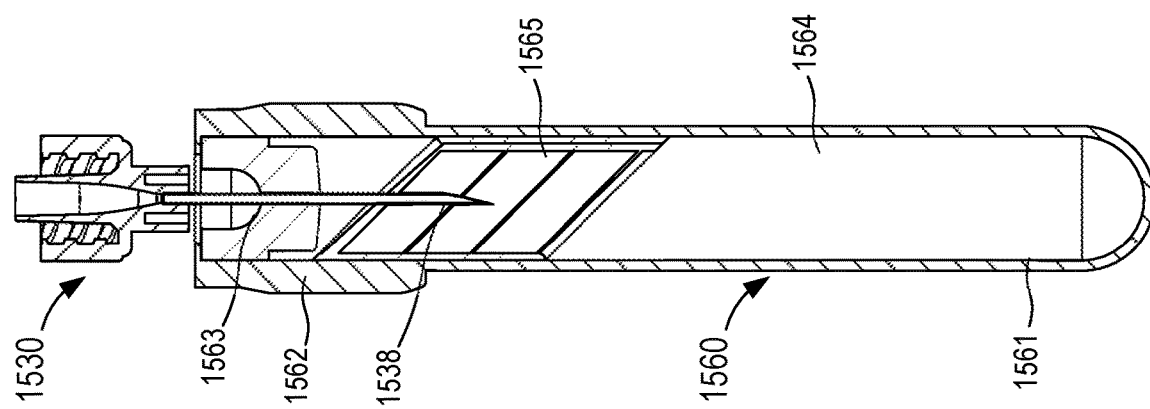
FIG. 35 is a cross-sectional view of an adapter coupled to a fluid reservoir according to another embodiment.

While the flow control members 1367 and 1467 are shown and described above as controlling a flow of, for example, blood through the channels 1368 and 1468, respectively, in other embodiments, a fluid reservoir can include a flow control member having any suitable configuration. For example, FIG. 35 illustrates a fluid reservoir 1560 according to another embodiment. The fluid reservoir 1560 includes a proximal end portion 1561 and a distal end portion 1562, and defines an inner volume 1564. The distal end portion 1562 includes a port 1563 configured to receive, for example, a puncture member 1538 of an adapter 1530, as described in detail above with reference to FIGS. 31-33. The inner volume 1564 of the fluid reservoir 1560 includes and/or houses a flow control member 1565 operable to control a flow of fluid from, for example, the adapter 1530 into the inner volume 1564, as described in further detail herein. The fluid reservoir 1560 can be any suitable shape, size, or configuration. For example, in this embodiment, the fluid reservoir 1560 is an evacuated container such as a Vacutainer™, a BacT/ALERT® SN, a BacT/ALERT® FA, and/or any other type of container, vial, bottle, reservoir, etc. In some embodiments, the fluid reservoir 1560 can be substantially similar to or the same as the fluid reservoir 1360 described above with reference to FIGS. 31-33. Thus, such similar aspects of the fluid reservoir 1560 are not described in further detail herein.

As shown in FIG. 35, the flow control member 1565 is disposed within the inner volume 1564 at or near the port 1563. In this embodiment, the flow control member 1565 is a baffle insert or the like. Specifically, the flow control member 1565 forms and/or includes an angled baffle having a set of substantially parallel angled surfaces configured to direct a flow of blood or other bodily fluid. For example, the puncture member 1538 of the adapter 1530 can be inserted through the port 1563 to place a distal end portion of the puncture member 1538 within the flow control member 1565. As such, when a flow of blood is expelled and/or drawn through a lumen defined by the puncture member 1538 (e.g., via a negative pressure differential produced by the evacuated container), the flow of blood contacts at least one angled surface of the flow control member 1565. Thus, the blood can flow along the angled surface toward an inner surface of the fluid reservoir 1560. By diverting, guiding, and/or otherwise directing the flow of blood to the inner surface, a force is reduced, which can otherwise result from an impact of the volume of blood contacting the inner surface. Thus, hemolysis of the blood associated with such a contact is reduced or substantially prevented.

While the flow control member 1565 is shown and described as forming and/or including a set of parallel angled surfaces configured to direct a flow of bodily fluid toward the inner surface of the fluid reservoir 1560, in other embodiments, a flow control member can be any suitable baffle or the like. For example, in some embodiments, a flow control member can be an angled baffle or the like having a set of angled surfaces with an alternating orientation or the like. By way of example, a flow control member can include a first set of angled surfaces with a cross-sectional orientation (as shown in FIG. 35) that forms a 30° with a given plane and a second set of angled surfaces with a cross-sectional orientation that forms a 150° orientation with the given plane (i.e., a mirrored orientation), with each angled surface of the first set being disposed between two angled surfaces of the second set (or vice versa). In some embodiments, a baffle can include a set of surfaces that are each substantially V-shaped or U-shaped.

In other embodiments, a flow control member can be an absorbent or porous baffle or the like that can fill at least a portion of an inner volume of a fluid reservoir. In this manner, a flow of blood can be expelled or drawn from a lumen of an adapter (e.g., a lumen of a puncture member or the like) and absorbed by the absorbent baffle. In such embodiments, a volume of blood can be subsequently released or expelled from the absorbent baffle via a centripetal or centrifugal action and/or the like. In some embodiments, a flow control member can be a baffle including a set of angled surfaces with an absorbent material disposed therebetween.

Figure 36:
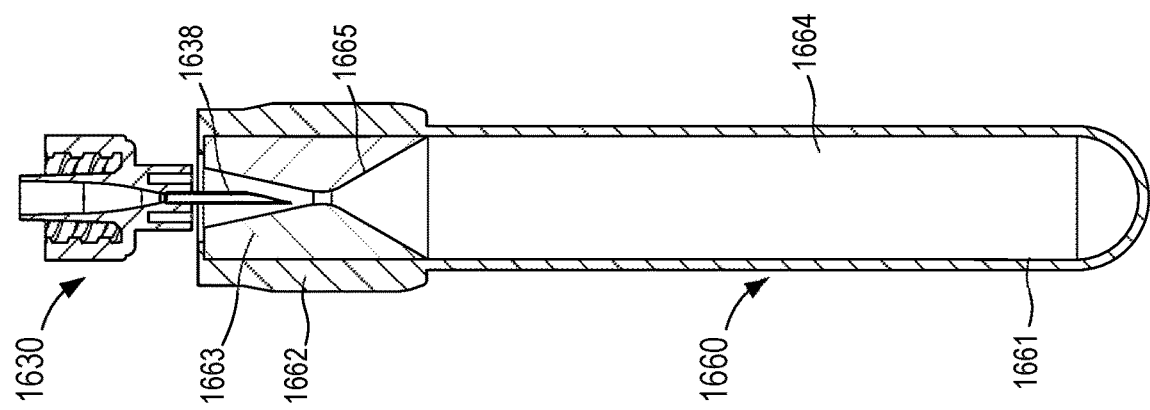
FIG. 36 is a cross-sectional view of an adapter coupled to a fluid reservoir according to another embodiment.

While the flow control members 1367, 1467, and 1565 are shown as independent components disposed within the fluid reservoirs 1360, 1460, and 1560, respectively, in other embodiment, a fluid reservoir can include a flow control member that is integral with another portion of the fluid reservoir such as, for example, a port. For example, FIG. 36 illustrates a fluid reservoir 1660 according to another embodiment. The fluid reservoir 1660 can be any suitable shape, size, or configuration. For example, in this embodiment, the fluid reservoir 1660 is an evacuated container such as a Vacutainer™, a BacT/ALERT® SN, a BacT/ALERT® FA, and/or any of type of container, vial, bottle, reservoir, etc. In some embodiments, the fluid reservoir 1660 can be substantially similar to or the same as the fluid reservoir 1360 described above with reference to FIGS. 31-33. Thus, such similar aspects of the fluid reservoir 1660 are not described in further detail herein.

The fluid reservoir 1660 includes a proximal end portion 1661 and a distal end portion 1662, and defines an inner volume 1664. The distal end portion 1662 includes a port 1663 configured to receive, for example, a puncture member 1638 of an adapter 1630, as described in detail above with reference to FIGS. 31-33. The port 1663 in this embodiment, however, includes an inner surface 1665 configured to control a flow of fluid into the inner volume 1664 of the fluid reservoir 1660. As shown in FIG. 36, the inner surface 1665 of the port 1663 has a varied diameter that forms a constriction disposed between a proximal end portion and a distal end portion of the port 1663. For example, in some embodiments, the inner surface 1665 can form a constriction or otherwise can have a reduced diameter at or near a center of the port 1663 (i.e., at or near a midpoint between the proximal end portion and the distal end portion of the port).

In some embodiments, the inner surface 1665 can have a reduced diameter at a position that is proximal to the puncture member 1638 when the adapter 1630 is engaged with the fluid reservoir 1660. Similarly stated, the arrangement of the fluid reservoir 1660 and the adapter 1630 is such that when the adapter 1630 engages the fluid reservoir 1660, the puncture member 1638 is disposed in a distal position relative to a portion of the inner surface 1665 associated with the smallest diameter. Thus, the arrangement of the inner surface 1665 of the port 1663 can, for example, result in a venturi effect within a volume of bodily fluid as the volume of bodily-fluid flows from the puncture member 1638 into the port 1663. In other words, with the inner surface 1665 forming a constriction and/or reduction in diameter, a pressure associated with a volume on opposite sides of the constriction and/or reduction in diameter can be controlled. For example, the fluid reservoir 1660, being an evacuated container, defines a negative pressure within a portion of the inner volume 1664 proximal to the portion of the inner surface 1665 having the reduced diameter. In some embodiments, the constriction and/or reduced diameter formed by the inner surface 1665 results in a corresponding decrease in pressure associated with the reduced diameter. Thus, by selectively controlling a portion of the inner surface 1665 that is distal to the reduced diameter (i.e., selectively increasing the diameter of the inner surface 1665) a pressure within a volume distal to the reduced diameter can be less than, for example, the pressure within the volume proximal to the reduced diameter. Thus, hemolysis within a flow of blood is reduced or substantially prevented that might otherwise result from a rapid exposure to the negative pressure differential produced by the fluid reservoir 1660.

Figure 38:
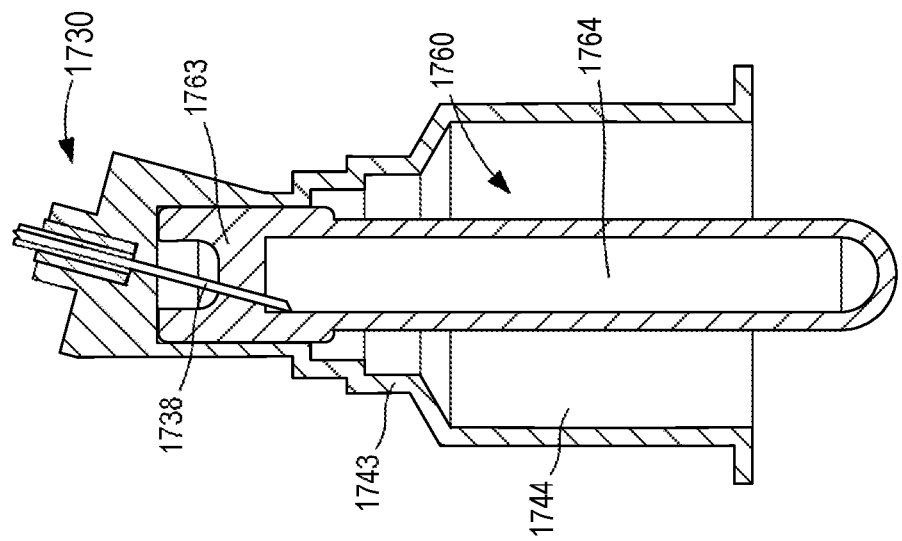
FIG. 38 is a cross-sectional view of the adapter and the fluid reservoir of FIG. 37, taken along the line 38-38.
Figure 37:
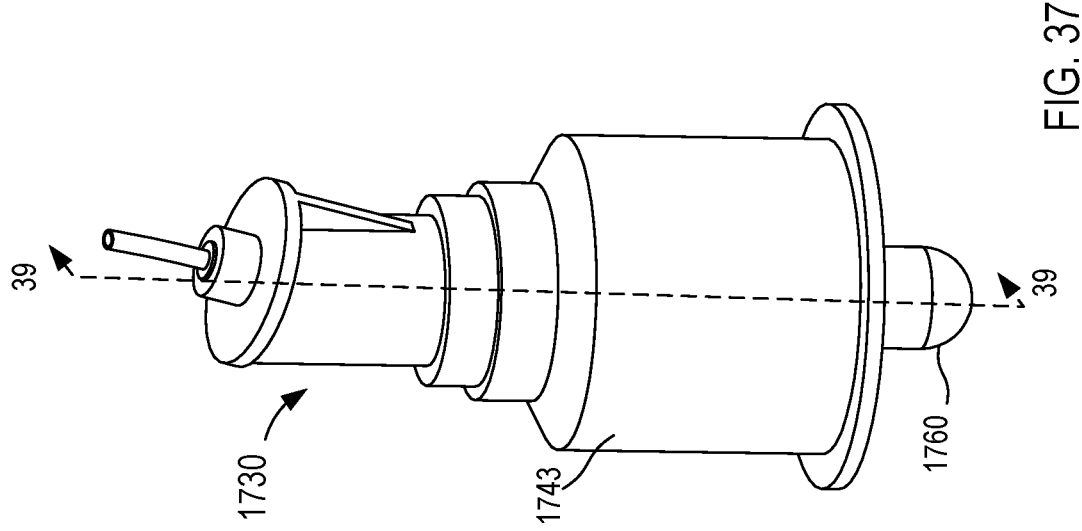
FIG. 37 is a perspective view of an adapter coupled to a fluid reservoir according to another embodiment.

While the flow control members 1367, 1467, 1565, and the port 1663 are shown and described above as receiving and/or otherwise guiding a flow of bodily-fluid (e.g., blood) into the inner volumes 1364, 1464, 1564, 1664, respectively, in some embodiments, an adapter can be arranged to selectively direct a flow of bodily-fluid into a fluid reservoir. For example, FIGS. 37 and 38 illustrate an adapter 1760, according to another embodiment. The adapter 1760 is configured for selective engagement with a fluid reservoir 1760 to deliver a flow of bodily fluid into an inner volume 1764. The adapter 1760 includes at least a shroud 1743 and a puncture member 1768. Although not shown in FIGS. 37 and 38, an inner surface of the adapter 1760 can be substantially similar to or the same as the inner surface 1363 of the adapter 1360 described above with reference to FIG. 30. That is to say, the adapter 1760 can include an inner surface that defines a substantially smooth transition between, for example, a lumen associated with an inlet of the adapter 1760 (e.g., a catheter, cannula, and/or locking mechanism) and a lumen of the puncture member 1768, thereby reducing and/or substantially preventing hemolysis of blood flowing therethrough.

As shown in FIG. 38, the arrangement of the adapter 1760 is such that the puncture member 1768 is disposed at non-orthogonal orientation relative to the shroud 1743. More specifically, at least a portion of the puncture member 1768 extends within an inner volume 1744 of the shroud 1743 and toward an inner surface. Thus, when the fluid reservoir 1760 is inserted into the inner volume 1744 of the shroud 1743, the puncture member 1768 punctures a port 1763 of the fluid reservoir 1760 (e.g., substantially similar to the port 1363 of the fluid reservoir 1360 described above with reference to FIGS. 31-33) at a substantially non-orthogonal angle. For example, the fluid reservoir 1760 can be inserted into the inner volume 1743 of the shroud 1744 with a substantially parallel or orthogonal orientation relative thereto. As the fluid reservoir 1760 is moved in the distal direction, the port 1763 is brought into contact with the puncture member 1768 and with the fluid reservoir 1760 parallel or orthogonal to the shroud 1743, the puncture member 1768 punctures the port 1763 at an angle associated with the orientation of the puncture member 1768 relative to the shroud (e.g., non-orthogonal). Therefore, as shown in FIG. 38, an end portion of the puncture member 1768 can be adjacent to, in contact with, and/or otherwise near an inner surface of the reservoir 1760 defining the inner volume 1764. In this manner, directing the flow of blood to the inner surface reduces a force, which can otherwise result from an impact of the volume of blood contacting the inner surface. Thus, hemolysis of the blood associated with such a contact is reduced or substantially prevented.

Figure 39:
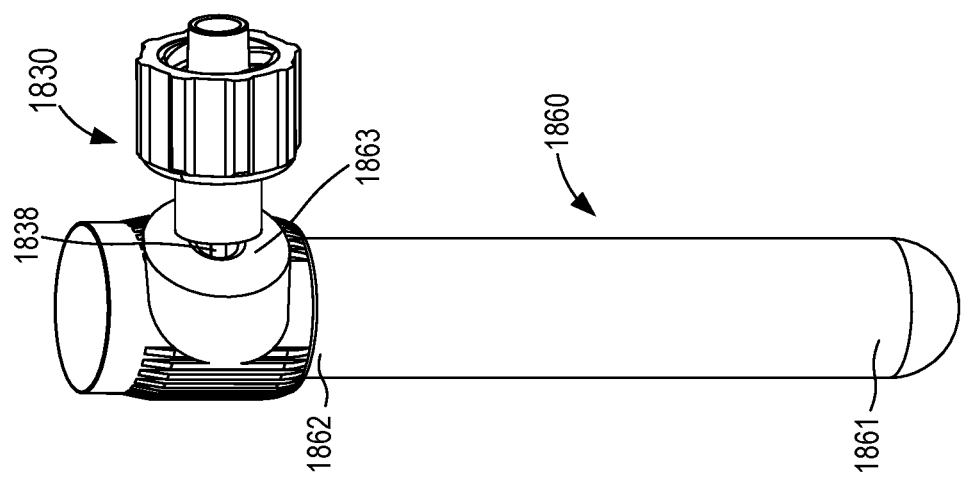
FIG. 39 is a perspective view of an adapter coupled to a fluid reservoir according to another embodiment.

In some embodiments, the adapter 1730 can be configured to engage, for example, a standard fluid reservoir such as, for example, a Vacutainer™ or the like. That is to say, in some embodiments, the adapter 1730 is configured to be compatible with existing fluid reservoirs without modifications being made thereto. In other embodiments, a fluid reservoir can have any suitable configuration. For example, FIG. 39 illustrates an adapter 1830 physically and fluidically coupled to a fluid reservoir 1860 according to another embodiment. The adapter 1830 can be any suitable adapter such as, for example, the adapter 1330 described above with reference to FIGS. 29 and 30. In this manner, the adapter 1830 includes a puncture member 1838 configured to puncture a port or the like of the fluid reservoir 1860, as described in further detail herein.

The fluid reservoir 1860 includes a proximal end portion 1861 and a distal end portion 1862, and defines an inner volume (not shown in FIG. 39). The distal end portion 1862 includes a port 1863 configured to receive, for example, the puncture member 1838 of the adapter 1830, as described in detail above with reference to FIGS. 31-33. The port 1863 in this embodiment, however, is disposed in a substantially horizontal position. More specifically, in some embodiments, the port 1863 can be disposed in a substantially tangential arrangement relative to, for example, an inner surface of the fluid reservoir 1860. Thus, when the puncture member 1838 is inserted through the port 1863, an end portion of the puncture member 1838 can be placed adjacent to, at, or substantially near a portion of the inner surface of the fluid reservoir 1860, as described above with reference to the adapter 1730 and fluid reservoir 1760. Similarly stated, the arrangement of the port 1863 can be such that when the puncture member 1838 is inserted therethrough, at least the end portion of the puncture member 1838 (not shown in FIG. 39) is in a tangential orientation relative to the inner surface of the fluid reservoir 1860. In this manner, directing a flow of blood to the inner surface reduces a force, which can otherwise result from an impact of the volume of blood contacting the inner surface. Thus, hemolysis of the blood associated with such a contact is reduced or substantially prevented.

Figure 42:
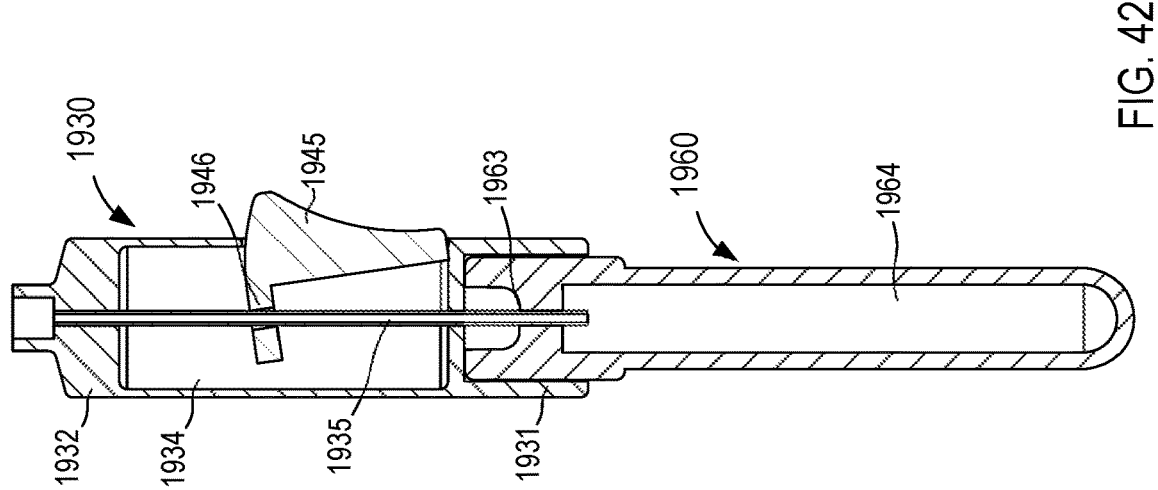
FIGS. 41 and 42 are cross-sectional views of the adapter and the fluid reservoir of FIG. 40, taken along the line 41-41, in a first configuration and a second configuration, respectively.
Figure 41:
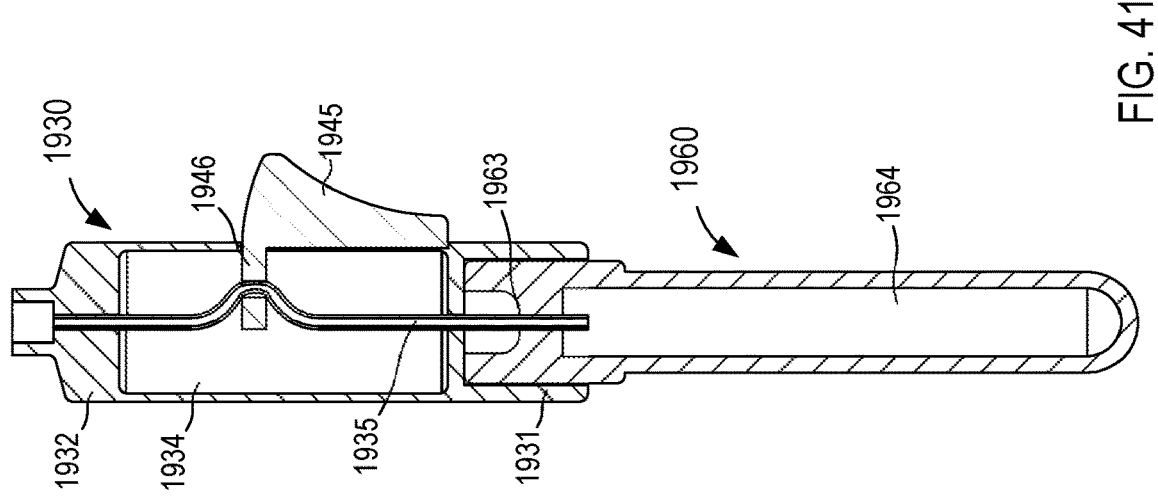
Figure 40:
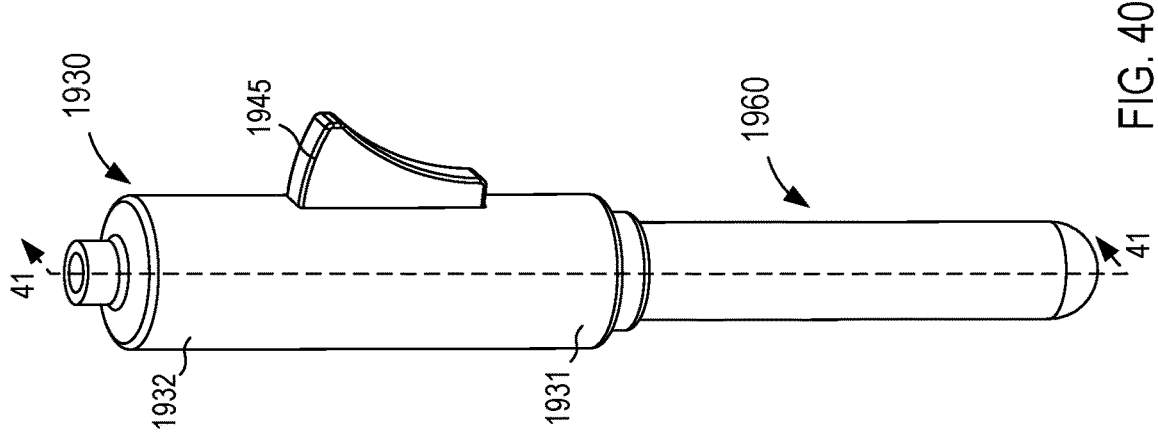
FIG. 40 is a perspective view of an adapter coupled to a fluid reservoir according to another embodiment.

While a flow of bodily-fluid (e.g., blood) into the fluid reservoirs 1360, 1460, 1560, 1660, 1760, and 1860 is described above as being passively controlled by, for example, the flow control members 1367, 1467, 1565, the port 1663, the adapter 1730, and/or the port 1863, respectively, in other embodiments, a flow of bodily-fluid into a fluid reservoir can be actively controlled. That is to say, while the flow of bodily-fluid into the fluid reservoirs 1360, 1460, 1560, 1660, 1760, 1860 is controlled without user intervention (i.e., beyond the intervention of coupling the adapters 1330, 1430, 1530, 1660, 1760, and 1860 to the fluid reservoirs 1360, 1460, 1560, 1660, 1760, and 1860 respectively), in other embodiments, a user can manipulate an adapter and/or fluid reservoir to actively control a flow of fluid into the fluid reservoir. For example, FIGS. 40-42 illustrate an adapter 1930 and a fluid reservoir 1960, according to another embodiment. The fluid reservoir 1960 can be any suitable reservoir that defines an inner volume 1964 configured to receive a flow of bodily fluid such as, for example, an evacuated container or the like. More specifically, as described above with reference to the fluid reservoir 1360 in FIGS. 31-33, the fluid reservoir 1960 includes a port 1963 through which a portion of the adapter 1930 can be inserted to gain access to the inner volume 1964, as described in further detail herein.

As shown in FIGS. 40-42, the adapter 1930 includes a proximal end portion 1931 and a distal end portion 1932, and defines an inner volume 1934. Although not shown, the distal end portion 1932 of the adapter 1930 can be coupled to any suitable lumen-defining device such as a needle, cannula, catheter, and/or sterile flexible tubing. In some embodiments, the distal end portion 1932 can include a locking mechanism or the like that can physically and fluidically couple the adapter 1930 to any suitable corresponding device and/or component. The proximal end portion 1931 of the adapter 1930 receives a portion of the fluid reservoir 1960. For example, as shown in FIGS. 41 and 42, at least a portion of the port 1963 is inserted through the proximal end portion 1931 of the adapter 1930 to be disposed within a portion of the inner volume 1934.

As shown in FIGS. 41 and 42, the adapter 1930 further includes a cannula 1935 and an actuator 1945. Specifically, the cannula 1935 extends through the proximal end portion 1931 and the distal end portion 1932 of the adapter 1930, thereby defining a fluid pathway through the adapter 1930. The cannula 1935 can be any suitable shape, size, or configuration. For example, in some embodiments, the cannula 1935 is a substantially flexible tube formed of a biocompatible plastic or the like. In this manner, at least a portion of the cannula 1935 can be manipulated (e.g., by the actuator 1945) to bend, flex, kink, and/or otherwise reconfigure the cannula 1935, as described in further detail herein. The arrangement of the cannula 1935 can be such that when the fluid reservoir 1960 is inserted into the inner volume 1934 of the adapter 1930, an end portion of the cannula 1935 punctures the port 1963 of the fluid reservoir 1960 and thus, places the inner volume 1964 of the fluid reservoir 1960 in fluid communication with a lumen defined by the cannula 1935. Thus, a negative pressure within the fluid reservoir 1960 (e.g., the fluid reservoir 1960 is an evacuated container) exerts or draws suction through the lumen defined by the cannula 1935, as described in further detail herein.

The actuator 1945 of the adapter 1930 can be any suitable configuration. For example, as shown in FIGS. 41 and 42, the actuator 1945 can be a trigger or the like coupled to the adapter 1930 via a pivot point, pin, axle, etc. More specifically, a first portion of the actuator 1945 extends from and/or beyond an outer surface of the adapter 1930 and a second portion is disposed within the inner volume 1934 defined by the actuator 1930. Thus, a user (e.g., a phlebotomist, doctor, technician, nurse, etc.) can actuate the actuator 1945 by pivoting the actuator 1945 relative to the adapter 1930. In this manner, a portion of the actuator 1945 disposed in the inner volume 1934 of the adapter 1930 can be increased or decreased, for example, by exerting a force or removing a force, respectively, on the actuator 1945 (i.e., pivoting the actuator 1945 relative to the adapter 1930).

As shown, the portion of the actuator 1945 disposed within the inner volume 1934 of the adapter 1930 defines an opening 1946 through which the cannula 1935 can extend. Therefore, actuating the actuator 1945 (e.g., pivoting the actuator 1945 relative to the adapter 1930) results in a corresponding manipulation of a portion of the cannula 1935. For example, in some instances, while the actuator 1945 is in a first configuration, the position of the opening 1946 relative to the adapter 1930 can be such that the cannula 1935 (disposed therein) is pulled, bent, bowed, deformed, kinked, etc. Such deformation of the cannula 1935 can result in, for example, a constriction and/or pinching of the cannula 1935, which in turn, can constrict and/or at least partially obstruct the lumen defined by the cannula 1935, as shown in FIG. 41.

Conversely, a force can be exerted to actuate the actuator 1945, thereby pivoting the actuator 1945 relative to the adapter 1930. As described above, such pivoting motion can, for example, increase a portion of the actuator 1945 disposed in the inner volume 1934, which in turn, can change the position and/or orientation of the opening 1946 relative to the adapter 1930. Thus, the repositioning and/or reorienting of the opening 1946 actively (e.g., by exerting a force) or passively (e.g., by removing or reducing an existing force) reconfigures at least the portion of the cannula 1935 disposed therein. For example, as shown in FIG. 42, when the actuator 1945 is placed in the second configuration, the cannula 1935 can be substantially straight or substantially undeformed. Thus, the lumen defined by the cannula 1935 is substantially unobstructed and/or otherwise not constricted by the actuator 1945.

In use, when the fluid reservoir 1960 is placed in fluid communication with the lumen defined by the cannula 1935 (see e.g., FIGS. 41 and 42), the negative pressure and/or suction (described above) within the lumen of the catheter 1935 can be modulated by actuating the actuator 1945 between its first configuration, associated with a smaller amount of suction, and its second configuration, associated with a larger amount of suction. Moreover, when the distal end portion 1932 of the adapter 1930 is placed in fluid communication with the body of a patient (e.g., either directly or indirectly via a lumen-defining device, a needle, etc.), the negative pressure within the fluid reservoir 1960 draws blood, or other bodily-fluids, through the lumen defined by the cannula 1935 and into the inner volume 1964. In this manner, actuating the actuator 1945 to control or modulate the amount of suction or negative pressure within the lumen of the cannula 1935 can reduce a magnitude of negative pressure that would otherwise be exerted on the flow of blood. Thus, hemolysis of the blood is reduced or substantially prevented that might otherwise result from a rapid exposure to a negative pressure differential produced by the fluid reservoir 1960.

Although the lumen of the cannula 1935 is shown in FIG. 41 as being partially constricted when the actuator 1945 is in its first configuration, in other embodiments, the actuator 1945 can deform the cannula 1935 a sufficient amount to result in a substantially complete constriction of the lumen. Moreover, while not shown in FIGS. 40-42, in some embodiments, the actuator 1945 can include and/or can be operably coupled to a bias member such as a spring or the like. As such, the bias member can exert a force that at least temporarily maintains the actuator 1945 in, for example, the first configuration until an actuating force is exerted on the actuator 1945, which is sufficient to overcome the force of the bias member.

Figure 44:
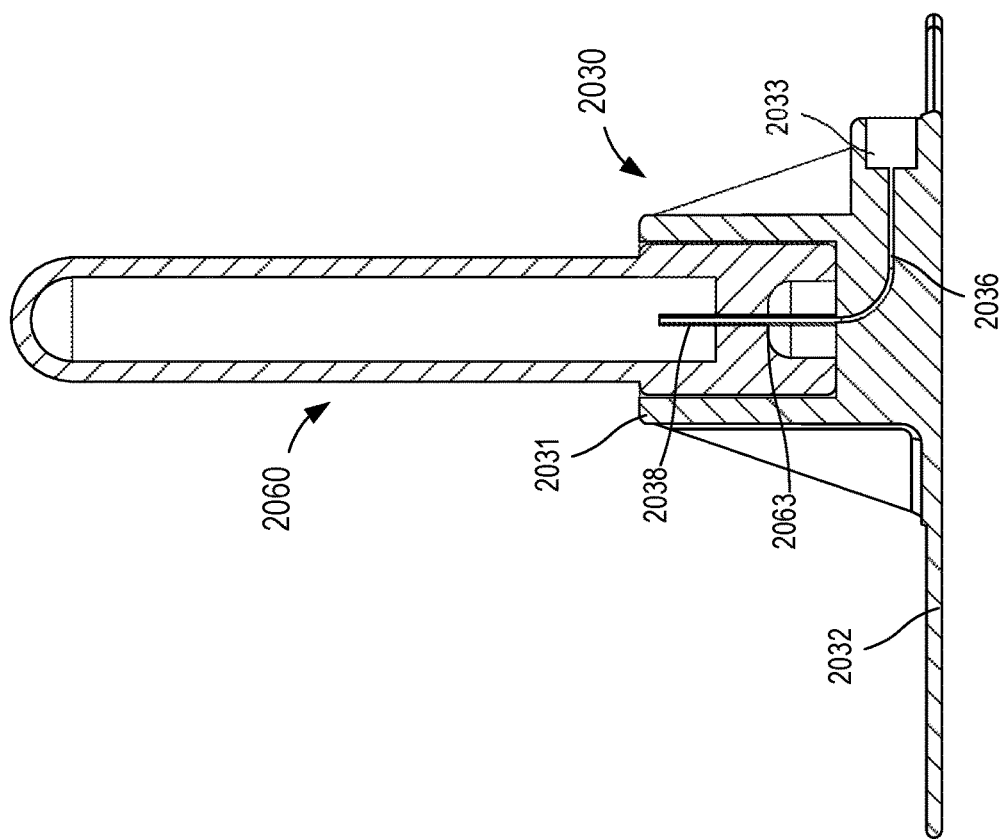
FIG. 44 is a cross-sectional view of the adapter and the fluid reservoir of FIG. 43, taken along the line 44-44.
Figure 43:
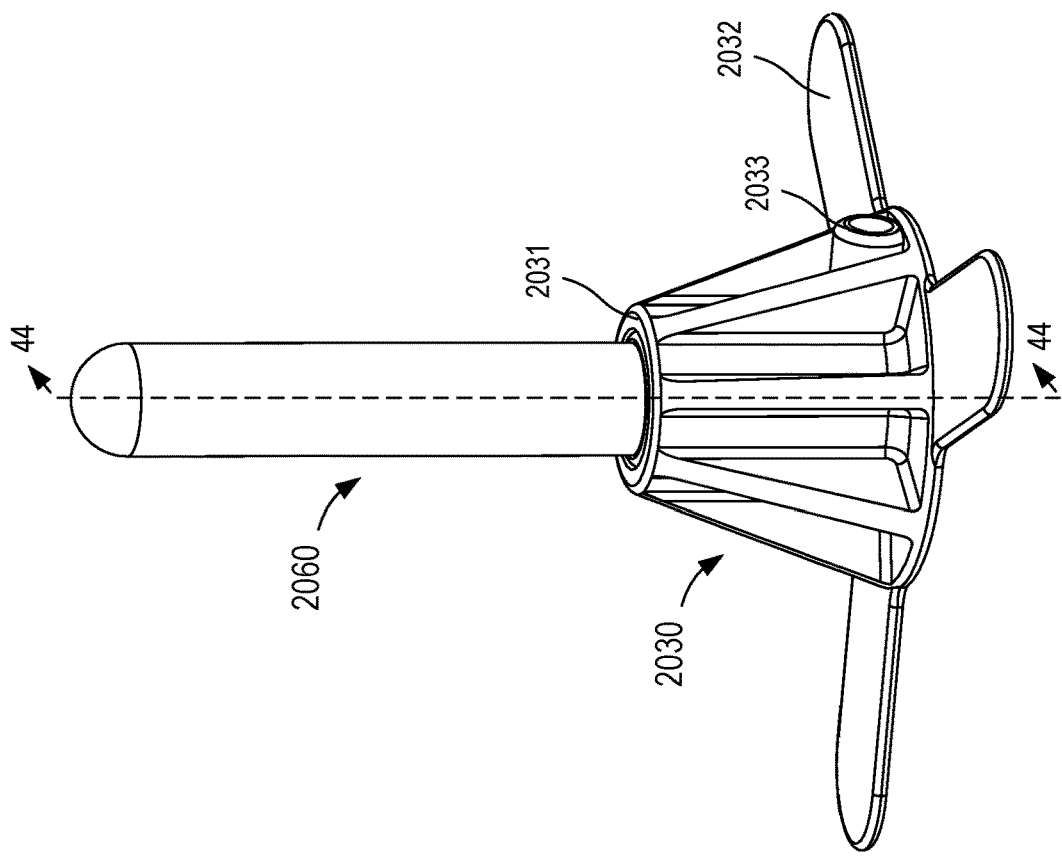
FIG. 43 is a perspective view of an adapter and a fluid reservoir according to another embodiment.

While the adapter 1930 is shown and described above as controlling a flow of bodily fluid into the fluid reservoir 1960 by manipulating the cannula 1935, in other embodiments, an adapter can control a flow of bodily fluid into a fluid reservoir in any suitable manner. For example, FIGS. 43 and 44 illustrate an adapter 2030 and a fluid reservoir 2060, according to another embodiment. The fluid reservoir 2060 can be any suitable reservoir that defines an inner volume 2064 configured to receive a flow of bodily fluid such as, for example, an evacuated container or the like. More specifically, as described above with reference to the fluid reservoir 1360 in FIGS. 31-33, the fluid reservoir 2060 includes a port 2063 through which a portion of the adapter 2030 can be inserted to gain access to the inner volume 2064, as described in further detail herein.

As shown in FIGS. 43 and 44, the adapter 2030 includes a proximal end portion 2031 and a distal end portion 2032. The proximal end portion 2031 of the adapter 2030 is open and/or defines an opening configured to receive at least a portion of the port 2063 of the fluid reservoir 2060. The distal end portion 2032 of the adapter 2030 includes a port 2033 or the like that can be coupled to any suitable lumen-defining device such as a cannula, catheter, and/or sterile flexible tubing (not shown in FIGS. 43 and 44). In some embodiments, the distal end portion 2032 can include a locking mechanism or the like fluidically coupled to the port 2033 and configured to physically and fluidically couple the adapter 2030 to any suitable corresponding device and/or component.

As shown in FIG. 44, the adapter 2030 includes a puncture member 2038 that extends from a surface of the adapter 2030 to, for example, puncture the port 2063 of the fluid reservoir 2060. Furthermore, the adapter 2030 defines a lumen 2036 that extends through a portion of the adapter 2030 to fluidically couple the port 2033 to the puncture member 2038. Thus, the puncture member 2038 can puncture the port 2063 of the fluid reservoir 2060 to place the inner volume 2064 of the fluid reservoir 2060 in fluid communication with, for example, the port 2033 of the adapter 2030, which in turn, can be in fluid communication (e.g., either directly or indirectly via an intervening structure) a portion of the body of a patient. Moreover, a negative pressure within the fluid reservoir 2060 (e.g., the fluid reservoir 2060 is an evacuated container) exerts or draws suction through the lumen 2036 and the port 2033 of the adapter 2030 to, for example, draw a flow of bodily-fluid from the patient through the adapter 2030 and into the inner volume 2064 of the fluid reservoir 2060.

As shown in FIGS. 43 and 44, the arrangement of the adapter 2030 is such that the fluid reservoir 2060 is in a substantially vertical orientation when coupled to the adapter 2030. Thus, when a volume of bodily fluid (e.g., blood) is expelled from the puncture member 2038, in response to the negative pressure within the fluid reservoir 2060, the bodily fluid flows in a substantially vertical direction from a lower position to an upper position. While the fluid reservoir 2060 defines a negative pressure that produces a suction force operable in drawing a flow of bodily-fluid from the puncture member 2038, the bodily-fluid expelled therefrom is also exposed to a substantially opposing force associated with gravitational acceleration (i.e., approximately 9.81 meters-per-second-squared (m/s$^2$). Thus, when a volume of blood is drawn through the adapter 2030 and into the inner volume 2064 of the fluid reservoir 2060, the force associated with gravity acts to slow a velocity of the flow of blood within the inner volume 2064. As such, hemolysis of blood is reduced and/or substantially prevented that can otherwise result from a force associated with a volume of blood impacting an inner surface of the fluid reservoir 2060 defining the inner volume 2064.

Figure 45:
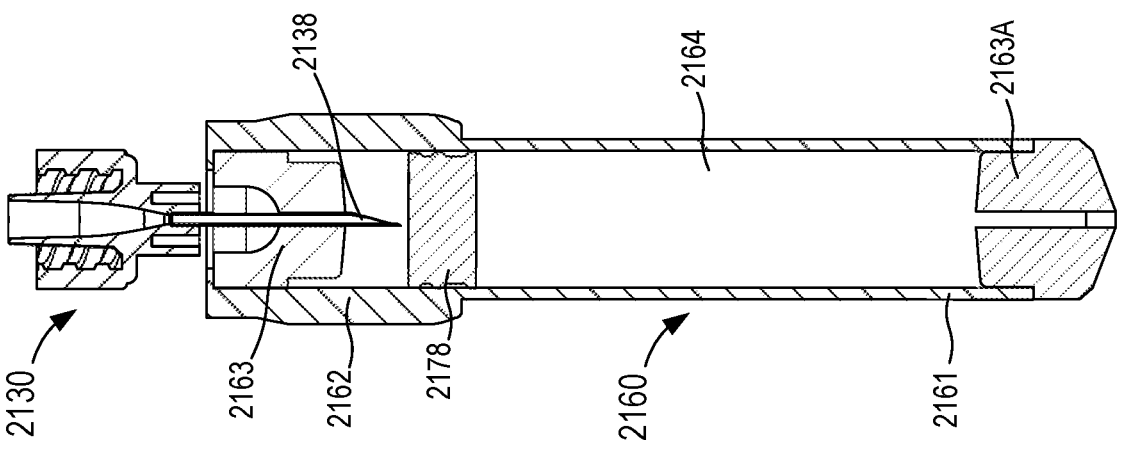
Figure 48:
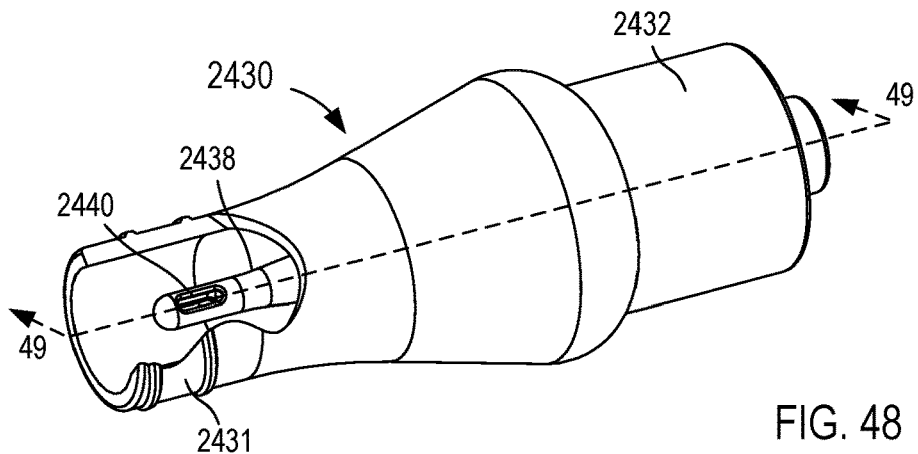
FIG. 48 is a perspective of an adapter included in a bodily-fluid collection device according to another embodiment.

While the adapters and fluid reservoirs described above with reference to FIGS. 27-44 control and/or direct a flow of fluid (i.e., blood) into a fluid reservoir to, for example, reduce hemolysis, in some embodiments, the arrangement of a fluid reservoir and/or an adapter can be such that a negative pressure operable in drawing a volume of blood into the fluid reservoir can be configured modulated and/or controlled. For example, FIGS. 45-60 illustrate embodiments configured to mitigate the risk of hemolysis associated with blood flow to a negative pressure differential within a fluid reservoir. Specifically, FIG. 45 illustrates an adapter 2130 and a fluid reservoir 2160 according to another embodiment. The adapter 2130 can be any suitable adapter such as, for example, the adapter 1330 described above with reference to FIGS. 29 and 30. In this manner, the adapter 2130 includes a puncture member 2138 configured to puncture a port or the like of the fluid reservoir 2160, as described in further detail herein. The fluid reservoir 2160 includes a proximal end portion 2161 and a distal end portion 2162, and defines an inner volume 2164. The proximal end portion 2161 includes a port 2163A configured to receive, for example, an output member (e.g., a needle, puncture member, cannula, etc.) from, for example, a vacuum source or the like, as described in further detail herein. Similarly, the distal end portion 2162 includes a port 2163 configured to receive, for example, the puncture member 2138 of the adapter 2130, as described in detail above with reference to FIGS. 31-33. In some embodiments, the ports 2163A and 2163 can be substantially similar in form and/or function. In some embodiments, the port 2163A disposed at or near the proximal end portion 2161, for example, can include a frangible seal, a self-healing port, a one-way valve, and/or the like.

As shown in FIG. 45, the fluid reservoir 2160 includes an elastomeric member 2178 (and/or any other suitable member or material) disposed within the inner volume 2164. The elastomeric member 2178 is in contact with an inner surface of the fluid reservoir 2160 (defining at least a portion of the inner volume 2164) to form a substantially fluid tight seal therebetween. Thus, a portion of the inner volume 2164 that is proximal to the elastomeric member 2178 is substantially fluidically isolated from a portion of the inner volume 2164 that is distal to the elastomeric member 2178. In some embodiments, the portion of the inner volume 2164 disposed between the elastomeric member 2178 and the port 2163 (i.e., disposed at the distal end portion 2162 of the fluid reservoir 2160) can define, for example, a negative pressure, prior to the insertion of the puncture member 2138 through the port 2163. In other embodiments, both portions of the inner volume 2164 (e.g., on either side of the elastomeric member 2178) define a negative pressure, prior to the insertion of the puncture member 2138 through the port 2163. In still other embodiments, the inner volume 2164, in its entirety, need not define a negative pressure, prior to the insertion of the puncture member 2138 through the port 2163.

As shown in FIG. 45, the plunger 2145 can "float" and/or otherwise be disposed in a substantially fixed position within the inner volume 2164 prior to the port 2163A being fluidically coupled to a vacuum source (not shown in FIG. 45). Moreover, the arrangement of the fluid reservoir 2160 is such that when the actuator 2130 engages the fluid reservoir 2160, the puncture member 2138 is in a distal position relative to the elastomeric member 2178 and thus, substantially fluidically isolated from the portion of the inner volume 2164 that is proximal to the elastomeric member 2178. In a similar manner, the fluid reservoir 2160 can be manipulated such that an outlet of a vacuum source (not shown in FIG. 45) punctures and/or is otherwise inserted through the port 2163A to be placed in fluid communication with the portion of the inner volume 2164 proximal to the elastomeric member 2178. Thus, a user can actuate the vacuum source (e.g., via an electric switch, a pre-charged negative pressure created in a manufacturing process, mechanical actuation, and/or the like), such that the vacuum source draws a vacuum (e.g., a suction force) through its output and into the portion of the inner volume 2164 proximal to the elastomeric member 2178.

In some instances, the suction force and/or negative pressure can be sufficient to overcome a friction force between the elastomeric member 2178 and the inner surface, thereby resulting in a movement of the elastomeric member 2178 within the inner volume 2164 towards the port 2163A. The movement of the elastomeric member 2178 results in a change in volume associated with the portions of the inner volume 2164 disposed on either side of the elastomeric member 2178. In some instances, the increase in volume of the portion of the inner volume 2164 distal to the elastomeric member 2178 results in a negative pressure that is sufficient to draw a flow of bodily-fluid through the puncture member 2138 and into the inner volume 2164. As such, in some instances, a rate and/or magnitude of the vacuum drawn by the vacuum source can be controlled to, for example, change a characteristic associated with a pressure difference within the inner volume 2164 of the fluid reservoir 2160 and, for example, the adapter 2130. Thus, hemolysis of the blood is reduced or substantially prevented that might otherwise result from a rapid exposure to a negative pressure differential produced by the fluid reservoir 2160.

Figure 46:
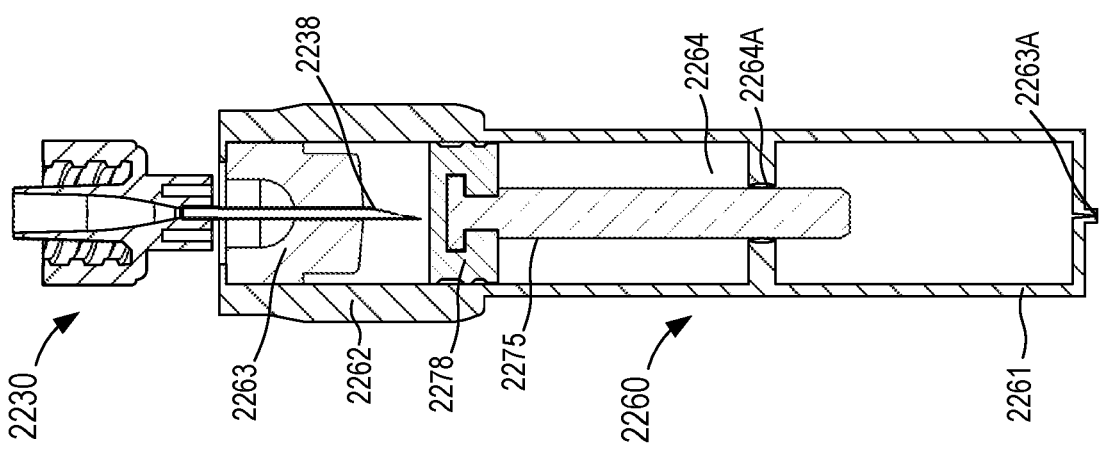

While the elastomeric member 2178 is shown and described above as "floating" within the inner volume 2164, in other embodiments, a fluid reservoir can include an elastomeric member and/or the like that is coupled to a plunger. For example, FIG. 46 illustrates an adapter 2230 and a fluid reservoir 2260 according to another embodiment. The adapter 2230 can be any suitable adapter such as, for example, the adapter 1330 described above with reference to FIGS. 29 and 30. In this manner, the adapter 2230 includes a puncture member 2238 configured to puncture a port or the like of the fluid reservoir 2260, as described in further detail herein.

The fluid reservoir 2260 includes a proximal end portion 2261 and a distal end portion 2262, and defines an inner volume 2264. The proximal end portion 2261 includes a port 2263A configured to be coupled to, for example, a vacuum source or the like, as described in further detail herein. Similarly, the distal end portion 2262 includes a port 2263 configured to receive the puncture member 2238 of the adapter 2230, as described in detail above with reference to FIGS. 31-33. In some embodiments, the ports 2263A and 2263 can be substantially similar in form and/or function. In some embodiments, the port 2263A disposed at or near the proximal end portion 2261, for example, can include a frangible seal, a self-healing port, a one-way valve, a locking mechanism, and/or the like. Thus, the port 2263A can physically and fluidically couple to a corresponding outlet port of a vacuum source (not shown in FIG. 46). For example, in some embodiments, an outlet port of a vacuum source and the port 2263A can form a threaded coupling or the like. In such embodiments, when the vacuum source is actuated, the port 2263A can be transitioned from a first, substantially sealed configuration to a second, substantially open configuration.

As shown in FIG. 46, the fluid reservoir 2260 includes a plunger 2275 disposed within the inner volume 2264. The plunger 2275 includes and/or is coupled to an elastomeric member 2278 disposed within the inner volume 2264. The elastomeric member 2278 is in contact with an inner surface of the fluid reservoir 2260 (defining at least a portion of the inner volume 2264) to form a substantially fluid tight seal therebetween. Thus, a portion of the inner volume 2264 that is proximal to the elastomeric member 2278 is substantially fluidically isolated from a portion of the inner volume 2264 that is distal to the elastomeric member 2278, as described above with reference to the elastomeric member 2178 in FIG. 46. In this embodiment, at least a portion of the plunger 2275 is movably disposed within a support member 2264A extending from a surface of the fluid reservoir 2260. As shown, the support member 2264A can, for example, divide the inner volume into a first portion and a second portion. Moreover, the support member 2264A can include a seal or the like that is in contact with an outer surface of the plunger to form a substantially fluid tight seal therebetween. Thus, the first portion of the inner volume 2264 can be substantially isolated from the second portion of the inner volume 2264.

The arrangement of the fluid reservoir 2260 is such that when the actuator 2230 engages the fluid reservoir 2260, the puncture member 2238 is in a distal position relative to the elastomeric member 2278 and thus, substantially fluidically isolated from the portion of the inner volume 2264 that is proximal to the elastomeric member 2278. A user can similarly manipulate the fluid reservoir to couple the port 2263A to an outlet of a vacuum source (not shown in FIG. 46). In this manner, the portion of the inner volume 2264 that is proximal to the support member 2264A is placed in fluid communication with the vacuum source. Thus, a user can actuate the vacuum source (e.g., via an electric switch, a pre-charged negative pressure created in a manufacturing process, mechanical actuation, and/or the like) such that the vacuum source draws a vacuum (e.g., a suction force) through its output and into the portion of the inner volume 2264 proximal to the support member 2264A.

In some instances, the suction force and/or negative pressure can be sufficient to move the plunger 2275 within the inner volume 2264 towards the port 2263A. The movement of the plunger 2275 results in a corresponding movement of the elastomeric member 2278 and thus, changes a volume associated with the portions of the inner volume 2264 disposed on either side of the elastomeric member 2278. In some instances, the increase in volume of the portion of the inner volume 2264 distal to the elastomeric member 2278 results in a negative pressure that is sufficient to draw a flow of bodily-fluid through the puncture member 2238 an into the inner volume 2264. As such, in some instances, a rate and/or magnitude of the vacuum drawn by the vacuum source can be controlled to, for example, change a characteristic associated with a pressure difference within the inner volume 2264 of the fluid reservoir 2260 and, for example, the adapter 2230. Thus, hemolysis of the blood is reduced or substantially prevented that might otherwise result from a rapid exposure to a negative pressure differential produced by the movement of the plunger 2375 within the fluid reservoir 2260.

In some embodiments, the arrangement of the plunger 2275 and the support member 2264A can, for example, maintain a sterility of a portion of the inner volume 2264 distal to the support member 2264A. Specifically, as described above, the support member 2264A can include the seal that engages the outer surface of the plunger 2275 to fluidically isolate a portion of the inner volume 2264 proximal to the support member 2264A from a different portion of the inner volume 2264 distal to the support member 2264A. As such, when the port 2263A is placed in fluid communication with the vacuum source (not shown in FIG. 46), the portion of the inner volume 2264 proximal to the support member 2264A can be exposed, for example, to a non-sterile environment (e.g., associated with the vacuum source), while the sterility of the portion of the inner volume 2264 is maintained.

Figure 47:
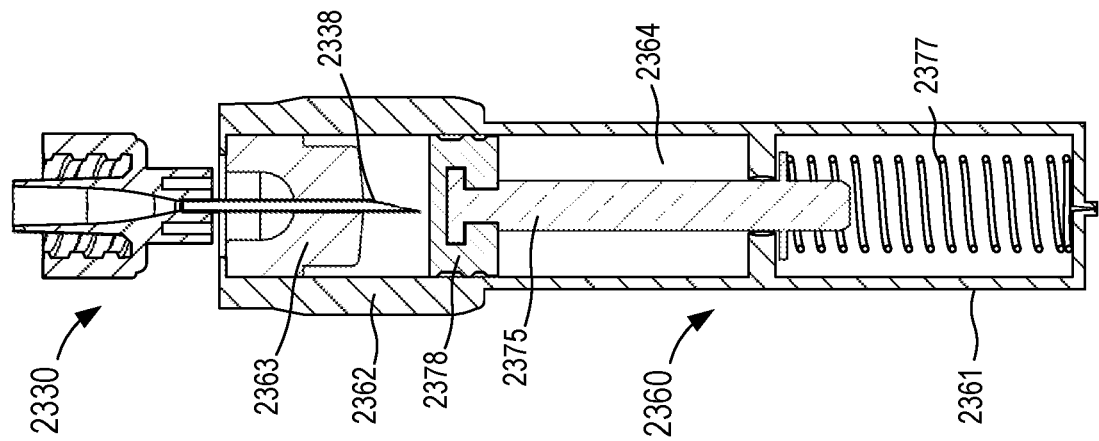
FIGS. 45-47 are cross-sectional views of an adapter and a fluid reservoir each according to a different embodiment.

FIG. 47 illustrates an adapter 2330 and a fluid reservoir 2360 according to another embodiment. The adapter 2330 can be any suitable adapter such as, for example, the adapter 1330 described above with reference to FIGS. 29 and 30. In this manner, the adapter 2330 includes a puncture member 2338 configured to puncture a port or the like of the fluid reservoir 2360, as described in further detail herein.

The fluid reservoir 2360 includes a proximal end portion 2361 and a distal end portion 2362, and defines an inner volume 2364. The proximal end portion 2361 includes a port 2363A configured to be coupled to, for example, a vacuum source or the like, as described in further detail herein. Similarly, the distal end portion 2362 includes a port 2363 configured to receive the puncture member 2338 of the adapter 2330, as described in detail above with reference to FIGS. 31-33. As shown in FIG. 47, the fluid reservoir 2360 includes a plunger 2375 disposed within the inner volume 2364. The plunger 2375 includes and/or is coupled to an elastomeric member 2378 disposed within the inner volume 2364. The elastomeric member 2378 is in contact with an inner surface of the fluid reservoir 2360 (defining at least a portion of the inner volume 2364) to form a substantially fluid tight seal therebetween. As such, the fluid reservoir 2360 can be substantially similar to the fluid reservoir 2260 described above with reference to FIG. 46.

The fluid reservoir 2360 can differ from the fluid reservoir 2260, however, by including a bias member 2377 (e.g., a linear spring, a torsion spring, a leaf spring, a compression member, and/or the like) disposed about and in contact with a portion of the plunger 2375. In this manner, when the port 2363A is physically and fluidically coupled to an outlet of a vacuum source (not shown in FIG. 47) and the vacuum source is actuated, the vacuum source draws a vacuum (e.g., a suction force) through its output and into the portion of the inner volume 2364. Thus, the vacuum source can exert a suction force within a portion of the inner volume 2364 that results in a proximal movement of the plunger 2375. The arrangement of the bias member 2377, however, is such that the bias member 2377 exerts a reaction force in response to the movement of the plunger 2375. As such, the bias member 2377 can at least partially control a movement of the plunger 2375 within the inner volume 2364, for example, to reduce speed at which the plunger 2375 is moved. Thus, hemolysis of the blood is reduced or substantially prevented that might otherwise result from a rapid exposure to a negative pressure differential produced by the movement of the plunger 2375 within the fluid reservoir 2360.

Figure 49:
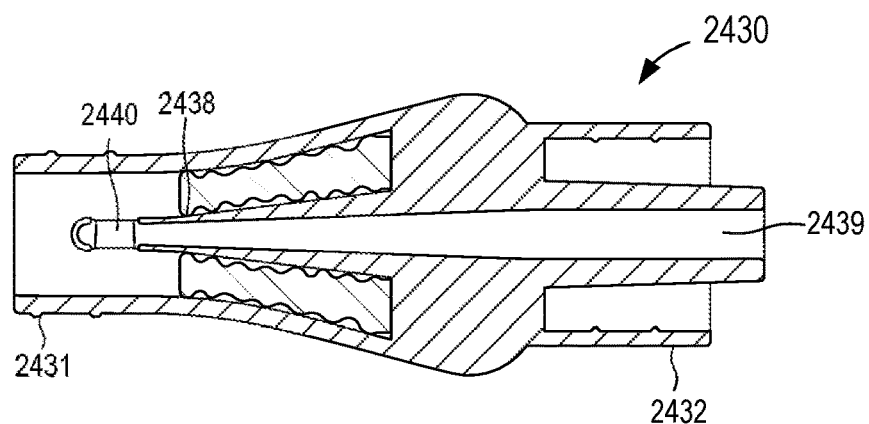
FIG. 49 is a cross-sectional view of the adapter of FIG. 48, taken along the line 49-49.
Figure 50:
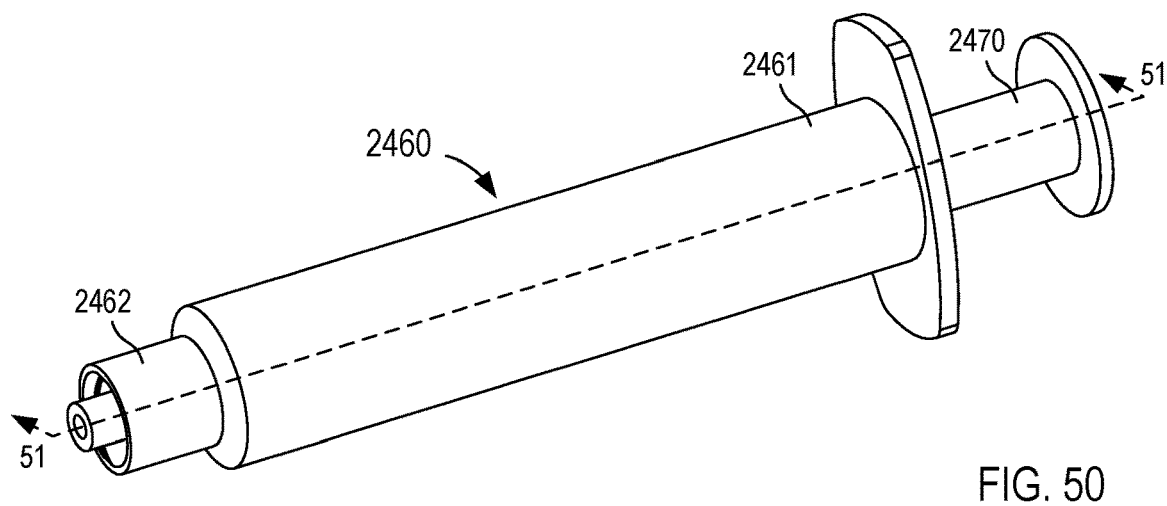
FIG. 50 is a perspective view of a fluid reservoir included in a bodily-fluid collection device according to an embodiment.

While the adapters in the embodiments above have been shown and described as being physically and/or fluidically coupled to a corresponding fluid reservoir configured as an evacuated container, in other embodiments, an adapter can be configured to physically and/or fluidically couple to any suitable fluid reservoir and/or any suitable intervening structure. For example, FIGS. 49 and 50 illustrate an adapter 2430 according to another embodiment. The adapter 2430 can be any suitable shape or size and can be configured to be placed in fluid communication with any suitable fluid reservoir. For example, as described in further detail herein with reference to FIGS. 51 and 52, in some instances, the adapter 2430 can be physically and fluidically coupled to a fluid reservoir 2460 configured as, for example, a syringe or the like.

As shown in FIGS. 49 and 50, the adapter 2430 has a proximal end portion 2431 and a distal end portion 2432. In this embodiment, the distal end portion 2432 of the adapter 2430 includes, for example, a locking mechanism (e.g., a Luer Lok® or the like) that can physically and fluidically couple the adapter 2430 to a corresponding locking mechanism of any other suitable device such as, for example, an extension set or the like. In other embodiments, the distal end portion 2432 can be any suitable configuration such as, for example, a port, a septum, and/or the like. In a similar manner, the proximal end portion 2431 of the adapter 2430 includes, for example, a locking mechanism (e.g., a Luer Lok® or the like) that can physically and/to fluidically couple the adapter 2430 to, for example, the fluid reservoir 2460, as described in further detail herein.

The adapter 2430 includes a delivery member 2438 that extends from a portion of adapter 2430 toward the proximal end portion 2431. The delivery member 2438 defines a lumen 2439 extending at least partially through the delivery member 2438. More specifically, in this embodiment, the lumen 2439 extends through the distal end portion 2432 of the adapter 2430 but does not extend through the proximal end portion 2431. Similarly stated, the lumen 2439 does not extend through a proximal surface of the delivery member 2438. For example, as shown in FIGS. 49 and 50, the delivery member 2438 can have a substantially rounded or hemispherical proximal surface that is substantially closed and/or continuous. Alternatively, the delivery member 2438 defines at least one opening 2440 disposed along a circumference of the delivery member 2438 at a position distal to, for example, the proximal surface. Thus, while the delivery member 2438 does not define an opening though a proximal most surface, opening(s) 2440 place a proximal end portion of the lumen 2439 in fluid communication with a volume outside of the delivery member 2438.

Figure 51:
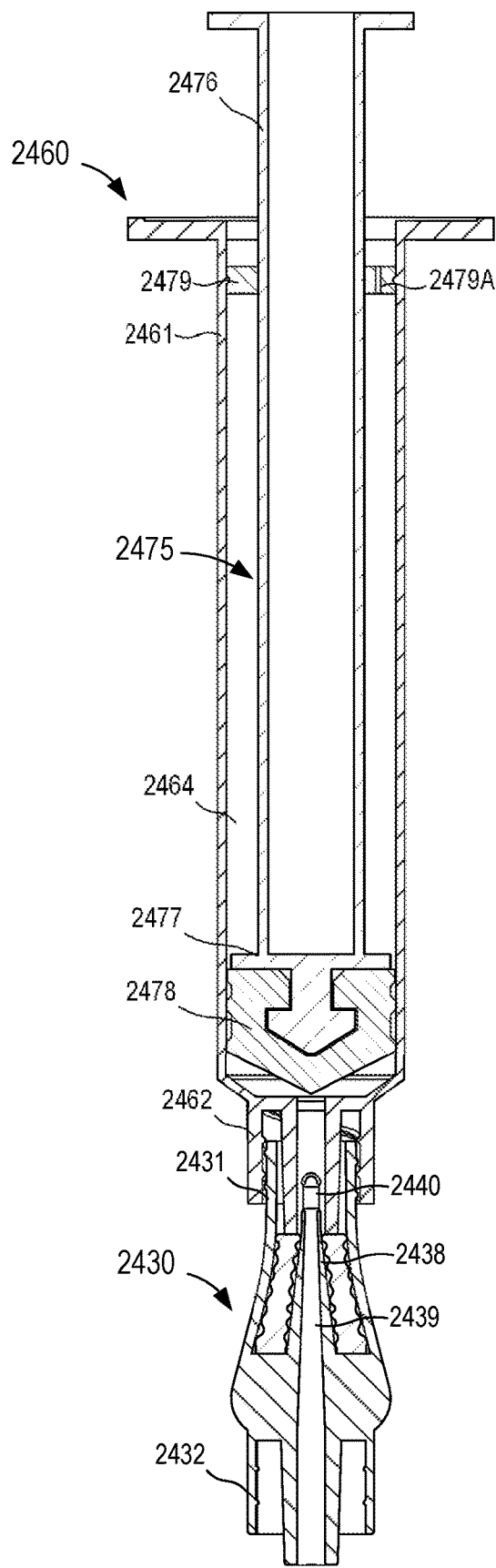
FIG. 51 is a cross-sectional view of the adapter illustrated in FIG. 49 coupled to the fluid reservoir illustrated in FIG. 50, taken along the line 51-51 in FIG. 50.
Figure 52:
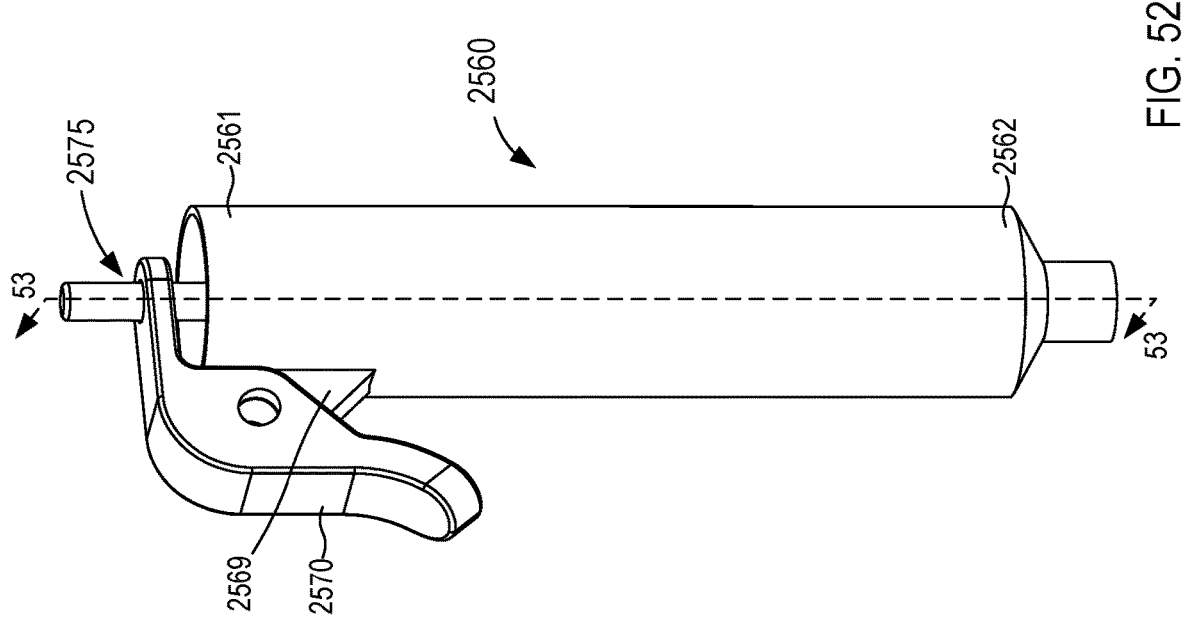
FIG. 52 is a perspective view of a fluid reservoir included in a bodily-fluid collection device according to another embodiment.

As described above, the adapter 2430 can be physically and fluidically coupled to the fluid reservoir 2460 (see e.g., FIG. 52). The fluid reservoir 2460 can be any suitable shape, size, or configuration. For example, in this embodiment, the fluid reservoir 2460 is a syringe or the like, as shown in FIG. 51. The fluid reservoir 2460 has a proximal end portion 2461 and a distal end portion 2462 and defines an inner volume 2464. The distal end portion 2462 is configured to be physically and fluidically coupled to an adapter such as, for example, the adapter 2430. For example, the distal end portion 2462 can include a locking mechanism (e.g., a Luer Lok® or the like) configured to be physically and fluidically coupled to the proximal end portion 2431 (e.g., the corresponding locking member included therein) of the adapter 2430. Moreover, when the adapter 2430 is coupled to the fluid reservoir 2460, the delivery member 2438 is at least partially disposed in the inner volume 2464 of the fluid reservoir 2460 and as such, the opening(s) 2440 defined by the delivery member 2438 place the lumen 2439 of the adapter 2430 in fluid communication with the inner volume 2464 of the fluid reservoir 2460, as described in further detail herein.

As shown in FIGS. 51 and 52, the proximal end portion 2461 movably receives a plunger 2475 that is at least partially disposed in the inner volume 2464, as described in further detail herein. As shown in FIG. 52, the fluid reservoir 2460 includes a seal member 2479 disposed within the inner volume 2464. More specifically, the seal member 2479 is disposed within a proximal portion of the inner volume 2464 and about a portion of the plunger 2475. As such, the seal member 2479 forms a substantially fluid tight seal between an inner surface of the fluid reservoir 2460 and an outer surface of the seal member 2479 and an outer surface of the plunger 2475 and an inner surface of the seal member 2479. Furthermore, the seal member 2479 defines an opening 2479A extending therethrough that can place a portion of the inner volume 2464 proximal to the seal member 2479 in fluid communication with a portion of the inner volume 2464 distal to the seal member 2479. The arrangement of the fluid reservoir 2460 is such that the seal member 2479 is maintained in a substantially fixed position when the plunger 2475 is moved within the inner volume 2464, as described in further detail herein.

As shown in FIG. 52, the plunger 2475 has a proximal end portion 2476 and a distal end portion 2477. The distal end portion 2477 of the plunger 2475 includes and/or is coupled to an elastomeric member 2478 or the like. For example, in some embodiments, the elastomeric member 2478 can form a substantially fluid tight seal with an inner surface of the fluid reservoir 2460. As described above, the plunger 2475 is movably disposed within the inner volume 2464 of the fluid reservoir 2460. More specifically, the plunger 2475 can be moved within the inner volume 2464 in an axial direction between a first position (e.g., a distal position) and a second position (e.g., a proximal position) relative to the fluid reservoir 2460. For example, in some embodiments, the plunger 2475 can be disposed in a distal position relative to the fluid reservoir 2460 prior to use. A user can then manipulate the fluid reservoir 2460 and/or the plunger 2475 to move the plunger 2474 in a proximal direction within the inner volume 2464. With the elastomeric member 2478 in contact with the inner surface of the fluid reservoir 2460, the proximal movement of the plunger 2475 relative to the fluid reservoir 2460 produces a negative pressure within a portion of the inner volume 2464 that is distal to the elastomeric member 2478.

When the adapter 2430 is coupled to the fluid reservoir 2460 (as shown in FIG. 52), the negative pressure within the portion of the inner volume 2464 results in a suction through the lumen 2439 of the delivery member 2438. Thus, when the distal end portion 2431 of the adapter 2430 is coupled to a device or other intervening structure, which in turn, is in fluid communication with a portion of the body and/or intervening device (e.g. catheter, fluid reservoir, etc.), the suction force within the lumen 2439 can draw a bodily-fluid (e.g., blood) through the lumen 2439 and into the inner volume 2464 of the fluid reservoir 2460. Moreover, the arrangement of the seal member 2479 within the inner volume 2464 can reduce, limit, modulate, and/or otherwise at least partially control a rate at which the plunger 2479 can be moved within the inner volume 2464. For example, with the elastomeric member 2478 forming a substantially fluid tight seal with the inner surface of the fluid reservoir 2460, the proximal movement of the plunger 2464 reduces and/or compresses a volume defined between the elastomeric member 2478 and the seal member 2479, which in turn, increases a pressure within that volume. Therefore, with the seal member 2479 similarly forming a substantially fluid tight seal with the inner surface of the fluid reservoir 2460 and with an outer surface of the plunger 2475, air within the volume between the seal member 2479 and the elastomeric member 2478 is forced through the opening 2479A defined by the seal member 2479, thereby limiting the rate at which the plunger 2479 is moved within the inner volume 2464. As such, a negative pressure and/or a suction force drawn through the lumen 2439 of the adapter 2430 is correspondingly controlled and/or modulated.

As described above, in some embodiments, the arrangement of the delivery member 2438 can also limit and/or otherwise modulate a pressure and/or a suction force within the lumen 2439. In this manner, when withdrawing a volume of blood, hemolysis of the blood flowing through the lumen 2439 and into the inner volume 2464 of the fluid reservoir 2460 is reduced or substantially prevented. Specifically, the arrangement opening(s) 2440 and the lumen 2439 of the delivery member 2438 can, for example, reduce a negative pressure within the lumen 2439 and/or can slow a flow of blood delivered to the inner volume 2464 of the fluid reservoir 2460 to an extent that can reduce and/or substantially prevent hemolysis of the blood that can otherwise result from, inter alia, a volume of blood being exposed to a rapid pressure drop or the like. In addition, the arrangement of an inner surface defining the lumen 2439 can, for example, reduce turbulence, eddy currents, and/or any other disturbance that can otherwise result from a discontinuity or the like.

Figure 53:
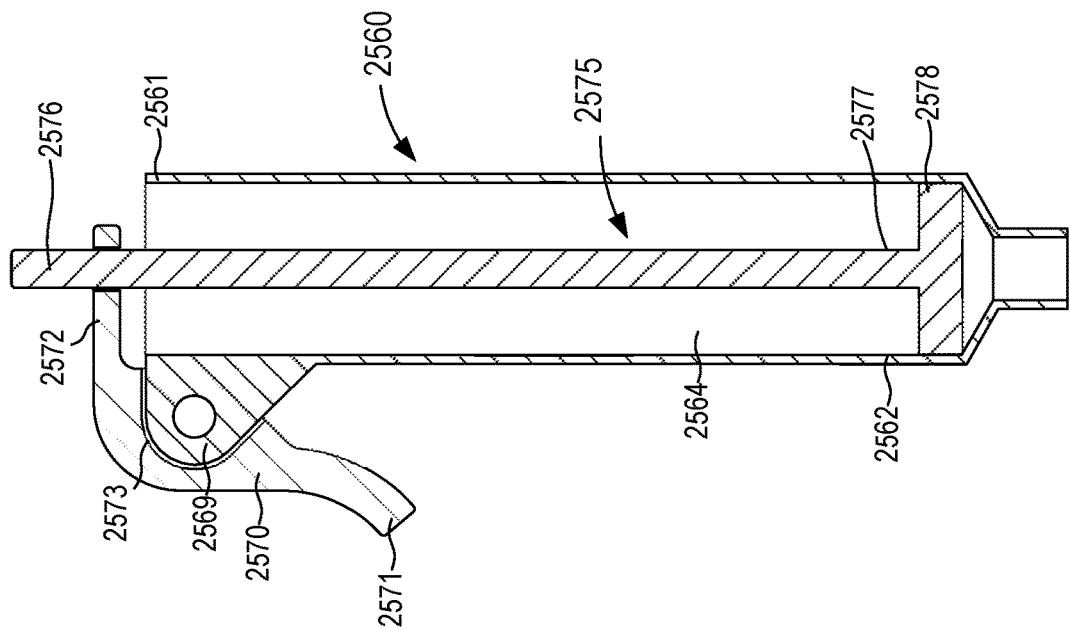
FIG. 53 is a cross-sectional view of the fluid reservoir of FIG. 52, taken along the line 53-53.
Figure 54:
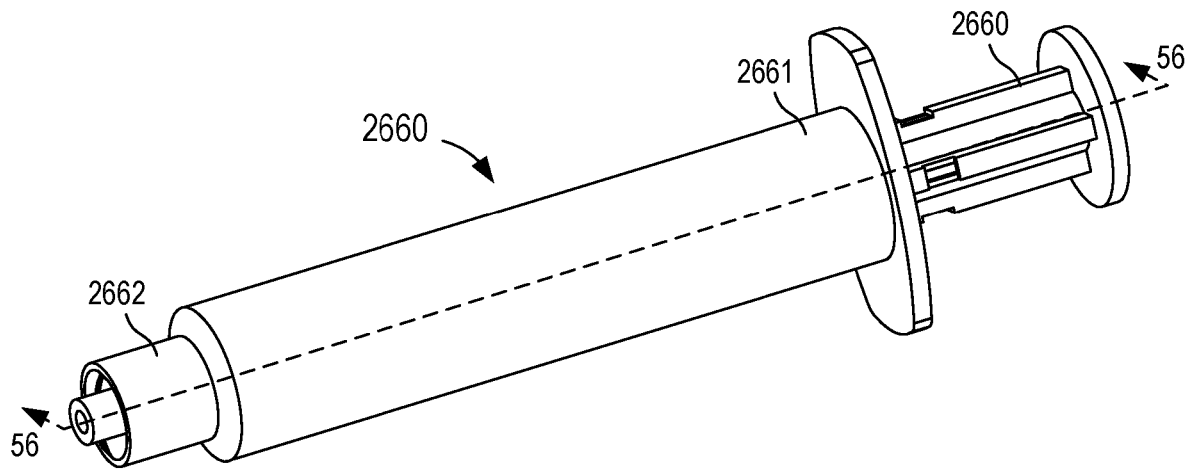
FIG. 54 is a perspective view of a fluid reservoir included in a bodily-fluid collection device according to another embodiment.

While the fluid reservoir 2460 is particularly shown and described above with reference to FIGS. 51 and 52, in other embodiments, any suitable fluid reservoir can be coupled to, for example, the adapter 2430 to receive a volume of blood with reduced hemolysis of its constituents. For example, FIGS. 53 and 54 illustrate a fluid reservoir 2560 according to another embodiment. In this embodiment, the fluid reservoir 2560 is, for example, a syringe or the like having a proximal end portion 2561 and a distal end portion 2562 and defining an inner volume 2564. The distal end portion 2562 is configured to be physically and fluidically coupled to an adapter such as, for example, the adapter 1530, as described in detail above.

The proximal end portion 2561 of the fluid reservoir 2560 is substantially open and receives at least a portion of a plunger 2575. Moreover, the proximal end portion 2561 of the fluid reservoir 2560 includes an actuator 2570 that is operable in moving the plunger 2575 within the inner volume 2564. For example, as shown in FIGS. 53 and 54, the fluid reservoir 2560 includes a protrusion 2569 to which the actuator 2570 is pivotally coupled. More specifically, the actuator 2570 includes a first end portion 2571, a second end portion 2572, and a pivot portion 2573 disposed therebetween. The second end portion 2572 of the actuator 2570 is coupled to a portion of the plunger 2575, as described in further detail herein. The pivot portion 2573 is coupled to the protrusion 2569 via, for example, a pin, an axle, a rod, and/or the like configured to allow the actuator 2570 to pivot about the protrusion 2569 (e.g., about an axis defined by the protrusion 2569) in response to a force exerted on the first end portion 2571. In this manner, the actuator 2570 can be arranged, for example, as a trigger or the like which when actuated, is operable in moving the plunger 2575 relative to the fluid reservoir 2560, as described in further detail herein.

As shown in FIG. 54, the plunger 2575 has a proximal end portion 2576 and a distal end portion 2577. The distal end portion 2577 of the plunger 2575 includes and/or is coupled to an elastomeric member 2578 or the like. For example, in some embodiments, the elastomeric member 2578 can form a substantially fluid tight seal with an inner surface of the fluid reservoir 2560. As described above, the plunger 2575 is movably disposed within the inner volume 2564 of the fluid reservoir 2560. More specifically, the proximal end portion 2576 of the plunger 2575 is coupled to the second end portion 2572 of the actuator 2570 such that an actuation of the actuator 2570 results in a movement of the plunger 2570 within the inner volume 2564.

For example, a user can exert a force on the first end portion 2571 (e.g., with his or her thumb or finger) of the actuator 2570, which in turn, results in a pivoting motion about the protrusion 2569 that places the first end portion 2571 in a position closer to an outer surface of the fluid reservoir 2560 and places the second end portion 2572 in a corresponding position farther away from the fluid reservoir 2560. In other words, the pivoting of the actuator 2570 about the protrusion 2569 moves the second end portion 2572 in a proximal direction. Moreover, the trigger arrangement of the actuator 2570 (as described above) defines a range of motion through which the actuator 2570 can pivot and thus, defines a range of motion through which the plunger 2575 is moved in the proximal direction (i.e., a stroke length). As such, the user can serially actuate the actuator 2570 to move the plunger 2575 a desired distance in the proximal direction.

With the elastomeric member 2578 of the plunger 2575 forming a substantially fluid tight seal with the inner surface of the fluid reservoir 2560, the proximal movement of the plunger 2575 relative to the fluid reservoir 2560 produces a negative pressure within a portion of the inner volume 2564 that is distal to the elastomeric member 2578. Thus, when the fluid reservoir is coupled to an adapter and/or any other suitable lumen-defining device in fluid communication with the body of a patient, the negative pressure results in a suction force within that lumen that can draw a bodily fluid (e.g., blood) through the lumen and into the inner volume 2564 of the fluid reservoir 2560. Moreover, by limiting the stroke length (as described above) of the plunger 2575, a rate at which the plunger 2575 can be moved within the inner volume 2564 is reduced, limited, modulated, and/or otherwise at least partially controlled. As a result, a negative pressure and/or a suction force drawn through, for example, the lumen of the lumen-defining device is correspondingly controlled and/or modulated. Therefore, by limiting the stroke of the plunger 2575, a negative pressure within the inner volume 2564 of the fluid reservoir 2560 and/or a rate at which blood (or other bodily-fluid) flows into the inner volume 2564 can be controlled to an extent that can reduce and/or substantially prevent hemolysis of the blood that can otherwise result from, inter alia, a volume of blood being exposed to a rapid pressure drop or the like.

While the actuator 2570 is particularly shown in FIGS. 52 and 53, in other embodiments, the actuator 2570 can be any suitable device, mechanism, and/or member that is operative in moving the plunger 2575 within the fluid reservoir 2560. For example, while actuator 2570 is described above as being actuated by a user's thumb or finger, in other embodiments, and actuator can include a first end portion that extends a given length of the fluid reservoir as to be engaged by a user's palm or more than one finger (e.g., each finger excluding the thumb of the user). In other embodiments, a fluid reservoir can include an actuator that is a switch, a push button, a toggle, and/or the like configured to close an electric circuit or the like when actuated. Thus, when the electric circuit is closed, a current can flow through the electric circuit, for example, to a mechanism (e.g., including an electric motor) configured to move a plunger within the fluid reservoir.

Figure 55:
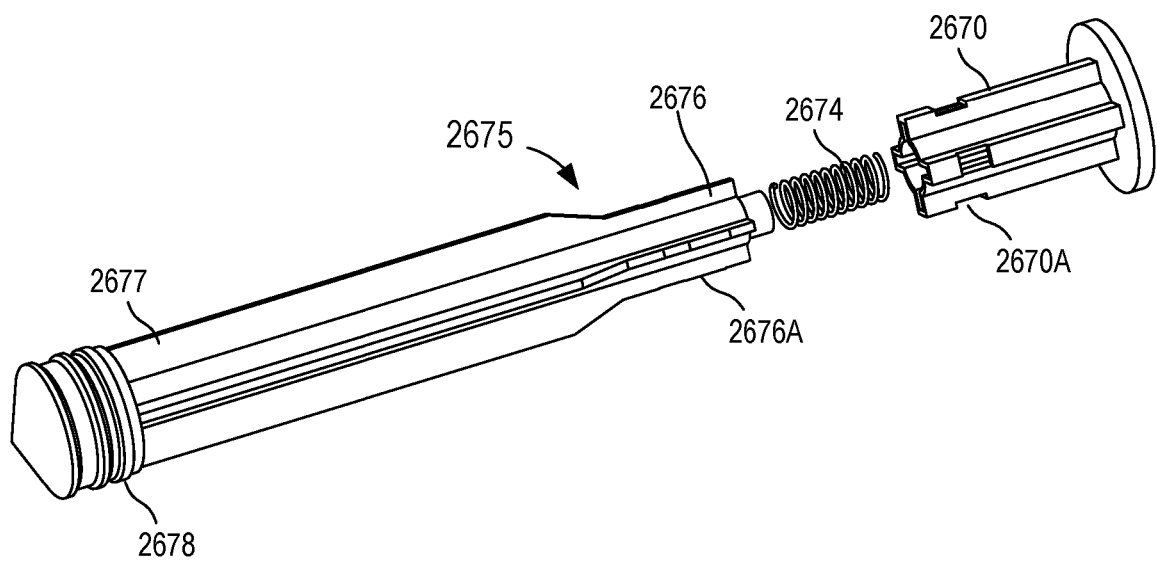
FIG. 55 is an exploded view of a plunger included in the fluid reservoir of FIG. 54.
Figure 56:
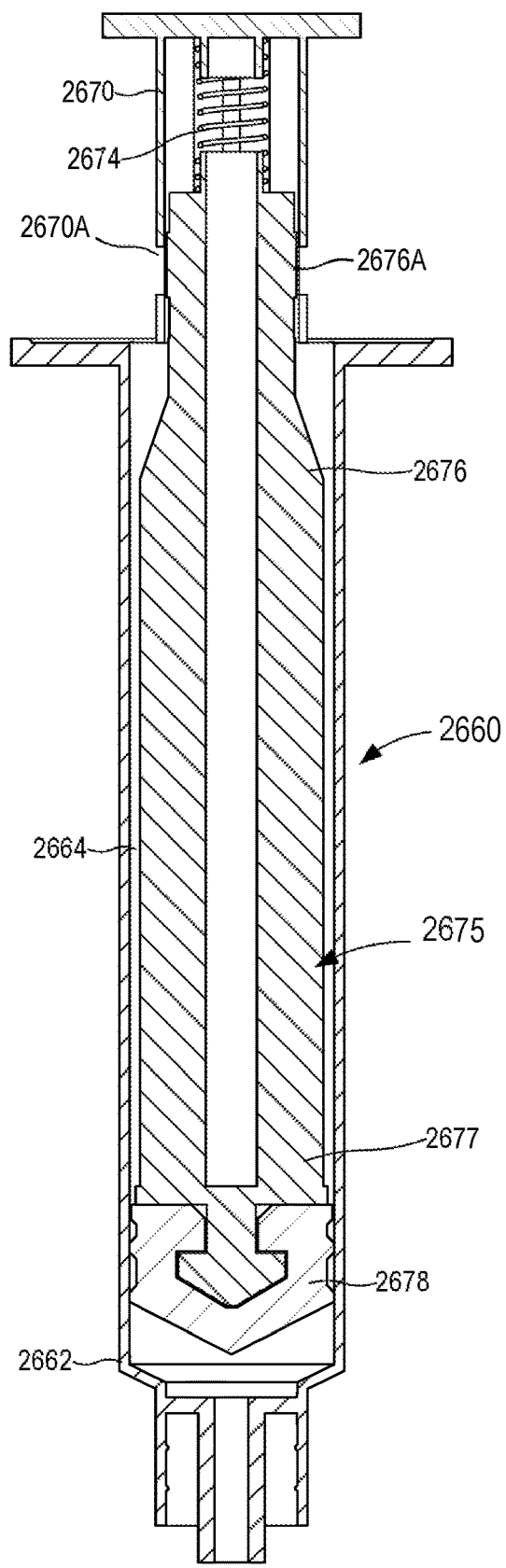
FIG. 56 is a cross-sectional view of the fluid reservoir of FIG. 54, taken along the line 56-56.

FIGS. 54-56 illustrate a fluid reservoir 2660 according to another embodiment. The fluid reservoir 2660 can be any suitable shape, size, or configuration. For example, in this embodiment, the fluid reservoir 2660 is a syringe or the like, as shown in FIG. 54. The fluid reservoir 2660 has a proximal end portion 2661 and a distal end portion 2662 and defines an inner volume 2664 (see e.g., 56). The distal end portion 2662 is configured to be physically and fluidically coupled to an adapter (not shown in FIGS. 54-56) such as, for example, the adapter 2430 described above with reference to FIGS. 48-51.

The proximal end portion 2661 of the fluid reservoir 2660 movably receives a plunger 2675 that is at least partially disposed in the inner volume 2664. As shown in FIGS. 55 and 56, the plunger 2675 has a proximal end portion 2676 and a distal end portion 2677. The distal end portion 2677 of the plunger 2675 includes and/or is coupled to an elastomeric member 2678 or the like. For example, in some embodiments, the elastomeric member 2678 can form a substantially fluid tight seal with an inner surface of the fluid reservoir 2660, as described in detail above. The proximal end portion 2676 of the plunger 2675 is coupled to an actuator 2670. For example, in some embodiments, at least a portion of the actuator 2670 can be hollow and configured to be movably disposed (e.g., in an axial direction) about the proximal end portion 2676 of the plunger 2675. Expanding further, the proximal end portion 2676 of the plunger 2675 includes a set of protrusions 2676A or the like (e.g., tabs, pins, bumps, etc.) configured to engage and/or otherwise disposed in a corresponding set of openings 2670A when the actuator 2670 is disposed about the proximal end portion 2676. In some embodiments, each protrusion 2676A can include an indicator or the like that can be viewable when disposed in a corresponding opening 2670A of the actuator 2670, as described in further detail herein.

As shown in FIGS. 55 and 56, the plunger 2675 includes a bias member 2674 (e.g., a linear spring, a torsion spring, and/or the like) disposed between the proximal end portion 2676 and the actuator 2670. In this manner, the bias member 2674 can, for example, maintain the actuator 2670 is a substantially fixed position relative to the proximal end portion 2676 until a force is exerted on the actuator 2670 or the plunger 2675 that is sufficient to overcome a force exerted by the bias member 2674. For example, in some embodiments, a user can manipulate the fluid reservoir 2660 to fluidically couple the distal end portion 2662, for example, to an adapter (e.g., the adapter 2430), which in turn can be directly or indirectly coupled to a device in fluid communication with a portion of the body. Thus, the inner volume 2664 of the fluid reservoir 2660 is placed in fluid communication with the portion of the body. With the fluid reservoir 2660 in fluid communication with the portion of the body, the user can manipulate the actuator 2670, for example, to move the plunger 2675 within the inner volume 2664. For example, a user can exert a force on the actuator 2670 to move the actuator 2670 and the plunger 2675 in the proximal direction relative to the fluid reservoir 2660. The arrangement of the bias member 2674 can be such that at least a portion of the force exerted by the user on the actuator 2670 transitions the bias member 2674 from a first configuration (e.g., a compressed configuration) to a second configuration (e.g., an extended configuration). Thus, the bias member 2674 can absorb at least a portion of the force (e.g., an excess portion of force above a predetermined threshold), exerted by the user, that would otherwise be exerted on the plunger 2675. In this manner, a rate at which the plunger 2675 is moved within the inner volume 2664 can be at least partially controlled and/or otherwise limited, which in turn, can reduce and/or substantially prevent hemolysis of the blood drawn into the inner volume 2664 that can otherwise result from, inter alia, a volume of blood being exposed to a rapid pressure drop or the like.

In some embodiments, the arrangement of the protrusions 2676A of the proximal end portion 2676 within the openings 2670A of the actuator 2670, for example, can define a range of motion of the actuator 2670 relative to the plunger 2675 (e.g., can prevent a movement of the actuator 2675 beyond a predetermined threshold relative to the plunger 2675. In some embodiments, the protrusions 2676A can each include an indicator or the like that are viewable through the openings 2670A and therefore, can provide an indication to the user associated with the movement of the actuator 2670 relative to the plunger 2675. For example, in some embodiments, when a force is exerted on the actuator 2670 that is greater than a predetermined threshold, the actuator 2670 can be moved relative to the plunger 2675 and at least a portion of the force can transition the bias member 2674 from its first configuration to its second configuration. Thus, when the bias member 2674 is in its second configuration (e.g., an extended configuration), the actuator 2670 can be in a position relative to the plunger 2675 that is associated with at least a portion of the indicator of the protrusions 2676A being viewable through the openings 2670A. As such, the indicators can provide a visual indication of when a force exerted by the user exceeds a predetermined threshold. In some embodiments, the arrangement of the protrusions 2676A and the openings 2670A can be such that when a force exerted on the actuator 2670 exceeds the predetermined threshold, the plunger 2675 and/or the actuator 2670 also provide an auditory (e.g., a clicking sound) or a haptic indication.

Figure 58:
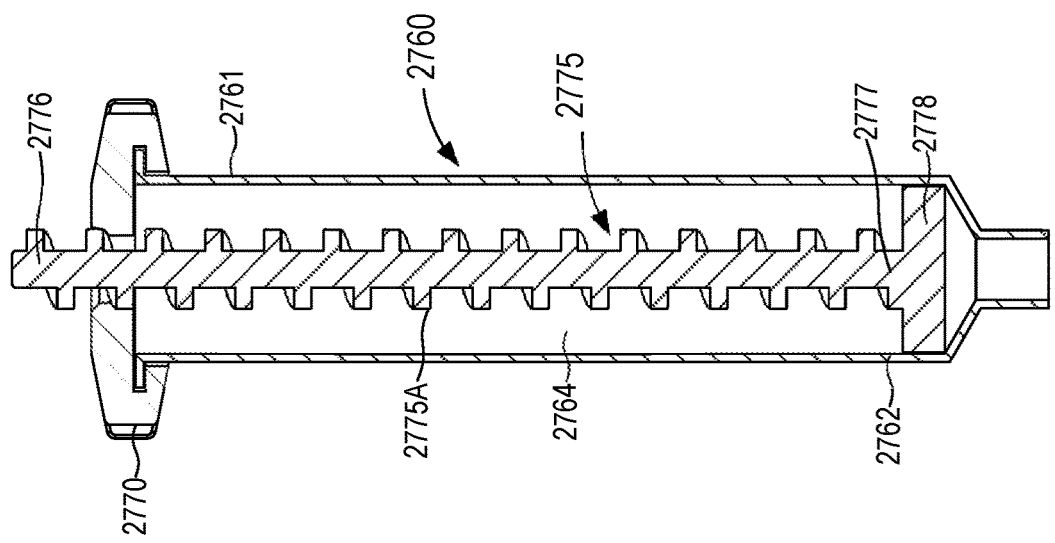
FIG. 58 is a cross-sectional view of the fluid reservoir of FIG. 57, taken along the line 58-58.
Figure 57:
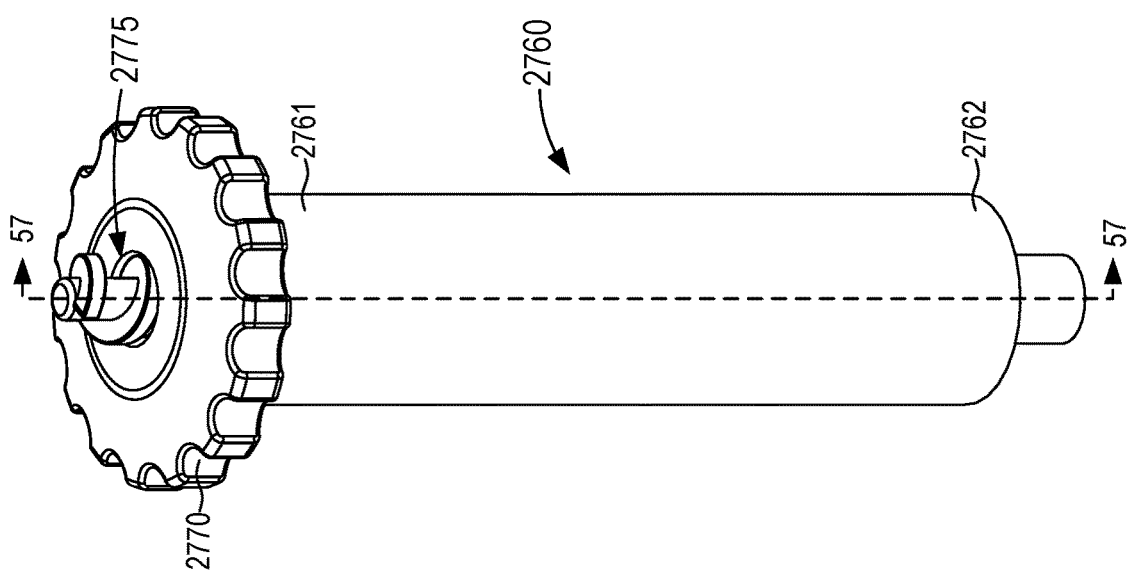
FIG. 57 is a perspective view of a fluid reservoir included in a bodily-fluid collection device according to another embodiment.

While the actuators 2570 and 2670 are particularly shown and described above, in other embodiments, a fluid reservoir can include any suitable actuator operable in moving a plunger within an inner volume of the fluid reservoir. For example, FIGS. 57 and 58 illustrate a fluid reservoir 2760 according to another embodiment. The fluid reservoir 2760 can be any suitable shape, size, or configuration. For example, in this embodiment, the fluid reservoir 2760 is a syringe or the like, as shown in FIG. 57. The fluid reservoir 2760 has a proximal end portion 2761 and a distal end portion 2762 and defines an inner volume 2764 (see e.g., 56). The distal end portion 2762 is configured to be physically and fluidically coupled to an adapter (not shown in FIGS. 57 and 58) such as, for example, the adapter 2430 described above with reference to FIGS. 48-51. The proximal end portion 2761 of the fluid reservoir 2760 movably receives a plunger 2775 that is at least partially disposed in the inner volume 2764. As shown in FIG. 58, the plunger 2775 has a proximal end portion 2776 and a distal end portion 2777. The distal end portion 2777 of the plunger 2775 includes and/or is coupled to an elastomeric member 2778 or the like, as described in detail herein. The proximal end portion 2776 of the plunger 2775 is coupled to an actuator 2770 operable in moving the plunger 2775 relative to the fluid reservoir 2760.

The actuator 2770 can be any suitable shape, size, or configuration. For example, as shown in FIGS. 57 and 58, the actuator 2770, in this embodiment, is a dial rotatably coupled to the fluid reservoir 2760 and the plunger 2775. More specifically, the actuator 2770 can be disposed about the proximal end portion 2761 of the fluid reservoir 2760 such that the actuator 2770 can rotate relative thereto without, for example, unthreading or removing the actuator 2770 from the fluid reservoir 2760. In other words, the actuator 2770 can be coupled to the proximal end portion 2761 of the fluid reservoir 2760 for rotational motion while substantially preventing a linear motion of the actuator 2770 relative to the fluid reservoir 2760. As shown in FIG. 58, an outer surface of the plunger 2775 includes and/or otherwise forms a set of continuous threads 2775A arranged in a helical manner along a length of the plunger 2775 (e.g., substantially the entire length). Moreover, a portion of the plunger 2775 is configured to extend through, for example, a threaded opening defined by the actuator 2770. Thus, the set of threads 2775A engage a surface of the actuator 2770 to define a threaded coupling therebetween, which can allow the plunger 2775 to be moved in an axial direction within the inner volume 2764 of the fluid reservoir 2760.

Specifically, in use, the fluid reservoir 2760 can be manipulated to couple the distal end portion 2762 to an adapter or other device in fluid communication with a portion of the body, thereby placing the inner volume 2764 of the fluid reservoir 2760 in fluid communication with the portion of the body and/or intervening device (e.g. catheter, etc.). With the inner volume 2764 in fluid communication with the portion of the body, the actuator 2770 can be rotated relative to the fluid reservoir 2760, which in turn, results in the threads 2775A being advanced along a surface of the actuator 2770. Thus, the plunger 2775 is moved in an axial direction (e.g., a proximal direction) within the inner volume 2764, which in turn, increases a portion of the inner volume 2764 that is distal to the elastomeric member 2778. Such an increase results in, for example, a negative pressure within the portion of the inner volume 2764 distal to the elastomeric member 2778 and therefore, a suction force is exerted that is operable in drawing a bodily-fluid (i.e., blood) into the inner volume 2764 of the fluid reservoir 2760. In some embodiments, the arrangement of the actuator 2770 and the plunger 2775 (i.e., the threaded coupling) limits a rate at which the plunger 2775 is moved within the inner volume 2764. In this manner, limiting the rate at which the plunger 2775 is moved within the inner volume 2764 can reduce and/or substantially prevent hemolysis of the blood drawn into the inner volume 2764 that can otherwise result from, inter alia, a volume of blood being exposed to a rapid pressure drop or the like.

Figure 59:
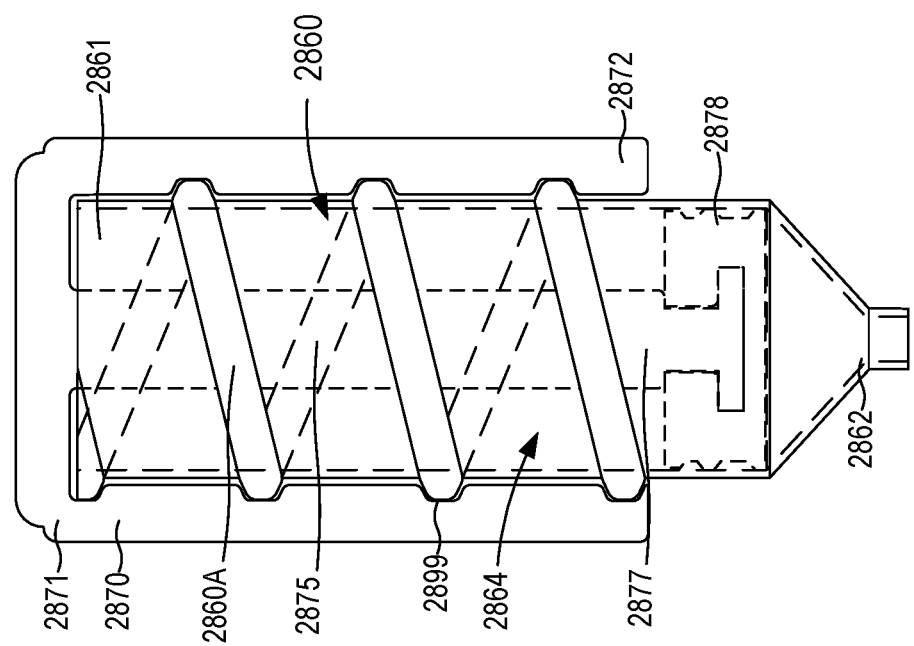
FIG. 59 is a front view of a fluid reservoir included in a bodily-fluid collection device according to another embodiment.

While the actuator 2770 is shown and described above as forming a threading coupling with the plunger 2775, in other embodiments, a fluid reservoir can include an actuator that is monolithically formed with a plunger. For example, FIG. 59 illustrates a fluid reservoir according to another embodiment. The fluid reservoir 2860 has a proximal end portion 2861 and a distal end portion 2862 and defines an inner volume 2864. The distal end portion 2862 is configured to be physically and fluidically coupled to an adapter (not shown in FIG. 59) such as, for example, the adapter 2430 described above with reference to FIGS. 48-51. In this embodiment, the fluid reservoir 2860 includes an outer surface that defines a set of continuous threads arranged in a helical manner along a length of the fluid reservoir 2860, as described above with reference to the plunger 2775 in FIG. 58.

The fluid reservoir 2860 is rotatably coupled to an actuator 2870. The actuator 2870 includes a proximal end portion 2871, a distal end portion 2872, and a plunger 2875. The actuator 2870 further includes an inner surface that defines a set of continuous threads 2899 (e.g., female threads or grooves) arranged in a helical manner along a length of the inner surface. In this manner, the actuator 2870 can be disposed about the fluid reservoir 2860 such that the set of threads 2860A of the fluid reservoir 2860 are disposed within the corresponding set of threads 2899 of the actuator 2870, while the plunger 2875 extends from the proximal end portion 2871 of the actuator 2870 within the inner volume 2864 of the fluid reservoir 2860. Moreover, as shown in FIG. 59, a distal end portion 2877 of the plunger 2875 includes and/or is coupled to an elastomeric member 2878 configured to form a substantially fluid tight seal with an inner surface of the fluid reservoir 2860, as described in detail herein.

Thus, in use, the fluid reservoir 2860 can be manipulated to couple the distal end portion 2862 to an adapter or other device in fluid communication with a portion of the body, thereby placing the inner volume 2864 of the fluid reservoir 2860 in fluid communication with the portion of the body. With the inner volume 2864 in fluid communication with the portion of the body, the actuator 2870 can be rotated relative to the fluid reservoir 2860, which in turn, results in the threads 2899 of the actuator 2870 being advanced along the corresponding threads 2860A of the fluid reservoir 2860. Thus, the actuator 2870 can be moved in the proximal direction relative to the fluid reservoir 2860, which results in the plunger 2875 being moved in an axial direction (e.g., a proximal direction) within the inner volume 2864. As such, a portion of the inner volume 2864 that is distal to the elastomeric member 2878 is increased. Such an increase results in, for example, a negative pressure within the portion of the inner volume 2864 distal to the elastomeric member 2878 and therefore, a suction force is exerted that is operable in drawing a bodily-fluid (i.e., blood) into the inner volume 2864 of the fluid reservoir 2860. In some embodiments, the arrangement of the actuator 2870 and the fluid reservoir 2860 (i.e., the threaded coupling) limits a rate at which the plunger 2875 is moved within the inner volume 2864. In this manner, limiting the rate at which the plunger 2875 is moved within the inner volume 2864 can reduce and/or substantially prevent hemolysis of the blood drawn into the inner volume 2864 that can otherwise result from, inter alia, a volume of blood being exposed to a rapid pressure drop or the like.

Figure 60:
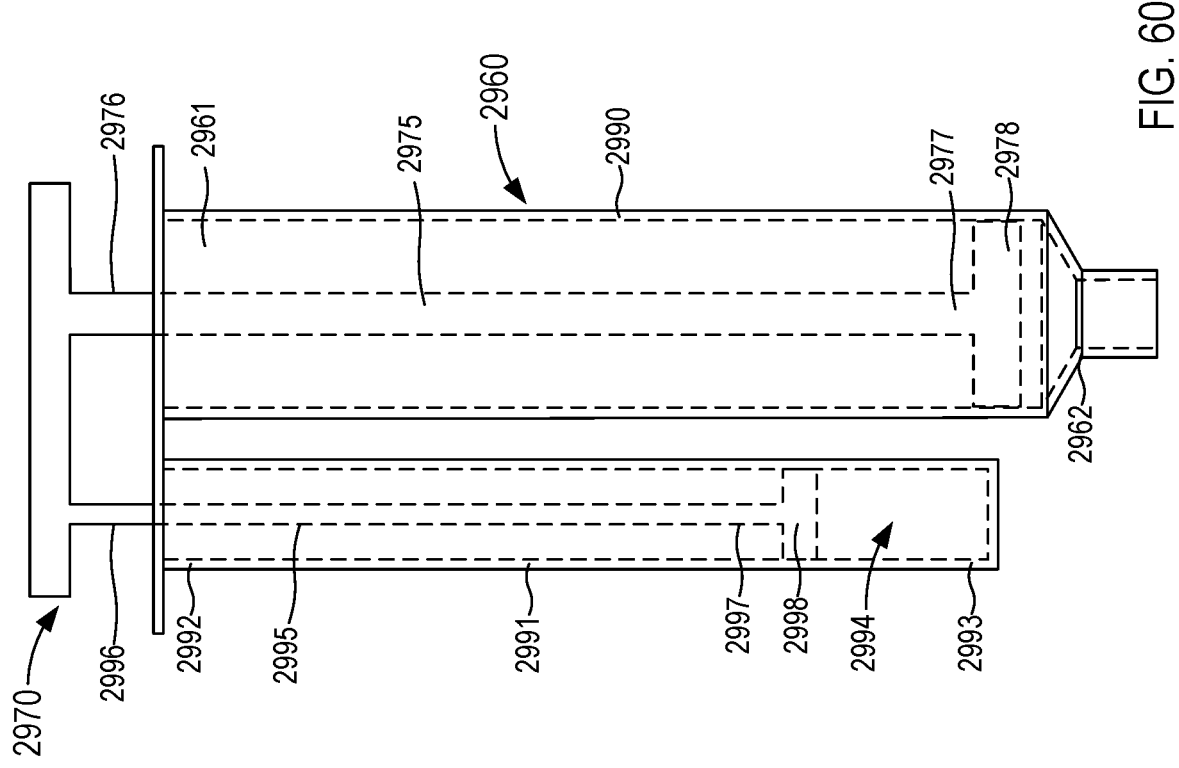
FIG. 60 is a cross-sectional view of a fluid reservoir included in a bodily-fluid collection device according to another embodiment.

FIG. 60 illustrates a fluid reservoir 2960 according to another embodiment. The fluid reservoir 2960 can be any suitable shape, size, or configuration. For example, in this embodiment, the fluid reservoir 2960 can be configured to receive a portion of an actuator 2970 (e.g., arranged as a syringe or the like), as described in further detail herein. The fluid reservoir 2960 has a first chamber 2990 and a second chamber 2991, which are formed unitarily (e.g., joined at a proximal end portion of the fluid reservoir 2960. The first chamber 2990 includes a proximal end portion 2961 and a distal end portion 2962 and defines an inner volume 2964. The distal end portion 2962 is configured to be physically and fluidically coupled to an adapter such as, for example, the adapter 2430 described above with reference to FIGS. 48-51. The proximal end portion 2961 movably receives a first plunger 2975 of the actuator 2970, which is at least partially disposed in the inner volume 2964, as described in further detail herein. In this manner, the first chamber 2990 is configured to receive and at least temporarily store a volume of bodily fluid, as described in further detail herein.

Similarly, the second chamber 2991 includes a proximal end portion 2992 and a distal end portion 2993 and defines an inner volume 2994. The distal end portion 2993 of the second chamber 2991 is closed (i.e., does not define a port or other opening). The proximal end portion 2992 movably receives a second plunger 2995 of the actuator 2970, which is at least partially disposed in the inner volume 2994, as described in further detail herein. As shown in FIG. 60, the second chamber 2991 has a size and/or shape that are/is smaller than the first chamber 2990. Thus, in some embodiments, the second chamber 2991 can be an auxiliary chamber or the like. For example, with the distal end portion 2993 of the second chamber 2991 being closed and/or sealed, in this embodiment, the second chamber 2991 can act as a dampener or the like configured to dampen a movement of the actuator 2970 relative to the fluid reservoir 2960.

As described above, the actuator 2970 includes the first plunger 2975 movably disposed in the inner volume 2964 of the first chamber 2990 and the second plunger 2995 movably disposed in the inner volume 294 of the second chamber 2991. As shown in FIG. 60, the first plunger 2975 has a proximal end portion 2976 and a distal end portion 2977. The proximal end portion 2976 of the first plunger 2975 is coupled to and/or otherwise unitarily formed a proximal end portion 2996 of the second plunger 2995. The distal end portion 2977 of the first plunger 2975 includes and/or is coupled to an elastomeric member 2978 or the like. In some embodiments, the elastomeric member 2978 can form a substantially fluid tight seal with an inner surface of the first chamber 2990, as described in detail above. Similarly, the second plunger 2995 has the proximal end portion 2996 and a distal end portion 2997. The proximal end portion 2996 of the second plunger 2995 is coupled to and/or otherwise unitarily formed with the proximal end portion 2976 of the first plunger 2975. The distal end portion 2997 of the second plunger 2995 includes and/or is coupled to an elastomeric member 2998. As described above with reference to the elastomeric member 2978, the elastomeric member 2998 of the second plunger 2995 can form a substantially fluid tight seal with an inner surface of the second chamber 2991. In this manner, the actuator 2970 can be moved relative to the fluid reservoir 2960 to move the first plunger 2975 within the inner volume 2964 of the first chamber 2990 and the second plunger 2995 within the inner volume 2994 of the second chamber 2991 in a substantially concurrent movement, as described in further detail herein.

In use, for example, the fluid reservoir 2960 can be manipulated to couple the distal end portion 2962 to an adapter or other device in fluid communication with a portion of the body, thereby placing the inner volume 2964 of the fluid reservoir 2960 in fluid communication with the portion of the body and/or intervening device (e.g. catheter, etc.). Once the inner volume 2964 is placed in fluid communication with the portion of the body, the actuator 2970 can be moved in the proximal direction relative to the fluid reservoir 2960, which in turn, moves the first plunger 2975 within the inner volume 2964. More specifically, with the elastomeric member 2978 of the plunger 2975 forming a substantially fluid tight seal with the inner surface of the fluid reservoir 2960, the proximal movement of the first plunger 2975 relative to the fluid reservoir 2960 produces a negative pressure within a portion of the inner volume 2964 that is distal to the elastomeric member 2978. Thus, when the fluid reservoir is coupled to an adapter and/or any other suitable lumen-defining device in fluid communication with the body of a patient, the negative pressure results in a suction force within that lumen that can draw a bodily fluid (e.g., blood) through the lumen and into the inner volume 2964 of the fluid reservoir 2960.

In a similar manner, the proximal movement of the actuator 2970 moves the second plunger 2995 within the inner volume 2994 of the second chamber 2991 substantially concurrently with the first plunger 2975, thereby increasing a portion of the inner volume 2994 that is distal to the elastomeric member 2998. With the elastomeric member 2998 of the second plunger 2995 forming a substantially fluid tight seal with the inner surface of the second chamber 2991, such an increase in the portion of the inner volume 2994 that is distal to the elastomeric results in a negative pressure within that portion of the inner volume 2994. Moreover, with the distal end portion 2993 of the second chamber 2991 being closed and/or sealed, the movement of the second plunger 2995 within the second chamber 2991, for example, can act to dampen the movement of the actuator 2970 relative to the fluid reservoir 2960. Specifically, the increase of the portion of the inner volume 2994 distal to the elastomeric member 2998 produces, for example, a suction force therein that resists the proximal movement of the second plunger 2995. Thus, an effective force exerted on the actuator 2970 to move the first plunger 2975 within the first chamber 2990 and the second plunger 2995 within the second chamber 2991 can be modulated, reduced, limited, and/or otherwise controlled, which in turn, can limit a rate at which the actuator 2970 is moved relative to the fluid reservoir 2960. In other words, the arrangement of the second chamber 2991 and the second plunger 2995 dampen the force exerted on the actuator 2970 and thus, the movement of the actuator 2970 relative to the fluid reservoir 2960. Therefore, by limiting the rate at which the actuator 2970 is moved relative to the fluid reservoir 2960, a negative pressure within the inner volume 2964 of the first chamber 2991 and/or a rate at which blood (or other bodily-fluid) flows into the inner volume 2964 can be controlled to an extent that can reduce and/or substantially prevent hemolysis of the blood that can otherwise result from, inter alia, a volume of blood being exposed to a rapid pressure drop or the like.

Figure 63:
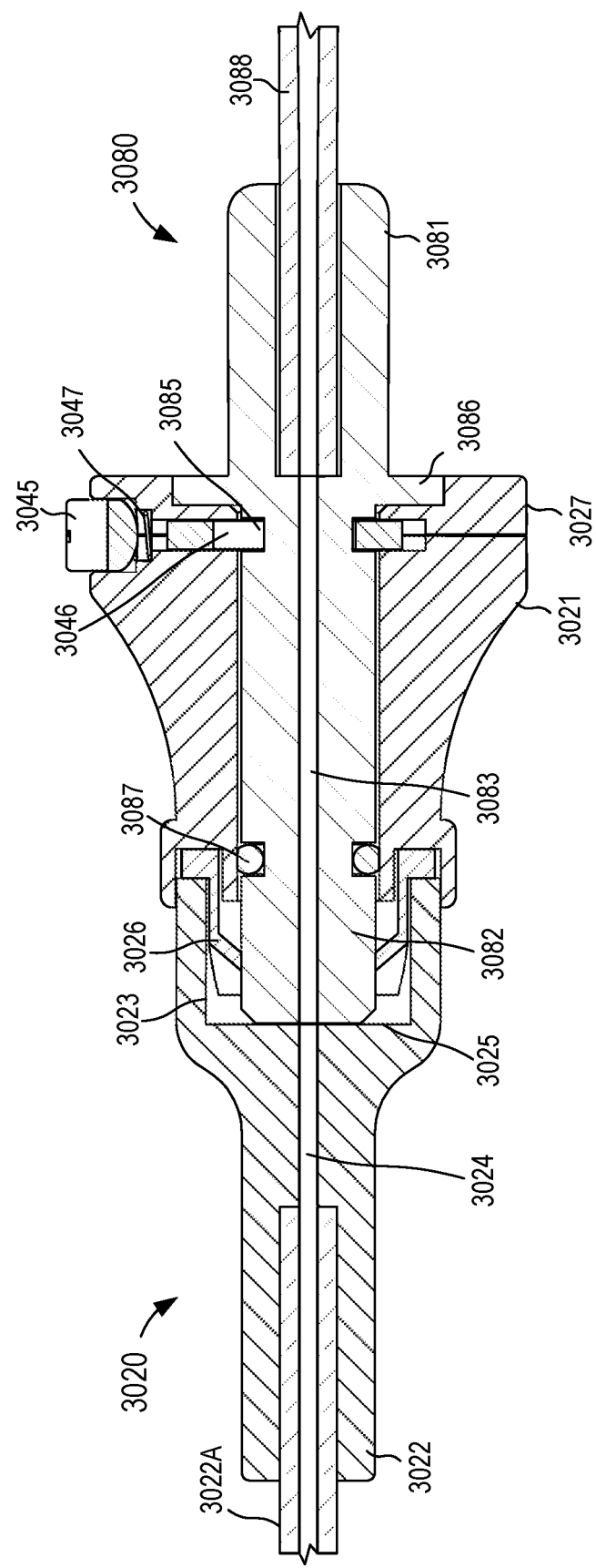
FIG. 63 is a cross-sectional view of the adapter of FIG. 61, taken along the line 63-63.

While the embodiments are shown and described above as defining a single flow path from the patient to a fluid reservoir, in some embodiments, a fluid transfer device and/or system can include, for example, any suitable extension set, Y-adapter, T-adapter, junction, split, and/or the like configured to define more than one fluid flow path. Moreover, in such embodiments, a fluid transfer device and/or system can include any suitable coupling mechanism, lock mechanism, hub, and/or the like configured to couple, for example, a first lumen-defining device to a second lumen-defining device such that hemolysis of a flow of blood therethrough is limited and/or substantially prevented. For example, FIGS. 61-71 illustrate embodiments configured to mitigate the risk of hemolysis as blood flows through a multi-lumen adapter and/or the like. Specifically, FIGS. 61-63 illustrate a hub 3020 configured to receive a lumen-defining device 3080 according to an embodiment.

The hub 3020 has a proximal end portion 3021, a distal end portion 3022 and an inner surface 3023 defining a lumen 3024 therethrough (see e.g., FIG. 63). The distal end portion 3022 of the hub 3020 includes and/or is coupled to a cannula 3022A and/or other suitable lumen-defining device. Although not shown in FIGS. 61-63, in some embodiments, the cannula 3022A can be coupled to an adapter, a restrictor, locking mechanism, and/or the like. In some embodiments, the cannula 3022A can be, for example, an indwelling cannula with a distal end portion disposed within the body of a patient. In other embodiments, the distal end portion 3022 of the hub 3020 can include and/or can form a locking mechanism configured to physically and fluidically couple the hub 3020 to any suitable device. The proximal end portion 3021 of the hub 3020 includes and/or is coupled to a proximal cap 3027 and an actuator 3045. For example, in some embodiments, the proximal cap 3027 can be coupled to the proximal end portion 3021 via a press fit, a snap fit, a friction fit, a threaded coupling, an adhesive, ultrasonic welding and/or the like. Moreover, the proximal cap 3027 defines an opening 3028 that is, for example, substantially aligned with the lumen 3024 defined by the inner surface 3023. In this manner, a portion of the lumen-defining device 3080 can be inserted through the opening 3028 of the proximal cap 3027 to be disposed within the hub 3020, as described in further detail herein.

As shown in FIGS. 62 and 63, the actuator 3045 is disposed between the proximal end portion 3021 and the proximal cap 3027. More specifically, the actuator 3045 forms a substantially annular ring or the like that is movably disposed within a space defined between a proximal surface of the hub 3020 and a distal surface of the proximal cap 3027. In this manner, the actuator 3045 defines an opening 3046 that can be selectively aligned with the opening 3028 of the proximal cap 3027 and the inner surface 3023 of the hub 3020. Moreover, the actuator 3045 includes and/or is coupled to a bias member 3047 (see e.g., FIG. 62), which can exert a force to temporarily maintain the actuator 3045 in a predetermined position relative to the hub 3020, for example, until a force is exerted on the actuator 3045 sufficient to overcome the force exerted by the bias member 3047, as described in further detail herein.

As shown in FIG. 63, the inner surface 3023 of the hub 3020 defines the lumen 3024 extending through its proximal end portion 3021 and its distal end portion 3022, which is configured to receive a portion of the lumen-defining device 3080. Furthermore, the inner surface 3023 includes and/or otherwise forms a shoulder 3025. In this embodiment, the shoulder 3025 is associated with a change in diameter of the inner surface 3023. For example, a first portion of the inner surface 3023 (e.g., a proximal portion) can have a first diameter that is larger than a diameter of a second portion of the inner surface (e.g., a distal portion). In this manner, the shoulder 3025 can be placed in contact with a surface of the lumen-defining device 3080 when inserted therein, as described in further detail herein.

The hub 3020 further includes a valve 3026 disposed within the lumen 3024. The valve 3026 can be, for example, a one-valve, a port, and/or the like, which can be transitioned between a first, substantially closed configuration and a second, substantially opened configuration. Thus, when in the first configuration, the valve 3026 can fluidically isolate a portion of the lumen 3024 that is proximal to the valve 3026 from a portion of the lumen 3024 that is distal to the valve 3026. Conversely, when the valve 3026 is in the second configuration, the lumen 3024 can define a fluid flow path substantially through the hub 3020. In some embodiments, the insertion of the portion of the lumen-defining device 3080 can be operable in transitioning the valve 3026 from the first configuration to the second configuration, as described in further detail herein.

The lumen-defining device 3080 has a proximal end portion 3031, a distal end portion 3032, and a flange 3086. The lumen-defining device 3080 also defines a notch 3085 and a lumen 3083 extending through the proximal end portion 3081 and the distal end portion 3082, as described in further detail herein. As shown in FIGS. 62 and 63, the distal end portion 3082 of the lumen-defining device 3080 is configured to be inserted through the proximal cap 3027 and the actuator 3045 to be disposed within the hub 3020, as described in further detail herein. Moreover, the lumen-defining device 3080 includes a seal member 3087 disposed about an outer surface of the distal end portion 3082, which is placed in contact with the inner surface 3023 of the hub 3020 which the lumen-defining device 3080 is disposed therein.

As shown, for example, in FIGS. 61 and 63, the proximal end portion 3081 of the lumen-defining device 3080 is physically and fluidically coupled to a cannula 3088. The cannula 3088 can be any suitable configuration. For example, in this embodiment, the cannula 3088 is a bifurcated cannula having a first portion 3088A and a second portion 3088B (also referred to herein as a "first cannula" and a "second cannula," respectively). The first portion 3088A and second portion 3088B can be physically and fluidically coupled to any suitable device (e.g., at a proximal end). For example, as shown in FIG. 61, the second portion 3088B includes a port or locking mechanism that can physically and fluidically couple the second portion 3088B to, for example, a fluid source and/or the like. Although not shown, the first portion 3088A can include a port or the like substantially similar to that of the second portion 3088B that can physically and fluidically couple the first portion 3088A to, for example, a fluid reservoir and/or the like. In other embodiments, the first portion 3088A and the second portion 3088B can be arranged in any suitable manner and can each be physically and fluidically coupled to any suitable device, mechanism, and/or member included in a fluid transfer system.

In use, a portion of the lumen-defining device 3080 can be inserted into the hub 3020 to define a fluid flow path between the cannula 3022A, coupled to the distal end portion 3022 of the hub 3020, and the cannula 3088 coupled to the proximal end portion 3081 of the lumen-defining device 3080. More specifically, in some instances, a user can manipulate the hub 3020 by exerting a force on the actuator 3045, thereby moving the actuator 3045 from a first position, in which the opening 3046 of the actuator 3045 is substantially unaligned with the opening 3028 of the proximal cap 3027, to a second position, in which the opening 3046 is aligned with the opening 3028. Thus, with the actuator 3045 in the second position, the opening 3028 of the proximal cap 3027, the opening 3046 of the actuator 3046, and the lumen 3024 of the hub 3020 are sufficiently aligned to allow the distal end portion 3082 of the lumen-defining device 3080 to be inserted through the proximal cap 3027, the actuator 3045, and into the lumen 3024. As shown in FIG. 63, the lumen-defining device 3080 can be inserted into the hub 3020 by a predetermined amount that places the distal end portion 3082 extends through the valve 3026, thereby transitioning the valve 3026 from its first, substantially closed configuration to its second, substantially open configuration. Moreover, a distal surface of the lumen-defining device 3080 in contact with the shoulder 3025, as shown in FIG. 63.

With the distal surface of the lumen-defining device 3080 in contact with the shoulder 3025, the flange 3086 of the lumen-defining device 3080 is disposed within a recessed surface defined by the proximal cap 3027. In some embodiments, the shape and/or size of the recessed surface and the flange 3086 can be such that the lumen-defining device 3080 is placed into a predetermined radial position such that the lumen 3024 of the hub 3020 and the lumen 3083 of the lumen-defining device 3080 are substantially aligned, as shown in FIG. 63. Moreover, the seal member 3087 disposed about the outer surface at or near the distal end portion 3082 of the lumen-defining device 3080 is placed in contact with the inner surface 3023 of the hub 3020. In this manner, the arrangement of the flange 3086 disposed within the recessed surface of the proximal cap 3027 and the seal member 3087 in contact with the inner surface 3023 of the hub 3020, the lumen-defining device 3080 is placed in a predetermined radial position relative to the hub 3020. For example, in this embodiment, the lumen 3083 of the lumen-defining device 3080 and the lumen 3024 of the hub 3020 form a substantially continuous transition therebetween. That is to say, the lumens 3083 and 3024 are substantially aligned and/or a discontinuity defined therebetween is sufficiently minimized or obviated so as to not produce turbulence within a flow of bodily-fluid therethrough.

In addition, once the lumen-defining device 3080 is disposed in the desired and/or predetermined position within the hub 3020, the user can remove the force exerted on the actuator 3045. As such, the bias member 3047 can exert a force to move the actuator 3045 from its second position to its first position (e.g., a biased position). Thus, as shown in FIG. 63, the actuator 3045 is moved out of alignment with the hub 3020, resulting in a portion of the actuator 3045 being disposed in the notch 3085 defined by the lumen-defining device 3080, which in turn, can maintain the lumen-defining device 3080 in a substantially fixed position within the hub 3020. In this manner, a user can couple the first portion 3088A or the second portion 3088B of the cannula 3088 to, for example, a fluid reservoir such as those described herein, which in turn, can exert a suction force (e.g., in response to a negative pressure differential) through the lumen-defining device 3080 and the hub 3020. Therefore, when the cannula 3022A is in fluid communication with the body of a patient (e.g., either directly or indirectly via an intervening structure), a volume of, for example, blood can be withdrawn with a reduced amount of hemolysis. Specifically, the alignment of the lumen 3024 defined by the hub 3020 and the lumen 3083 of the lumen-defining device 3080, for example, can reduce turbulence, eddy currents, and/or any other disturbance that can otherwise result from a discontinuity or the like. Thus, the flow of blood therethrough can be substantially laminar and substantially free of hemolysis.

Figure 64:
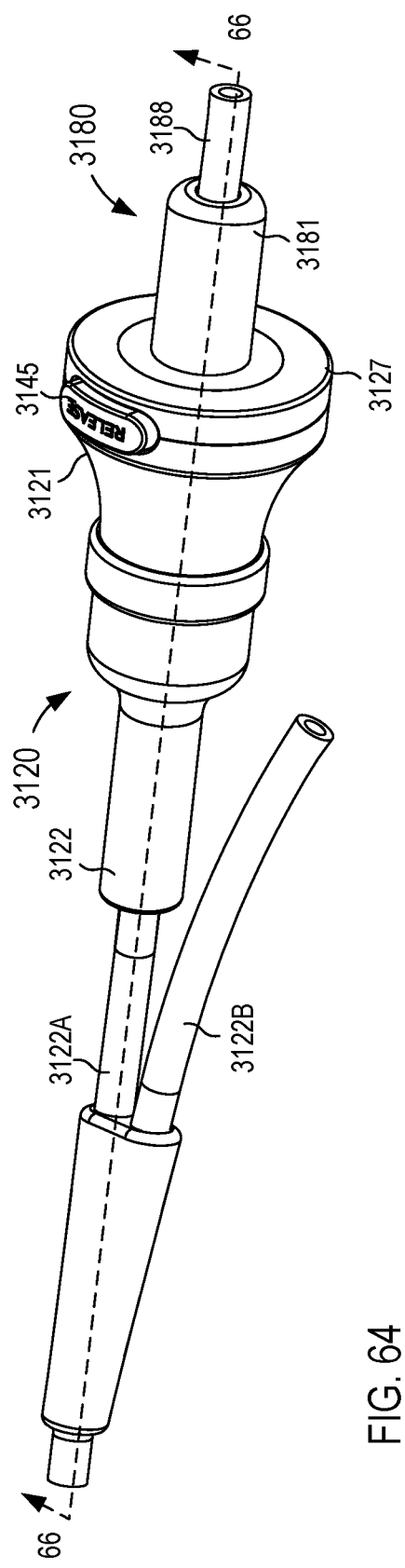
FIG. 64 is a perspective view of an adapter included in a bodily-fluid collection device according to another embodiment.
Figure 65:
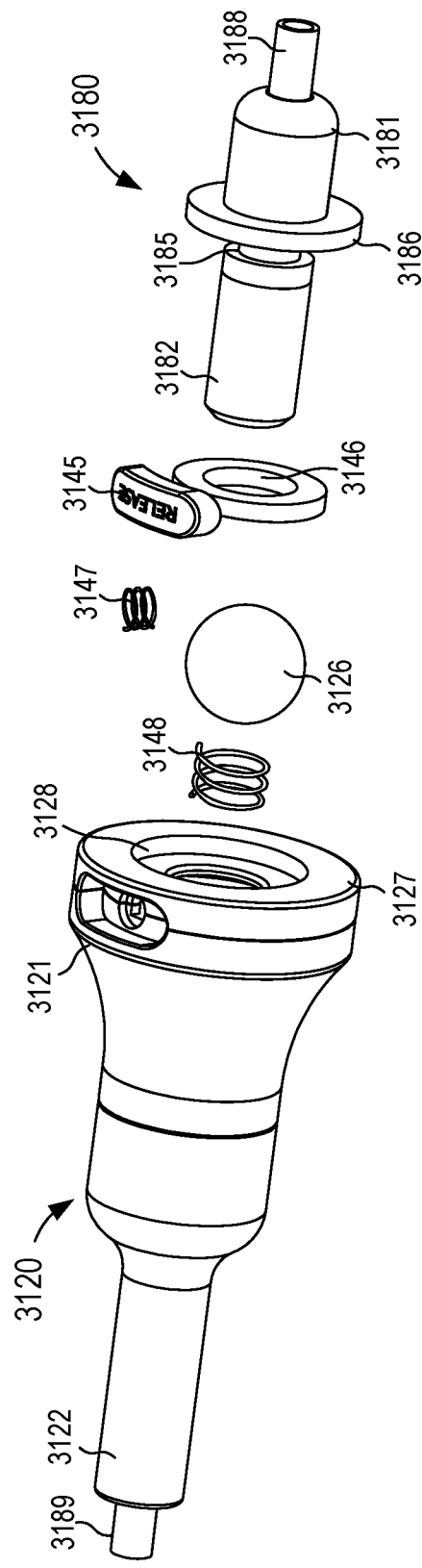
FIG. 65 is an exploded view of the adapter of FIG. 64.
Figure 66:
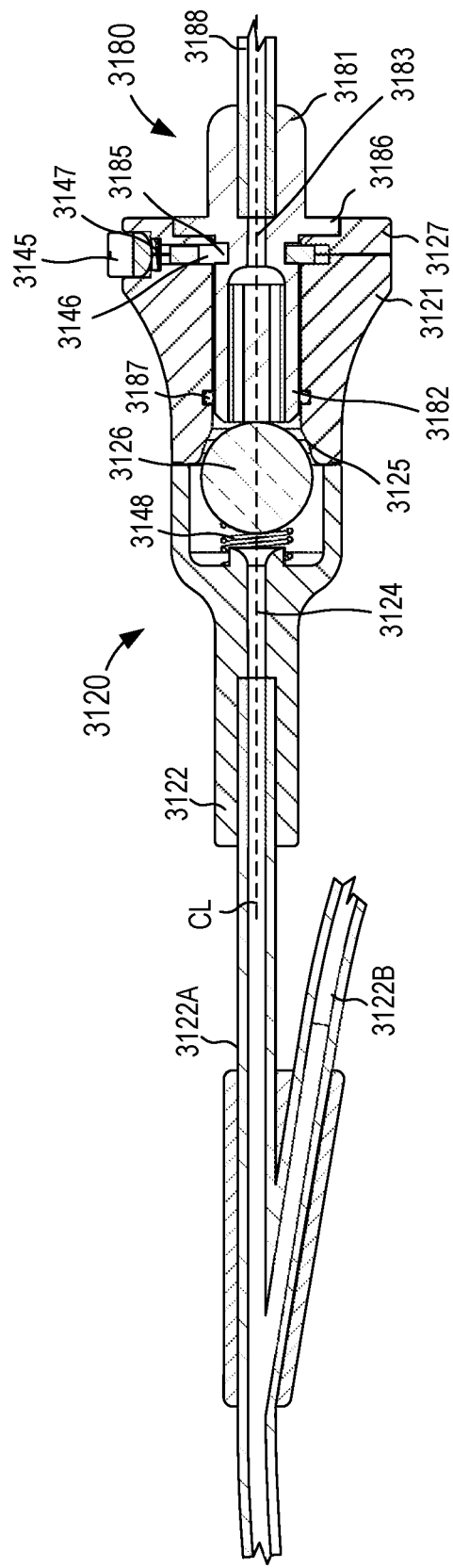
FIG. 66 is a cross-sectional view of the adapter of FIG. 65, taken along the line 66-66.

Although the valve 3026 is particularly shown and described above with reference to FIGS. 62 and 63, in other embodiments, a hub can include any suitable valve. For example, FIGS. 64-66 illustrate a hub 3120 configured to receive a lumen-defining device 3180 according to another embodiment. The hub 3120 and the lumen-defining device 3080 can be substantially similar in form and/or function as the hub 3020 and the lumen-defining device 3080 described above with reference to FIGS. 61-63. Thus, such similar aspects are not described in further detail herein.

As shown in FIGS. 64-66, the hub 3120 has a proximal end portion 3121, a distal end portion 3122, and an inner surface 3123 defining a lumen 3124 therethrough (see e.g., FIG. 66). The distal end portion 3122 of the hub 3120 includes and/or is coupled to a cannula 3122A and/or other suitable lumen-defining device. While the hub 3020 is shown and described as being coupled to a single cannula and/or a cannula defining a single lumen, in this embodiment, the hub 3120 is coupled to a bifurcated cannula having a first portion (also referred to herein as "first cannula" or "cannula 3122A") and a second portion 3122B. In other embodiments, the hub 3120 can be coupled to a single cannula and/or a cannula defining a single lumen. The proximal end portion 3121 of the hub 3120 includes and/or is coupled to a proximal cap 3127 and an actuator 3145, as described in detail above. The proximal cap 3127 defines an opening 3128 that is, for example, substantially aligned with the lumen 3124 defined by the inner surface 3123. In this manner, a portion of the lumen-defining device 3180 can be inserted through the opening 3128 of the proximal cap 3127 to be disposed within the hub 3120, as described in further detail herein.

As shown in FIGS. 65 and 66, the actuator 3145 is disposed between the proximal end portion 3121 and the proximal cap 3128. The actuator 3145 forms a substantially annular ring or the like that is movably disposed within a space defined between a proximal surface of the hub 3120 and a distal surface of the proximal cap 3127. In addition, the actuator 3145 includes and/or is coupled to a bias member 3147, which can exert a force to temporarily maintain the actuator 3145 in a predetermined position relative to the hub 3120, for example, until a force is exerted on the actuator 3145 sufficient to overcome the force exerted by the bias member 3147. In this manner, the arrangement of the proximal end portion 3121 of the hub 3120, proximal cap 3127, and the actuator 3145 can be substantially similar to the proximal end portion 3021 of the hub 3020, the proximal cap 3027, and the actuator 3045 described above with reference to FIGS. 62 and 63.

As shown in FIG. 66, the inner surface 3123 of the hub 3120 defines the lumen 3124 extending through its proximal end portion 3121 and its distal end portion 3122, which is configured to receive a portion of the lumen-defining device 3180. Furthermore, the inner surface 3123 includes a valve and a sealing surface 3125. As shown in FIG. 66, in this embodiment, the valve is a ball valve 3126, which can be transitioned between a first, substantially closed configuration and a second, substantially opened configuration. More specifically, the hub 3120 includes a bias member 3148 in contact with the ball valve 3126. In this manner, the bias member 3148 can exert a force on the ball valve 3126 that places the ball valve 3126 in contact with the sealing surface 3125. Thus, a contact sufficient to maintain a substantially fluid tight seal can be maintained when the ball valve 3126 is in contact with the sealing surface 3125 (e.g., in the first configuration) via a force exerted by the bias member 3148. Conversely, when a force exerted on the ball valve 3126, opposite the force exerted by the bias member 3148, is sufficient to overcome the force exerted by the bias member 3148, the ball valve 3126 can be removed from contact with the sealing surface 3125 and thus, a fluid flow path can be defined therethrough. In some embodiments, the insertion of the portion of the lumen-defining device 3180 can be operable in transitioning the ball valve 3126 from the first configuration to the second configuration, as described in further detail herein.

The lumen-defining device 3180 has a proximal end portion 3181, a distal end portion 3182, and a flange 3186. The lumen-defining device 3180 also defines a notch 3185 and a lumen 3183 extending through the proximal end portion 3181 and the distal end portion 3182, as described in further detail herein. As shown, for example, in FIGS. 64-66, the proximal end portion 3181 of the lumen-defining device 3180 is physically and fluidically coupled to a cannula 3188. The cannula 3188 can be any suitable configuration. For example, in this embodiment, the cannula 3188 is a single cannula and/or a cannula that defines a single lumen. In other embodiments, the cannula 3188 can be a bifurcated cannula, as described in detail above with reference to the cannula 3088 in FIG. 61. Moreover, although not shown in FIGS. 64-66, the cannula 3188 can include any suitable port, locking mechanism, and/or the like, as described above.

As shown in FIGS. 65 and 66, the distal end portion 3182 of the lumen-defining device 3180 is configured to be inserted through the proximal cap 3127 and the actuator 3145 to be disposed within the hub 3120, as described in further detail herein. Moreover, the lumen-defining device 3180 includes a seal member 3187 disposed about an outer surface of the distal end portion 3182, which is placed in contact with the inner surface 3123 of the hub 3120 which the lumen-defining device 3180 is disposed therein. As shown in FIG. 66, the lumen 3183 of defined by the lumen-defining device 3080 at or near the distal end portion 3182 is diverted, for example, into one or more channels and defining a substantially smooth transition therebetween. In some embodiments, the one or more channels, for example, can be offset from the lumen 3183 (e.g., non-coaxial). In other words, each channel is radially offset from a longitudinal centerline CL, as shown in FIG. 66. Thus, when a distal surface of the lumen-defining device 3180 is placed in contact with, for example, the ball valve 3126, the channels and/or the lumen 3183 are/is substantially unobstructed, as described in further detail herein.

In use, a portion of the lumen-defining device 3180 can be inserted into the hub 3120 to define a fluid flow path between the cannula 3122A, coupled to the distal end portion 3122 of the hub 3120, and the cannula 3188 coupled to the proximal end portion 3181 of the lumen-defining device 3180. More specifically, in some instances, a user can manipulate the hub 3120 by exerting a force on the actuator 3145, thereby moving the actuator 3145 from a first position, in which the opening 3146 of the actuator 3145 is substantially unaligned with the opening 3128 of the proximal cap 3127, to a second position, in which the opening 3146 is aligned with the opening 3128, as described in detail above. As shown in FIG. 66, the lumen-defining device 3180 can be inserted into the hub 3120 by a predetermined amount that places a distal surface of the lumen-defining device 3180 in contact with the ball valve 3126. In this manner, the lumen-defining device 3180 can be inserted into the hub 3180 until the flange 3186 of the lumen-defining device 3180 is disposed within a recessed surface defined by the proximal cap 3127, thereby aligning the lumen-defining device 3180, as described in detail above. Moreover, the seal member 3187 disposed about the outer surface at or near the distal end portion 3182 of the lumen-defining device 3180 is placed in contact with the inner surface 3123 of the hub 3120. In this manner, the lumen-defining device 3180 can be inserted into a position that removes the ball valve 3126 from the sealing surface 3125, thereby defining a fluid flow path between the lumen 3124 of the hub 3120 and the lumen 3183 (and/or channels) of the lumen-defining device 3180.

Once the lumen-defining device 3180 is disposed in the desired and/or predetermined position within the hub 3120, the user can remove the force exerted on the actuator 3145. As such, the bias member 3147 can exert a force to move the actuator 3145 from its second position to its first position (e.g., a biased position), resulting in a portion of the actuator 3145 being disposed in the notch 3185 defined by the lumen-defining device 3180. Thus, the actuator 3145 can maintain the lumen-defining device 3180 in a substantially fixed position within the hub 3120, as described in detail above. In this manner, a user can couple the cannula 3188, for example, to a fluid reservoir such as those described herein. Therefore, when the cannula 3122A is in fluid communication with the body of a patient (e.g., either directly or indirectly via an intervening structure), a volume of, for example, blood can be withdrawn with a reduced amount of hemolysis, as described in detail above. Specifically, the alignment of the lumen 3124 defined by the hub 3120 and the channels and/or lumen 3183 of the lumen-defining device 3180, for example, can reduce turbulence, eddy currents, and/or any other disturbance that can otherwise result from a discontinuity or the like. Thus, the flow of blood therethrough can be substantially laminar and substantially free of hemolysis.

Figure 67:
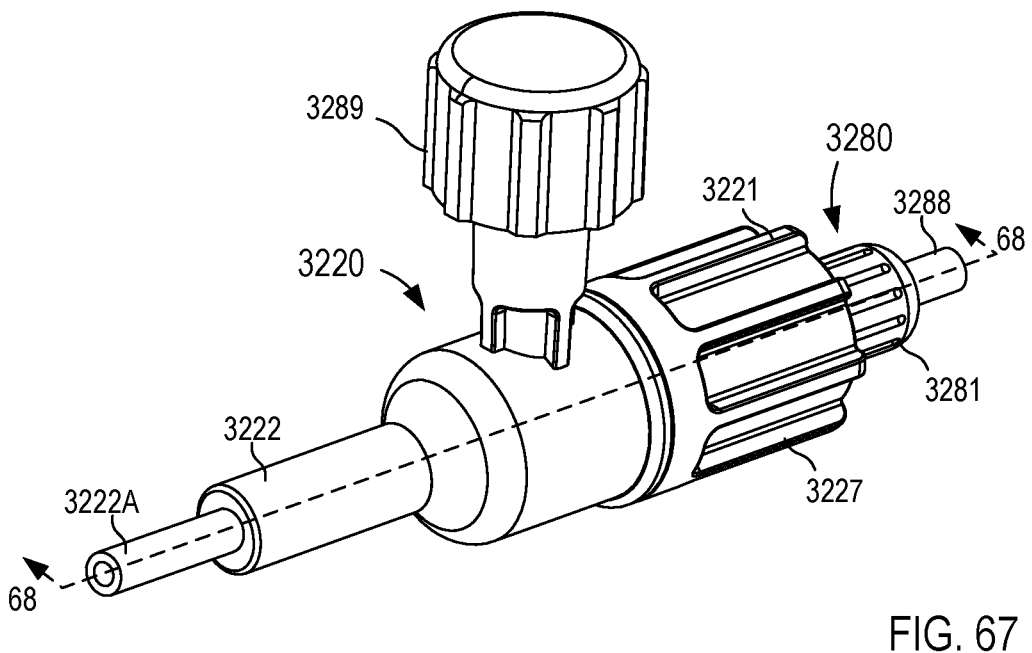
FIG. 67 is a perspective view of an adapter included in a bodily-fluid collection device according to another embodiment.
Figure 68:
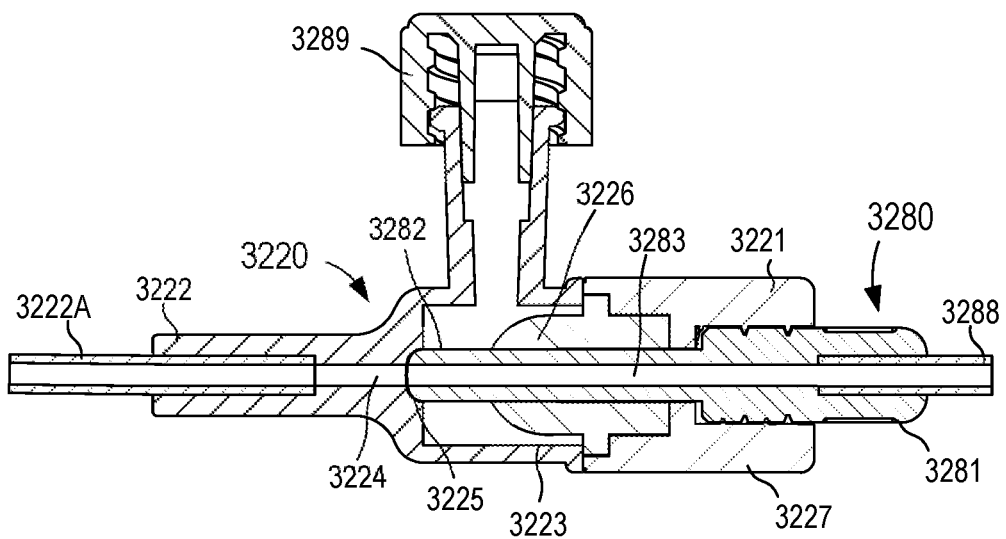
FIG. 68 is a cross-sectional view of the adapter of FIG. 67, taken along the line 68-68.

Although the hubs 3020 and 3120 have a proximal end portion including an actuator, in other embodiments, a hub can have any suitable configuration and need not include an actuator. For example, FIGS. 67 and 68 illustrate a hub 3320 configured to receive a lumen-defining device 3280 according to another embodiment. The hub 3220 and the lumen-defining device 3280 can be substantially similar in form and/or function as the hub 3020 and the lumen-defining device 3080 and/or the hub 3120 and the lumen-defining device 3180, described in detail above. Thus, such similar aspects are not described in further detail herein. As shown in FIGS. 67 and 68, the hub 3220 has a proximal end portion 3221, a distal end portion 3222, a secondary port 3289, and an inner surface 3223 defining a lumen 3224 therethrough (see e.g., FIG. 68). The hub 3220 further includes a valve 3226 disposed within the lumen 3224, as described in further detail herein.

The distal end portion 3222 of the hub 3220 includes and/or is coupled to a cannula 3222A and/or other suitable lumen-defining device, as described above with reference to the hub 3020 in FIGS. 61-63. The proximal end portion 3221 of the hub 3220 includes and/or is coupled to a proximal cap 3227. As shown in FIGS. 67 and 68, in this embodiment, the proximal cap 3237 can be, for example, a locking mechanism or the like configured to form a treaded coupling with a portion of the lumen-defining device 3280, as described in further detail herein.

As shown in FIG. 68, the inner surface 3223 of the hub 3220 defines the lumen 3224 extending through its proximal end portion 3221 and its distal end portion 3222, which is configured to receive a portion of the lumen-defining device 3280. Furthermore, the inner surface 3223 includes and/or otherwise forms a shoulder 3225. In this embodiment, the shoulder 3225 is associated with a change in diameter of the inner surface 3223. For example, a first portion of the inner surface 3223 (e.g., a proximal portion) can have a first diameter that is larger than a diameter of a second portion of the inner surface (e.g., a distal portion). In this manner, the shoulder 3225 can be placed in contact with a surface of the lumen-defining device 3280 when inserted therein, as described in detail above with reference to the hub 3020. In some embodiments, the shoulder 3225 can form, for example, a seat or a recessed portion configured to receive a portion of the lumen-defining device 3280.

The valve 3226 of the hub 3220 can be, for example, a one-valve, a port, and/or the like, which can be transitioned between a first, substantially closed configuration and a second, substantially opened configuration. Thus, when in the first configuration, the valve 3226 can fluidically isolate a portion of the lumen 3224 that is proximal to the valve 3226 from a portion of the lumen 3224 that is distal to the valve 3226. Conversely, when the valve 3226 is in the second configuration, the lumen 3224 can define a fluid flow path substantially through the hub 3220. In some embodiments, the insertion of the distal end portion 3282 of the lumen-defining device 3280 can be operable in transitioning the valve 3226 from the first configuration to the second configuration, as described in further detail herein.

The secondary port 3289 of the hub 3280 can be any suitable port or the like. For example, in some embodiments, the hub 3220 can be arranged as a T-adapter or the like, in which the proximal end portion 3221 defines a first port and the secondary port 3289 extends in a substantially perpendicular direction from the first port. In this manner, the secondary port 3289 is in fluid communication with the lumen 3224 defined by the hub 3220 and can be configured to receive and/or deliver a fluid from and/or to the lumen 3224 of the hub 3220. Moreover, the arrangement of the secondary port 3289 is such that when the valve 3226 is in its closed configuration, the secondary port 3289 is fluidically isolated from a portion of the lumen 3224 proximal to the valve 3226.

The lumen-defining device 3080 has a proximal end portion 3031, a distal end portion 3032, and a flange 3086. The lumen-defining device 3080 also defines a notch 3085 and a lumen 3083 extending through the proximal end portion 3081 and the distal end portion 3082, as described in further detail herein. As shown in FIGS. 62 and 63, the distal end portion 3082 of the lumen-defining device 3080 is configured to be inserted through the proximal cap 3027 and the actuator 3045 to be disposed within the hub 3020, as described in further detail herein. Moreover, the lumen-defining device 3080 includes a seal member 3087 disposed about an outer surface of the distal end portion 3082, which is placed in contact with the inner surface 3023 of the hub 3020 which the lumen-defining device 3080 is disposed therein.

The lumen-defining device 3280 has a proximal end portion 3281 and a distal end portion 3282, and defines a lumen 3283 therethrough. As shown, for example, in FIG. 68, the proximal end portion 3281 of the lumen-defining device 3280 is physically and fluidically coupled to a cannula 3288. The cannula 3288 can be any suitable configuration. For example, in this embodiment, the cannula 3288 is a single cannula and/or a cannula that defines a single lumen. In some embodiments, the cannula 3288 can be substantially similar to the cannula 3188 described above wither reference to FIGS. 64-66.

As shown in FIG. 68, the distal end portion 3282 of the lumen-defining device 3280 is configured to be inserted through the proximal cap 3227 to be disposed within the hub 3220. More specifically, a portion of the lumen-defining device 3280 can be inserted into the proximal cap 3227 and configured to form, for example, a threaded coupling or the like. For example, in some embodiments, a portion of an outer surface of the lumen-defining device 3280 can include a set of treads or the like configured to engage a corresponding set of threads included in and/or defined by the proximal cap 3227. Thus, in use, as the lumen-defining device 3280 is inserted through the proximal cap 3227, the proximal cap 3227 and/or the lumen-defining device 3280 can be rotated to form the threaded coupling therebetween. Moreover, the arrangement of the lumen-defining device 3280 can be such that when coupled to the proximal cap 3227, the distal end portion 3282 of the lumen-defining device 3280 extends through the valve 3226. Thus, the valve 3226 is transitioned from its first, substantially closed configuration to its second, substantially open configuration. In some embodiments, the valve 3226 can be configured to form a substantially fluid tight seal about a portion of the lumen-defining device 3280, which in turn, can maintain the secondary port 3289 in fluid isolation from, for example, the lumen 3283 of the lumen-defining device 3280. Moreover, the lumen-defining device 3280 is advanced such that a distal surface of the lumen-defining device 3280 is in contact with the shoulder 3225, as shown in FIG. 68.

In this embodiment, the arrangement of the lumen-defining device 3280 and the proximal cap 3227 (i.e., the coupling therebetween) is such that the lumen 3283 of the lumen-defining device 3280 and the lumen 3224 of the hub 3220 form a substantially continuous transition therebetween. That is to say, the lumens 3283 and 3224 are substantially aligned and/or a discontinuity defined therebetween is sufficiently minimized or obviated so as to not produce turbulence within a flow of bodily-fluid therethrough. Therefore, when the cannula 3222A is in fluid communication with the body of a patient (e.g., either directly or indirectly via an intervening structure), a volume of, for example, blood can be withdrawn with a reduced amount of hemolysis. Specifically, the alignment of the lumen 3224 defined by the hub 3220 and the lumen 3283 of the lumen-defining device 3280, for example, can reduce turbulence, eddy currents, and/or any other disturbance that can otherwise result from a discontinuity or the like. Thus, the flow of blood therethrough can be substantially laminar and substantially free of hemolysis.

Figure 69:
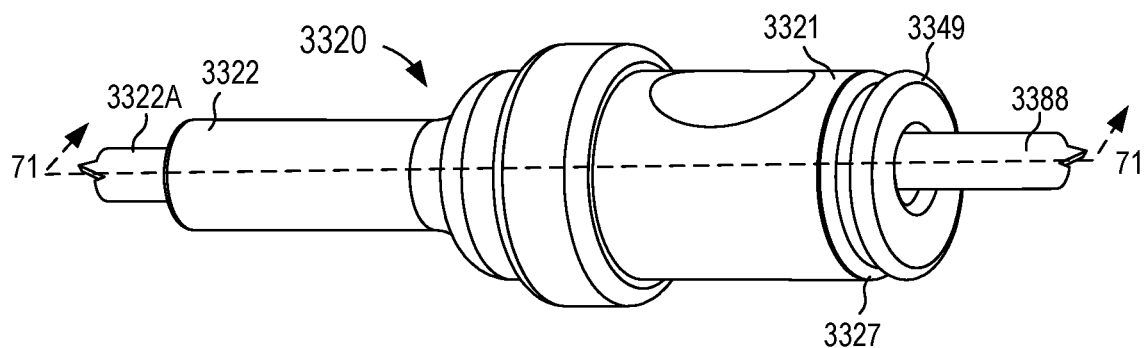
FIG. 69 is a perspective view of an adapter included in a bodily-fluid collection device according to another embodiment.
Figure 70:
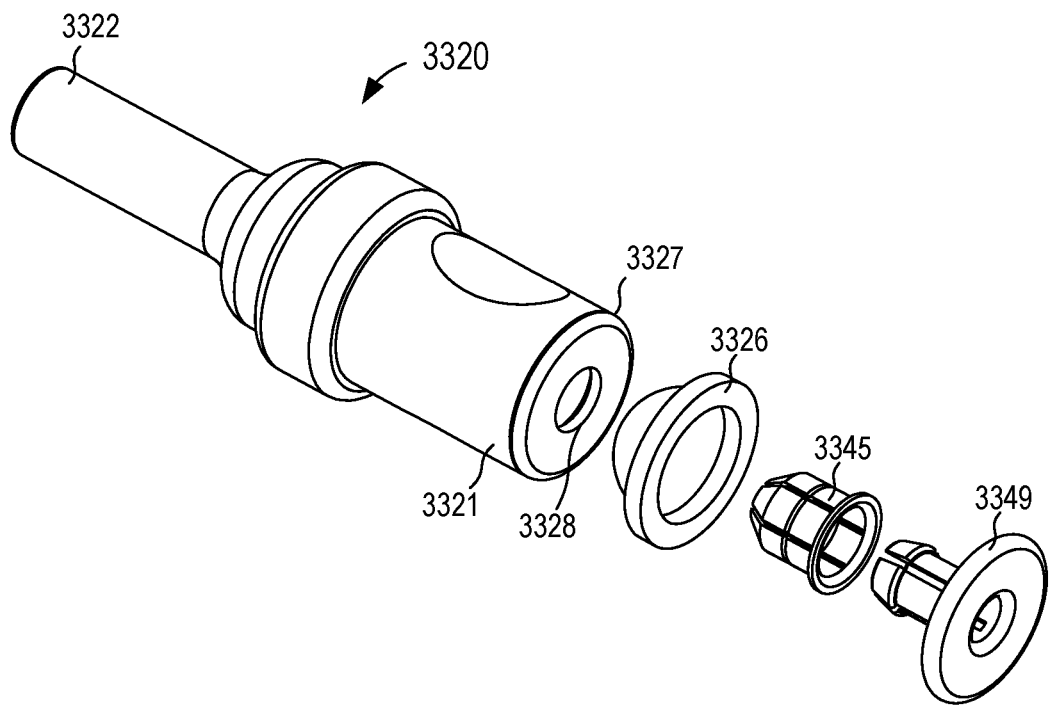
FIG. 70 is an exploded view of the adapter of FIG. 69.
Figure 71:
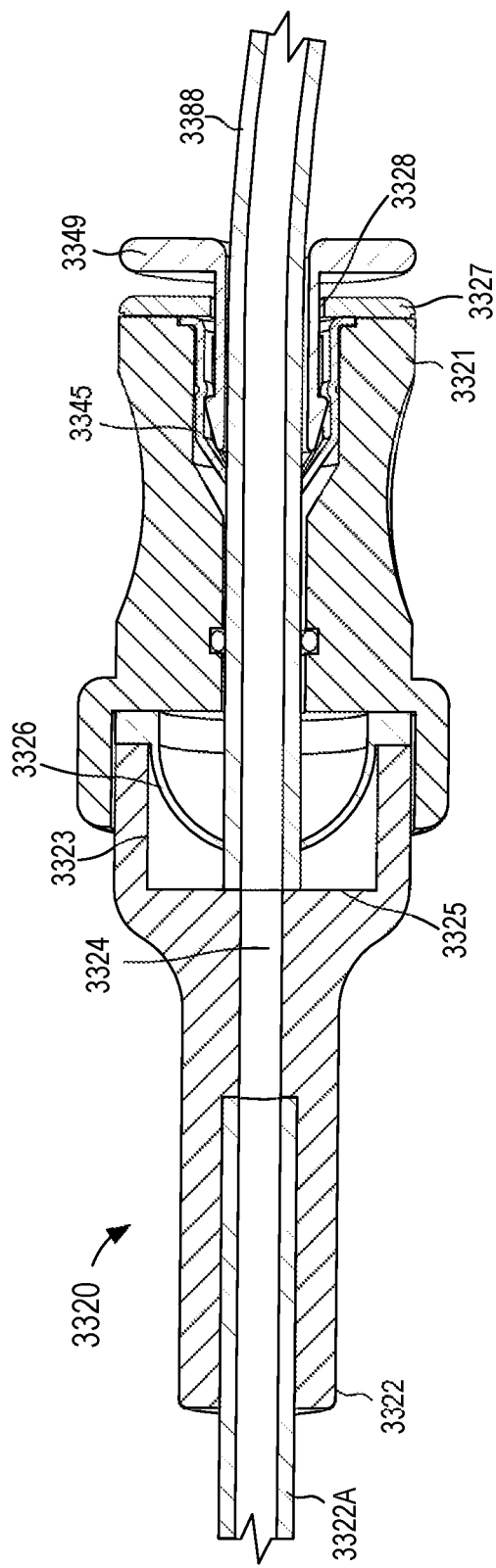
FIG. 71 is a cross-sectional view of the adapter of FIG. 69, taken along the line 71-71.

While the hubs 3020, 3120, and 3220 are shown and described above as receiving the lumen-defining devices 3080, 3180, and 3280 (e.g., a connector), respectively, in other embodiments, a hub can be configured to receive a terminated end of a cannula or the like (e.g., without a connector or other lumen-defining device). For example, FIGS. 69-71 illustrate a hub 3320 configured to receive a cannula 3388 according to another embodiment. The hub 3320 and the lumen-defining device 3080 can be substantially similar in form and/or function as the hub 3020 and the lumen-defining device 3080 and/or the hub 3120 and the lumen-defining device 3180, described in detail above. Thus, such similar aspects are not described in further detail herein.

As shown in FIGS. 69-71, the hub 3320 has a proximal end portion 3321, a distal end portion 3322, and an inner surface 3323 defining a lumen 3324 therethrough (see e.g., FIG. 71). The distal end portion 3322 of the hub 3320 includes and/or is coupled to a cannula 3322A and/or other suitable lumen-defining device. In some embodiments, the distal end portion 3322 of the hub 3320 can be substantially similar to the distal end portion 3322 of the hub 3020 described above with reference to FIGS. 61-63. The proximal end portion 3321 of the hub 3320 includes and/or is coupled to a proximal cap 3327, as described in detail above. The proximal cap 3327 defines an opening 3328 that is, for example, substantially aligned with the lumen 3324 defined by the inner surface 3323. In this manner, a portion of the cannula 3388 can be inserted through the opening 3328 of the proximal cap 3327 to be disposed within the hub 3320, as described in further detail herein.

As shown in FIGS. 70 and 71, the proximal end portion 3321 of the hub 3320 further includes and or is coupled to a first coupling member 3345 and a second coupling member 3349. As described above with reference to the actuator 3145, the first coupling member 3345 is disposed between the proximal end portion 3321 and the proximal cap 3327. The first coupling member 3345 is configured to selective receive a portion of the second coupling member 3349. The second coupling member 3349 is configured to be disposed about a portion of the cannula 3388. Thus, the second coupling member 3349 can be inserted substantially concurrently with the cannula 3388. Moreover, the second coupling member 3349 is configured to engage the first coupling member 3345 disposed within the hub 3320, for example, to at least temporarily maintain the cannula 3388 in a fixed position. For example, in some embodiments, the second coupling portion 3349 can form a snap fit, a press fit, a friction fit, and/or the like when placed in contact with the first coupling member 3345, as described in further detail herein.

As shown in FIG. 71, the inner surface 3323 of the hub 3320 defines the lumen 3324 extending through its proximal end portion 3321 and its distal end portion 3322, which is configured to receive a portion of the cannula 3388. Furthermore, the inner surface 3323 includes and/or otherwise forms a shoulder 3325. In this embodiment, the shoulder 3325 is associated with a change in diameter of the inner surface 3323. For example, a first portion of the inner surface 3323 (e.g., a proximal portion) can have a first diameter that is larger than a diameter of a second portion of the inner surface (e.g., a distal portion). In this manner, the shoulder 3325 can be placed in contact with a surface of the cannula 3388 when inserted therein, as described in detail above with reference to the hub 3020.

The hub 3320 further includes a valve 3326 disposed within the lumen 3324. The valve 3326 can be, for example, a one-valve, a port, and/or the like, which can be transitioned between a first, substantially closed configuration and a second, substantially opened configuration. Thus, when in the first configuration, the valve 3326 can fluidically isolate a portion of the lumen 3324 that is proximal to the valve 3326 from a portion of the lumen 3324 that is distal to the valve 3326. Conversely, when the valve 3326 is in the second configuration, the lumen 3324 can define a fluid flow path substantially through the hub 3320. In some embodiments, the insertion of the portion of the cannula 3388 can be operable in transitioning the valve 3326 from the first configuration to the second configuration, as described in further detail herein.

In use, a portion of the cannula 3388 can be inserted into the hub 3320 to define a fluid flow path between the cannula 3322A, coupled to the distal end portion 3322 of the hub 3320, and the cannula 3388 coupled to the proximal end portion 3381 of the cannula 3388. More specifically, in some instances, a user can insert an end portion of the cannula 3388 through the second coupling member 3349. Once the second coupling member 3349 is disposed about the cannula 3380, the cannula 3388 can be inserted into the hub 3320 by a predetermined amount that extends, for example, a distal end portion of the cannula 3388 through the valve 3326, thereby transitioning the valve 3326 from its first, substantially closed configuration to its second, substantially open configuration. Moreover, a distal surface of the cannula 3388 in contact with the shoulder 3325, as shown in FIG. 71. As the cannula 3388 is moved into its desired position within the hub 3320, the second coupling member 3349 is inserted through the opening 3328 defined by the proximal cap 3327 and into contact with the first coupling member 3345. Thus, the second coupling member 3349 can engage the first coupling member 3345 to define, for example, a snap fit or the like. In some embodiments, the arrangement of the second coupling member 3349 can be such that when it engages the first coupling member 3349, a space through which the cannula 3388 extends is reduced. As such, the second coupling member 3349 can clamp the cannula 3388 and with the second coupling member 3349 being coupled to the first coupling member 3345, the first coupling member 3345 and the second coupling member 3349 can act to at least temporarily maintain the cannula 3388 in a substantially fixed position relative to the hub 3320. Although described above as being moved substantially concurrently with the cannula 3388, in other embodiments, the second coupling member 3349 can be moved after the distal surface of the cannula 3388 is placed in contact with the shoulder 3325.

In some embodiments, the arrangement of the hub 3320 and the cannula 3388 is such that when the cannula 3388 is maintained in the substantially fixed position, the lumen 3324 of the hub 3320 is substantially aligned with a lumen defined by the cannula 3388. For example, in this embodiment, the lumen of the cannula 3388 and the lumen 3324 of the hub 3320 form a substantially continuous transition therebetween. That is to say, the lumens are substantially aligned and/or a discontinuity defined therebetween is sufficiently minimized or obviated so as to not produce turbulence within a flow of bodily-fluid therethrough. In this manner, a user can couple the cannula 3388 to, for example, a fluid reservoir such as those described herein, which in turn, can exert a suction force (e.g., in response to a negative pressure differential) through the cannula 3388 and the hub 3320. Therefore, when the cannula 3322A is in fluid communication with the body of a patient (e.g., either directly or indirectly via an intervening structure), a volume of, for example, blood can be withdrawn with a reduced amount of hemolysis. Specifically, the alignment of the lumen 3324 defined by the hub 3320 and the lumen of the cannula 3388, for example, can reduce turbulence, eddy currents, and/or any other disturbance that can otherwise result from a discontinuity or the like. Thus, the flow of blood therethrough can be substantially laminar and substantially free of hemolysis.

Figure 72:
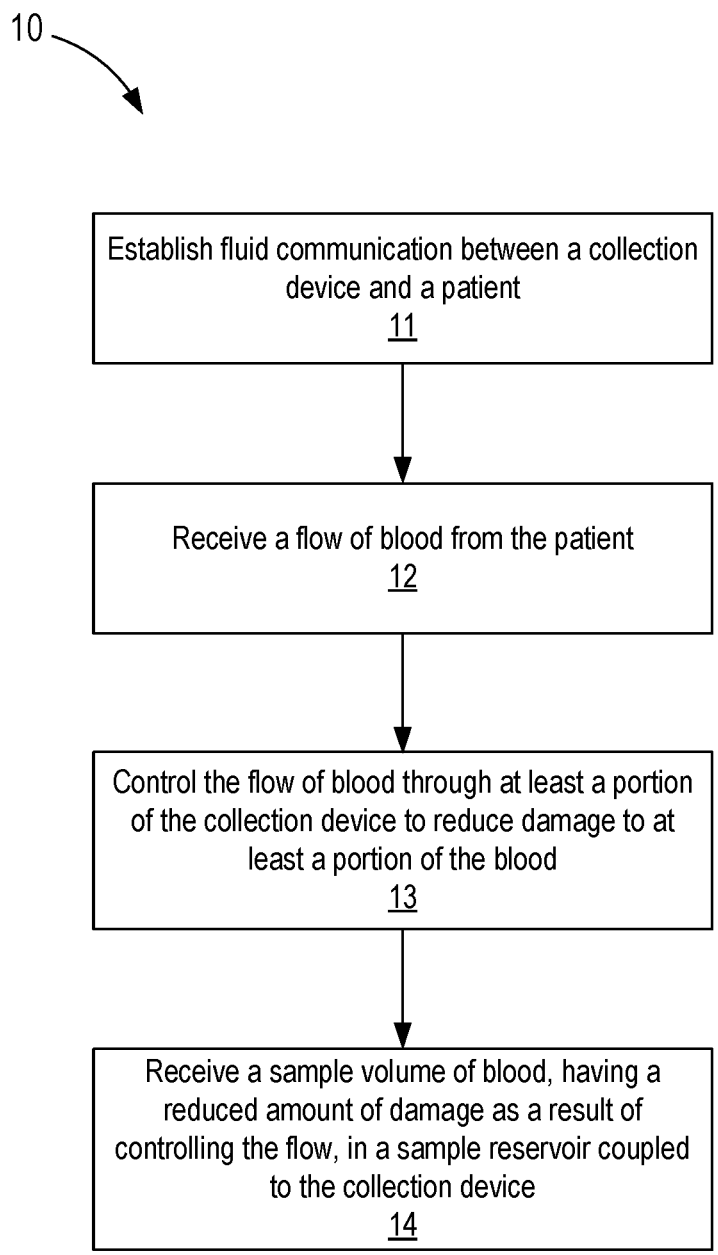
FIG. 72 is a flowchart illustrating a method of using a collection device to procure a blood sample with reduced damage from a patient according to an embodiment.

FIG. 72 is a flowchart illustrating a method 10 of using a collection device to procure a blood sample with reduced damage from a patient according to an embodiment. The collection device can be any of the embodiments described above with reference to specific embodiments or can be any suitable combination of the embodiments and/or features thereof. For example, in some embodiments, the collection device can be a puncture member or access device, an adapter, a hub, a restrictor, etc. such as those described above. As such, the collection device can be used to procure a volume (e.g., a sample volume) of blood or other bodilyfluids with reduced damage due to hemolysis and/or the like.

As shown, the method 10 includes establishing fluid communication between the collection device and a patient, at 11. In some embodiments, for example, the collection device can include and/or can be coupled to a lumen-containing device configured to be at least partially inserted into a patient. Such a lumen-containing device can be a puncture member such as a needle, catheter, and/or the like. In some embodiments, the lumen-containing device can be a puncture member similar to the puncture members 210, 310, 410, and/or 510 described above. In such embodiments, the puncture member can have one or more features configured to limit damage to a flow of fluid passing therethrough. For example, in some embodiments, such a puncture member can include a rounded distal surface or edge similar to the puncture member 210 described above with reference to FIGS. 2 and 3. In other embodiments, the lumen-containing device can be any suitable device configured to establish fluid communication with the patient. Furthermore, establishing fluid communication between the collection device and the patient can include, for example, coupling the collection device to such a lumen-containing device and/or inserting a portion of the lumen-containing device into a portion of the patient (e.g., a venipuncture event or the like).

With fluid communication established, a flow of blood is received from the patient, at 12. More specifically, a volume of blood (or other suitable bodily fluid) can be transferred from the patient to the collection device (e.g., via the lumen-containing device and/or any other suitable intermediate device). The flow of blood (or other suitable bodily fluid) is controlled as it flows into and/or through at least a portion of the collection device such that damage to at least a portion of the blood (or other suitable bodily fluid) is reduced, at 13.

For example, in some embodiments, the collection device and/or any suitable portion thereof can include an inner surface configured to produce a laminar flow of the blood (or other bodily fluid) flowing therethrough. In other embodiments, the inner surface can be configured to modulate a pressure differential that can otherwise result in a stress within the volume of blood or bodily-fluid flowing therethrough. In still other embodiments, the collection device can include one or more interfaces, connections, couplers, junctions, etc. configured to reduce discontinuities between coupled or connected fluid flow path. In yet other embodiments, the collection device can be configured to control a flow of blood or bodily fluid into or out of the collection device. In some embodiments, the collection device can include any features and/or means or any suitable combination features and/or means for controlling blood or bodily-fluid flow such as those described herein with reference to specific embodiments.

A sample volume of blood or bodily fluid having a reduced amount of damage as a result of controlling the flow is received in a sample reservoir coupled to the collection device, at 14. As described in detail above with reference to specific embodiments, the collection device can control the flow of blood and/or bodily fluid into and/or through the collection device to reduce, for example, hemolysis of a sample volume of blood. The collection device can be coupled to a sample reservoir in any suitable manner and/or using any suitable adapter, hub, and/or interface such as those described above. In some embodiments, the flow of blood or bodily fluid can also be controlled to reduce damage to the blood or bodily fluid. For example, in some embodiments, the collection device, an adapter, hub, and/or connector, and/or the sample reservoir can be configured to direct and/or control the flow of blood or bodily fluid into the sample reservoir. In some embodiments, such device(s) and/or reservoir(s) can be configured to modulate a pressure differential to which the flow of blood or bodily fluid is exposed and/or otherwise can be configured to modulate an amount of stress within at least a portion of the blood or bodily fluid. Accordingly, by controlling the flow of blood or bodily-fluid as it flows from the patient to the sample reservoir (e.g., via the collection device), a likelihood that a portion of the blood or bodily-fluid is damaged and/or hemolyzed is reduced, which in turn, reduces a likelihood of distorted, adulterated, inaccurate, and/or false test results otherwise associated with testing the damaged or hemolyzed blood or bodily-fluid.

Although the embodiments are shown and described above as mitigating the risk of hemolysis of a volume of blood at a given point along a fluid flow path between a patient and a fluid reservoir, any embodiment configured to mitigate the risk of hemolysis at a given point along the fluid flow path can be used in conjunction with any suitable embodiment(s) configured to mitigate the risk of hemolysis at a different point along the fluid flow path. In some instances, a fluid transfer device can include any combination of the embodiments described herein, for example, to mitigate the risk of hemolysis otherwise associated with (1) blood flow from, for example, a vein into a puncture member, needle, cannula, and/or the like; (2) blood flow through changing geometries and/or physical and fluidic interfaces; (3) blood flow rates, pressures, and/or velocities within the fluid flow path; (4) blood flow from an adapter, puncture member, needle, cannula, and/or the like into a fluid reservoir; (5) blood flow exposure to a negative pressure differential within a fluid reservoir; and/or (6) blood flow through a multi-lumen adapter and/or the like.

While the embodiments are shown and described above as mitigating the risk of hemolysis of a volume of blood during, for example, aspiration, blood draw, and/or any other procedure in which blood is withdrawn from the body, in other instances, any embodiment configured to mitigate the risk of hemolysis described herein, and/or any combination thereof, can be used in any suitable medical device and/or procedure in which it is desirable to reduce hemolysis. For example, any of the embodiments or combinations of the embodiments described herein such as the adapters, puncture members, restrictors, fluid reservoirs, gaskets, etc., and/or characteristics, geometries, and/or features thereof can be used to mitigate the risk of hemolysis in any suitable device and/or during any suitable medical procedure. Such devices and/or procedures can include but are not limited to, mechanical hearts and/or other organs, perfusion machines used, for example, during open-heart surgery, dialysis machines, and/or the like. In some instances, the embodiments and/or combination of embodiments described herein can be used to modulate pressure within such devices, produce a laminar flow through at least a portion of such devices, reduce and/or limit shear stress and/or exposure time experienced by red blood cells, and/or the like.

Although not shown or described herein, any of the embodiments can be used in a fluid transfer device configured to, for example, divert a predetermined pre-sample volume of bodily-fluid that can contain, for example, externally residing microbes prior to collection of a sample volume of bodily fluid. For example, in some embodiments, the predetermined pre-sample volume can be about a drop or a few drops of blood, about 0.1 mL, about 0.3 mL, about 0.5 mL, about 1.0 mL, about 2.0 mL, about 3.0 mL, about 4.0 mL, about 5.0 mL, about 11.0 mL, about 20 mL, about 50 mL, and/or any volume or fraction of a volume therebetween. In other embodiments, the pre-sample volume can be greater than 50 mL or less than 0.1 mL. In other embodiments, the predetermined pre-sample volume can be between about 2 mL and about 5 mL. In one embodiment, the predetermined pre-sample volume can be about 3 mL. In some instances, a venipuncture event can result in trauma to the blood flowing within the punctured vein that can at least temporarily hemolyze a portion of the blood. Thus, in some embodiments, the diverted pre-sample volume of blood can include, for example, the hemolyzed portion of the blood. Furthermore, by collecting the predetermined pre-sample volume, the predetermined sample volume disposed in one or more sample reservoirs can be substantially free-from externally residing microbes.

Fluid transfer devices configured to divert a predetermined pre-sample volume of bodily fluid can be any suitable configuration. For example, in some embodiments, such a fluid transfer device can be substantially similar to or the same as the fluid transfer devices described in U.S. Pat. No. 8,535,241 entitled, "Fluid Diversion Mechanism for Bodily-Fluid Sampling," filed Oct. 12, 2012; U.S. Pat. No. 9,060,724 entitled, "Fluid Diversion Mechanism for Bodily-Fluid Sampling," filed May 29, 2013; U.S. Pat. No. 9,155,495 entitled, "Syringe-Based Fluid Diversion Mechanism for Bodily-fluid Sampling," filed Dec. 2, 2013; and/or U.S. Patent Publication No. 2014/0155782 entitled, "Sterile Bodily-Fluid Collection Device and Methods," filed Dec. 4, 2012, the disclosures of which are incorporated herein by reference in their entireties. Moreover, in some embodiments, such transfer devices can be configured to selectively obstruct a needle to prevent hemolyzed blood from entering a lumen defined by the needle during a venipuncture event. Such devices can be substantially similar to and/or the same as those described in U.S. Patent Publication No. 2014/0276578, entitled, "Methods and Apparatus for Selectively Occluding the Lumen of a Needle," filed Sep. 18, 2014, the disclosure of which is incorporated herein by reference in its entirety.

In some embodiments, the bodily-fluid transfer devices described herein can include and/or can be partially formed from antisepsis-saturated materials. For example, any of the valves, gaskets, seals, ports, and/or the like can be saturated with, for example, isopropyl alcohol. As such, when various components of a fluid transfer device are coupled and/or otherwise collectively form an interface, the components can be contemporaneously sterilized. In some embodiments, such a device can be substantially similar to or the same as those described in U.S. Patent Publication No. 2015/0246352 entitled, "Apparatus and Methods for Disinfection of a Specimen Container," filed Mar. 3, 2015, the disclosure of which is incorporated herein by reference in its entirety.

While the device 100 is described above as including a surface, mechanism, portion, etc. configured to reduce hemolysis of a volume of blood in a mechanical manner (e.g., by mechanically changing one or more characteristics of a flow of blood within a fluid flow path), in other embodiments, any of the devices can be configured to chemically modify one or more characteristics associated with the volume of blood. For example, in some embodiments, an inner surface of any of the embodiments described herein can be coated with a chemical configured to limit lysis of erythrocytes (red blood cells) by strengthening or weakening a cell wall of the erythrocytes. More specifically, in some embodiments, a can be configured to introduce a chemical into a flow of blood that can, for example, increase a rigidity of the cell wall of erythrocytes (e.g., decrease flexibility), which in turn, can reduce a likelihood of lysis of the erythrocytes (e.g., hemolysis of the blood) as the blood flows through the device. In other embodiments, a device can be configured to introduce a chemical into a flow of blood that can, for example, decrease a rigidity of the cell wall of erythrocytes (e.g., increase flexibility), which in turn, can reduce a likelihood of lysis of the erythrocytes as the blood flows through the device.

While described above as coating an inner surface of a device with the chemical configured to modify a characteristic of the cell wall of the erythrocytes, in other embodiments, any of the embodiments described herein can include any suitable device, mechanism, and/or method for introducing such a chemical to the volume of blood flowing therethrough. For example, a device can include a chamber containing such a chemical (e.g., a chamber within a Luer lock or the like), a baffle, wipe, valve, porous material (e.g., sintered glass or plastic), etc. impregnated with such a chemical, a dispensing or dispersing device (e.g., sprayer or the like) configured to dispense a volume of such a chemical, and/or any other suitable means for introducing such a chemical. Moreover, a device can include any suitable combination of devices, interfaces, members, mechanisms, etc. included in the embodiments described herein as well as any suitable means for introducing a chemical into a volume of blood flowing through such a device.

As described above, in some instances, introducing a chemical into a volume of blood (e.g., whole blood) can result in a strengthening of an erythrocyte membrane or outer structure, or in other words, can modify a magnitude of stability associated with the erythrocyte membrane. In some instances, such stabilization can result in an increased resistance to hemolysis caused by mechanical stress, osmotic stress, peroxyl radicals attack, heat, and/or the like. Examples of chemicals that can modify a characteristic associated with an erythrocyte membrane include phloridzin, cremophore (glycerol polyethylene glycol ricinoleate, lidocaine, antioxidants such as reduced glutathione (GSH), N-acetylcysteine, ebselen (2-phenyl-1, 2-benzoselenazol-3-one) and/or albumin, papaya leaf and/or other plant extracts, tranquilizers and/or antihistamines such as phenothiazine, reserpine, and/or haloperidol, saponins and/or sapogenins, polyamines, anti-inflammatory drugs such as phenylbutazone, methylsergide, and/or indomethacin, and/or any other suitable chemical.

While various embodiments have been particularly shown and described, various changes in form and details may be made. While embodiments have been described above, it should be understood that they have been presented by way of example only, and not limitation. Although various embodiments have been described as having particular features and/or combinations of components, other embodiments are possible having any combination or sub-combination of any features and/or components from any of the embodiments described herein. For example, in some embodiments, a restrictor such as, for example, the restrictor 650 can be used when collecting a bodily fluid using any of the fluid reservoirs described herein. Similarly, the hub 3020 and lumen-defining device 3080 described above with reference to FIGS. 61-63 can be used with any of the adapters described herein. Moreover, any suitable combination of components described herein can be physically and/or fluidically coupled together to form a bodily-fluid collection device configured, for example, to reduce hemolysis in a withdrawn volume of blood.

The specific configurations of the various components can also be varied. For example, the size and specific shape of the various components can be different from the embodiments shown, while still providing the functions as described herein. More specifically, the size and shape of the various components can be specifically selected for a desired rate of bodily-fluid flow into a fluid reservoir. While various components have been described above a being physically and fluidically coupled, in other embodiments, any of the devices and/or embodiments can be, for example, monolithically formed with and/or otherwise joined to any other suitable device and/or embodiment. For example, while the first adapter 1020, the second adapter 1030, and the restrictor 1050 are described above with reference to FIGS. 18-20 as being formed separately and subsequently coupled, in other embodiments, the first adapter 1020 and/or the second adapter 1030 can be monolithically formed with the restrictor 1050. In some instances, such a monolithically formed component can be included in, for example, a pre-assembled and sterile blood collection device and/or the like.

Where methods and/or events described above indicate certain events and/or procedures occurring in certain order, the ordering of certain events and/or procedures may be modified. Additionally, certain events and/or procedures may be performed concurrently in a parallel process when possible, as well as performed sequentially as described above.

What is claimed:

1. A device for procuring a blood sample with reduced damage from a patient to reduce inaccurate results in testing of the blood sample, the device comprising:
    a first adapter having a distal end portion and a proximal end portion, the distal end portion configured to be placed in fluid communication with the patient, the first adapter defining a first lumen extending between the proximal end portion and the distal end portion, the first lumen having a first diameter;
    a second adapter having a distal end portion and a proximal end portion, the proximal end portion of the second adapter configured to be placed in fluid communication with a fluid reservoir, the second adapter defining a second lumen extending between the proximal end portion and the distal end portion of the second adapter, the second lumen having a second diameter; and
    a third adapter having a distal end portion configured to be coupled to the proximal end portion of the first adapter and a proximal end portion configured to be coupled to the distal end portion of the second adapter, the third adapter defining a distal lumen having a distal diameter substantially equal to the first diameter and a proximal lumen having a proximal diameter substantially equal to the second diameter, the third adapter having a medial portion forming a plurality of chambers disposed between the distal end portion and the proximal end portion of the third adapter, the plurality of chambers collectively defining an inner volume in fluid communication with each of the distal lumen and the proximal lumen of the third adapter,
    a cross-sectional area of the inner volume alternatingly increasing or decreasing between a smaller cross-sectional area associated with a position along a longitudinal centerline between adjacent chambers from the plurality of chambers and a larger cross-sectional area associated with a position along the longitudinal centerline substantially in the center of each chamber from the plurality of chambers, the plurality of chambers configured such that the cross-sectional area of the inner volume changes between the smaller cross-sectional area and the larger cross-sectional area with a continuous curvature,
    the plurality of chambers including a proximal chamber having a first volume, a distal chamber having a second volume greater than the first volume, and a medial chamber between the proximal chamber and the distal chamber, the medial chamber having a third volume greater than the second volume, the plurality of chambers configured to facilitate a laminar flow of the blood sample through the inner volume of the third adapter, and
    the first adapter, the second adapter, and the third adapter collectively defining a portion of a fluid flow path between the patient and the fluid reservoir when the third adapter is coupled between the first adapter and the second adapter, the plurality of chambers operable to reduce a negative pressure within a portion of the fluid flow path distal to the third adapter.

2. The device of claim 1, wherein reducing the negative pressure within the portion of the fluid flow path distal to the third adapter is operable to reduce damage to at least a portion of the blood sample flowing through the fluid flow path distal to the third adapter, and
    wherein the damage of at least the portion of the blood sample can produce inaccurate results in testing of the blood sample.

3. The device of claim 1, wherein a diameter of the inner volume of the third adapter at the position along the longitudinal centerline substantially in the center of each chamber from the plurality of chambers is greater than each of the first diameter and the second diameter.

4. The device of claim 1, wherein the plurality of chambers forms a set of semi-spherical portions of the third adapter.

* * * * *